(12) United States Patent
Southern

(10) Patent No.: US 12,360,122 B2
(45) Date of Patent: *Jul. 15, 2025

(54) HEALTH TEST FOR A BROAD SPECTRUM OF HEALTH PROBLEMS

(71) Applicant: GAIA MEDICAL INSTITUTE, La Jolla, CA (US)

(72) Inventor: Sarka O. Southern, San Diego, CA (US)

(73) Assignee: Gaia Medical Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/367,986

(22) Filed: Sep. 13, 2023

(65) Prior Publication Data

US 2023/0417771 A1    Dec. 28, 2023

Related U.S. Application Data

(63) Continuation of application No. 16/913,710, filed on Jun. 26, 2020, now abandoned, which is a continuation of application No. 16/421,089, filed on May 23, 2019, now Pat. No. 10,705,097, which is a continuation of application No. 15/873,840, filed on Jan. 17, 2018, now Pat. No. 10,317,416, which is a continuation of application No. 15/188,822, filed on Jun. 21, 2016, now Pat. No. 9,874,573, which is a continuation-in-part of application No. 14/870,825, filed on Sep. 30, 2015, now abandoned, which is a continuation of application No. 14/325,252, filed on Jul. 7, 2014, now Pat. No. 9,176,149, which is a continuation of application No. 13/122,130, filed as application No. PCT/US2009/059438 on Oct. 2, 2009, now Pat. No. 8,771,962.

(60) Provisional application No. 61/102,341, filed on Oct. 2, 2008.

(51) Int. Cl.
*G01N 33/68* (2006.01)
*A61B 10/00* (2006.01)
*A61B 10/02* (2006.01)
*G01N 30/88* (2006.01)

(52) U.S. Cl.
CPC ......... *G01N 33/6893* (2013.01); *A61B 10/00* (2013.01); *A61B 10/0045* (2013.01); *A61B 10/0051* (2013.01); *A61B 10/007* (2013.01); *A61B 10/025* (2013.01); *A61B 2010/0067* (2013.01); *A61B 2010/0074* (2013.01); *A61B 2010/0087* (2013.01); *A61B 2010/0258* (2013.01); *G01N 2030/8813* (2013.01); *G01N 2800/7004* (2013.01)

(58) Field of Classification Search
CPC ........ G01N 33/6893; G01N 2030/8813; A61B 10/0051; A61B 2010/0087
See application file for complete search history.

(56) References Cited

U.S. PATENT DOCUMENTS

| | | |
|---|---|---|
| 6,743,583 B2 | 6/2004 | Davis et al. |
| 6,964,851 B2 | 11/2005 | Boux et al. |
| 7,214,542 B2 | 5/2007 | Hutchinson |
| 7,927,548 B2 | 4/2011 | Slowey et al. |
| 7,951,612 B2 | 5/2011 | Angros et al. |
| 2002/0090620 A1 | 7/2002 | Davis et al. |
| 2003/0073160 A1 | 4/2003 | Boux et al. |
| 2003/0082597 A1 | 5/2003 | Cannon et al. |
| 2004/0029208 A1 | 2/2004 | Ravn |
| 2005/0025751 A1 | 2/2005 | Bodmer et al. |
| 2006/0231421 A1 | 10/2006 | Diamond et al. |
| 2006/0275861 A1 | 12/2006 | Angros et al. |
| 2008/0038760 A1 | 2/2008 | Mascart et al. |
| 2008/0262386 A1 | 10/2008 | Haar et al. |

FOREIGN PATENT DOCUMENTS

| | | | |
|---|---|---|---|
| WO | WO 0192879 A1 | 12/2001 | |
| WO | WO 2005034727 A2 | 4/2005 | |
| WO | WO 2005050224 A2 | 6/2005 | |
| WO | WO 2007045865 A2 | 4/2007 | |
| WO | WO 2009085574 A2 | 7/2009 | |
| WO | WO-2010019553 A2 * | 2/2010 | ........... A61B 5/4064 |

OTHER PUBLICATIONS

Levin et al., "Diagnosis, prognosis, and clinical management of mild traumatic brain injury," Lancet Neurol, http://dx.doi.org/10.1016/S1474-4422(15)00002-2, Mar. 20, 2015, pp. 1-12.

Atif et al., "A Review of MicroRNA Biomarkers in Traumatic Brain Injury", J Exp Neurosci, Mar. 2019, 13:1179069519832286, 12 pages.

Bazarian et al., "Serum GFAP and UCH-L1 for prediction of absence of intracranial injuries on head CT (Alert-TBI): a multicentre observational study", Lancet Neurol, 2018, 17(9):782-789.

CDC Injury Center, Report From the Pediatric Mild Traumatic Brain Injury Guideline Workgroup: Systematic Review and Draft Clinical Recommendations for Healthcare Providers on the Diagnosis and Management of Mild Traumatic Brain Injury Among Children, 2016, 93 pages.

Centers for Disease Control and Prevention (2019). Surveillance Report of Traumatic Brain Injury related Emergency Department Visits, Hospitalizations, and Deaths—United States, 2014. Centers forDisease Control and Prevention, U.S. Department of Health and Human Services, 24 pages.

Centers for Disease Control and Prevention. Report to Congress on Traumatic Brain Injury in the United States: Epidemiology and Rehabilitation, National Center for Injury Prevention and Control; Division of Unintentional Injury Prevention. Atlanta, GA., 2015, 72 pages.

Chiappelli et al., "Salivary Biomarkers in Psychobiological Medicine," Bioinformation, Biomedical Informatics Publishing Group, India, 2006, 1(8): 331-334.

(Continued)

*Primary Examiner* — Changhwa J Cheu
(74) *Attorney, Agent, or Firm* — DLA Piper LLP (US)

(57) ABSTRACT

Provided herein are methods and devices for the detection of conditions or disorders by detecting altered levels of stress response pathway biomarkers. Also provided are methods and reagents for identifying panels of biomarkers associated with a condition or disorder.

6 Claims, 23 Drawing Sheets

(56) References Cited

OTHER PUBLICATIONS

Chin et al., "A Simple and Reliable Pretreatment Protocol Facilitates Fluorescent in Situ Hybridisation on Tissue Microarrays of Paraffin Wax Embedded Tumour Samples," Journal of Clinical Pathology: Molecular Pathology, 2003, 56: 275-279.
Di Pietro et al., "MicroRNA Signature of Traumatic Brain Injury: From the Biomarker Discovery to the Point-of-Care", Front. Neurol., Jun. 14, 2018, 9(429): 1-15.
Diaz-Arrastia et al., "Acute biomarkers of traumatic brain injury: relationship between plasma levels of ubiquitin C-terminal hydrolase-L1 and glial fibrillary acidic protein", J Neurotrauma, Jan. 2014, 31(1):19-25.
Glinge et al., "Stability of Circulating Blood-Based MicroRNAs—Pre-Analytic Methodological Considerations", PLoS One, Feb. 2017, 12(2): e0167969, 16 pages.
Levin et al., "Diagnosis, prognosis, and clinical management of mild traumatic brain injury", Lancet Neurol, 14: 506-517, 2015.
Lumba-Brown et al. "Centers for Disease Control and Prevention guideline on the diagnosis and management of mild traumatic brain injury among children", JAMA Pediatrics, Nov. 2018, 172: e182853-e182853.
McCrory et al., "Consensus statement on concussion in sport—the 5th international conference on concussion in sport held in Berlin, Oct. 2016", British Journal of Sports Medicine, 2017, 5: 838-847.
Mucha et al., "A Brief Vestibular/Ocular Motor Screening (VOMS) assessment to evaluate concussions: preliminary findings", The American Journal of Sports Medicine, 2014, 42: 2479-2486.
Nagi et al., "Immunohistochemical detection of X-linked inhibitor of apoptosis in head and neck squamous cell carcinoma", Annals of Diagnostic Pathology, 2007, 11:402-406.
Nishida et al., "Association between Passive Smoking and Salivary Markers related to Periodontitis," Journal of Clinical Periodontology, 2006, 33: 717-723.
Papa et al., "Evaluating glial and neuronal blood biomarkers GFAP and UCH-L1 as gradients of brain injury in concussive, subconcussive and non-concussive trauma: a prospective cohort study", BMJ Paediatr Open, Aug. 2019, 3(1):e000473.

Pinchi et al., "MicroRNAs: The New Challenge for Traumatic Brain Injury Diagnosis", Curr Neuropharmacol, Apr. 2020, 18(4): 319-331.
Harmon et al., "American Medical Society for Sports Medicine position statement on concussion in sport", British Journal of Sports Medicine, 2019, 53: 213-225.
Kawata et al., "Blood biomarkers for brain injury: What are we measuring?", Neurosci Biobehav Rev, Sep. 2016, 68:460-473.
Kumar et al., "Heat Shock Protein 40 is Necessary for Human Immunodeficiency Virus-1 Nef-mediated Enhancement of Viral Gene Expression and Replication," The Journal of Biological Chemistry, Dec. 2, 2005, 280(48): 40041-40050.
Robert, "FDA clears path for first rapid handheld TBI biomarker test that could change sports", Forbes, Feb. 6, 2021, 5 pages.
Shi et al., "Antigen Retrieval Immunohistochemistry under the Influence of pH Using Monoclonal Antibodies," The Journal of Histochemistry and Cytochemistry, The Histochemical Society, Inc., 1995, 43(2): 193-201.
Southern et al., "New Technology for Early Detection of Health Threats," Proceedings of SPIE, 2008, 6945: 6945F-1-6945F-7.
St. John et al.. "Interleukin 6 and Interleukin 8 as Potential Biomarkers for Oral Cavity and (Oropharyngeal Squamous Cell Carcinoma," Archives of Otorhinolaryngology—Head & Neck Surgery, Aug. 2004, 130: 929-935.
Streckfus et al., "Cytokine Concentrations in Stimulated Whole Saliva Among With Primary Sjögren's Syndrome, Secondary Sjogren's Syndrome, and Patients With Primary Sjögren's Syndrome Receiving Varying Doses of Interferon for Symptomatic Treatment of the Condition: a Preliminary Study." Clinical Oral Investigations, 2001, 5: 133-135.
Streckfus et al., "Saliva as a Diagnostic Fluid," Oral Diseases, Stockton Press, Basingstoke, GB, Jan. 1, 2002, 8(2): 69-76.
Takai et al., "Effect of Psychological Stress on the Salivary Cortisol and Amylase Levels in Healthy Young Adults," Archives of Oral Biology, 2004, 49: 963-968.
Thodou et al., "Galectin-3 as a marker distinguishing functioning from silent corticotroph adenomas", Hormones, 2007, 6(3): 227-232.
Wang et al., "p63 in Pulmonary Epithelium, Pulmonary Squamous Neoplasm, and Other Pulmonary Tumors", Human Pathology, Sep. 2002, 33(9): 921-926.

* cited by examiner

Brush for Collecting Saliva Samples

| BIOMARKER | | DIAGNOSTIC ACCURACY | | | | | | |
|---|---|---|---|---|---|---|---|---|
| | | Hypertonic dehydration | | | | Control | Isotonic dehydration | |
| | | 2% DEH acute | 4% DEH acute | 4% DEH 12 hrs | REH in 2hr | EUH exercise | 4% DEH 12 hrs | REH in 2hr |
| Acidic Trehalase-like protein 1 | ATHL | 80% | 83% | 73% | 94% | 61% | 72% | 89% |
| Aldose Reductase | ALR | 76% | 84% | 83% | 99% | 51% | 89% | 99% |
| ALG-2 interacting protein X | Alix | 65% | 83% | 97% | 98% | 62% | 59% | 79% |
| Aquaporin 5 | AQP5 | 74% | 72% | 85% | 98% | 58% | 54% | 87% |
| CD63 | CD63 | 76% | 94% | 73% | 78% | 53% | 49% | 66% |
| Cyclin D1 | CYC D | 69% | 82% | 66% | 77% | 55% | 64% | 74% |
| Dicer | Dicer | 65% | 91% | 88% | 97% | 53% | 80% | 94% |
| Glucose regulated protein 75 | Grp75 | 83% | 86% | 79% | 96% | 64% | 65% | 94% |
| Glutathione S transferase pi | GST | 63% | 92% | 89% | 97% | 51% | 75% | 88% |
| Hyperosmotic glycerol response 1 | Hog1 | 82% | 91% | 79% | 96% | 60% | 80% | 97% |
| Leptin | Leptin | 54% | 55% | 86% | 82% | 53% | 59% | 79% |
| Mucin 1 | Muc1 | 77% | 89% | 88% | 77% | 65% | 64% | 65% |
| Neuropathy target esterase | NTE | 70% | 88% | 89% | 93% | 61% | 82% | 80% |
| Nitric oxide synthase 2, inducible | iNOS | 81% | 95% | 94% | 89% | 65% | 82% | 85% |
| Nuclear factor of activated T cells 5 | NFAT5 | 62% | 77% | 77% | 94% | 58% | 91% | 96% |
| Osmotic stress protein 94 | OSP94 | 63% | 64% | 85% | 94% | 59% | 87% | 91% |
| Sodium/myo-inositol cotransporter | SMIT | 88% | 89% | 94% | 93% | 55% | 74% | 88% |
| Taurine transporter | TauT | 59% | 79% | 87% | 100% | 64% | 52% | 79% |
| Toll-like receptor 2 | TLR2 | 76% | 92% | 79% | 98% | 63% | 60% | 90% |
| Trehalase | TRE | 84% | 88% | 86% | 98% | 59% | 74% | 87% |

| ROC analysis | Hypertonic dehydration 2% | Hypertonic dehydration 4% | Isotonic dehydration 4% | Combo dehydration Hypertonic & Isotonic | Rehydration | Control Euhydrated exercise |
|---|---|---|---|---|---|---|
| Diagnostic accuracy | 89% | 98% | 94% | 94% | 97% | 64% |
| Sensitivity | 80% | 98% | 85% | 88% | 92% | 93% |
| Specificity | 88% | 88% | 89% | 88% | 94% | 40% |

B

| | Gender effect | | | Daily and diurnal variability | | | | |
|---|---|---|---|---|---|---|---|---|
| ROC analysis | Males and Females | Males | Females | AM | PM | Day 1 | Day 2 | Day 3 |
| Diagnostic accuracy | 94% | 92% | 93% | 93% | 92% | 93% | 93% | 93% |
| Sensitivity | 88% | 86% | 90% | 88% | 88% | 88% | 89% | 88% |
| Specificity | 88% | 85% | 91% | 92% | 84% | 92% | 83% | 87% |

C

| Hydration Indicator | ROC analysis | 4% Hypertonic dehydration |
|---|---|---|
| Saliva biomarkers Cutoff 0.72 | Diagnostic accuracy | 98% |
| | Sensitivity | 98% |
| | Specificity | 88% |
| Posm Cutoff 297 mmol/kg | Diagnostic accuracy | 90% |
| | Sensitivity | 85% |
| | Specificity | 91% |
| USG Cutoff 1.025 | Diagnostic accuracy | 90% |
| | Sensitivity | 75% |
| | Specificity | 97% |
| Sodium Cutoff 142 mEq/L | Diagnostic accuracy | 93% |
| | Sensitivity | 33% |
| | Specificity | 100% |

FIG. 13A-13C

| Biomarker panel | AUC | Sensitivity % | Specificity % | p | Biomarker panel | AUC | Sensitivity % | Specificity % | p |
|---|---|---|---|---|---|---|---|---|---|
| Therapeutic monitoring | | | | | SAA | 0.949 | 87 | 91 | 0.001 |
| BST2 | 0.973 | 93 | 92 | 0.001 | VEGF-C | 0.827 | 87 | 78 | 0.001 |
| CD63 | 0.915 | 80 | 87 | 0.001 | *Case: unsuppressed HIV, Control: suppressed HIV* | | | | |
| HDAC | 0.883 | 93 | 61 | 0.001 | Acute HIV | | | | |
| Hsp90 | 0.817 | 80 | 78 | 0.002 | Cyt c | 0.887 | 95 | 74 | 0.001 |
| Mcl3 | 0.977 | 80 | 96 | 0.001 | Hsp90 | 0.879 | 84 | 73 | 0.001 |
| NTE | 0.972 | 93 | 91 | 0.001 | VEGF-C | 0.882 | 58 | 97 | 0.001 |
| OTB | 0.893 | 87 | 79 | 0.001 | *Case: Acute HIV, Control: HIV-negative STD* | | | | |

FIG. 16

STRESS RESPONSE PROFILING

A

| # | BIOMARKERS | | PATHWAYS |
|---|---|---|---|
| | | | 1 2 3 4 5 6 7 8 9 10 11 |
| 1 | Acidic Trehalase-like protein 1 | ATHL | 1 1 1 |
| 2 | Adrenocorticotropic hormone | ACTH | 1 1 |
| 3 | Aldose Reductase | ALR | 1 1 1 1 1 |
| 4 | ALG-2 interacting protein X | AIX | 1 1 1 |
| 5 | Annexin 5 | Annex | 1 1 1 |
| 6 | Apolipoprotein B mRNA editing enzyme | APO | 1 1 1 1 1 |
| 7 | Asagonin 5 | AGP5 | 1 1 1 |
| 8 | Betaine-GABA transporter 1 | BGT | 1 1 1 |
| 9 | Bone Marrow Stromal Cell Antigen 2 (Tatherin) | BST | 1 1 |
| 10 | Caspase 3 | Casp3 | 1 1 |
| 11 | Caspase 8 | Casp8 | 1 1 1 |
| 12 | CD63 (Tetraspanin, LAMP-3) | CD63 | 1 1 1 |
| 13 | COX | COX | 1 1 1 |
| 14 | Cyclin D1 | Cyclin | 1 1 1 1 1 |
| 15 | Cyclooxygenase -2 | COX | 1 1 1 1 1 |
| 16 | Cytochrome P450 2E1 | CYP | 1 1 1 1 1 1 |
| 17 | Cytochrome P450 Reductase | CYPCR | 1 1 1 1 1 1 |
| 18 | Defensin-beta 2 | HBD2 | 1 1 |
| 19 | Defensin-beta 3 | HBD3 | 1 |
| 20 | Defensin-beta 4 | HBD4 | 1 1 1 |
| 21 | DICER | DICER | 1 1 1 1 1 |
| 22 | Epidermal growth factor receptor | EGFR | 1 1 1 1 1 |
| 23 | Ferritin | Fer | 1 1 1 1 1 |
| 24 | Fos | Fos | 1 1 1 1 1 |
| 25 | Furin convertase (PACE) | Furin | 1 1 1 |
| 26 | Glucocorticoid receptor | GR | 1 1 1 1 1 1 |
| 27 | Glucose regulated protein 58 | Grp58 | 1 1 1 |
| 28 | Glucose regulated protein 75 (Mortalin) | Grp75 | 1 1 1 1 |
| 29 | Glutathione S transferase p | GST | 1 1 1 1 1 1 |
| 30 | Heat shock protein 27 | HSP27 | 1 1 1 1 1 1 1 1 |
| 31 | Heat shock protein 40 | HSP40 | 1 1 1 1 |
| 32 | Heat shock protein 60 | HSP60 | 1 1 1 1 |
| 33 | Heat shock protein 70 | HSP70 | 1 1 1 1 1 1 |
| 34 | Heat shock protein 90 | HSP90 | 1 1 1 1 1 1 1 1 |
| 35 | Heat shock protein transcription factor 1 | HSF | 1 1 1 1 1 1 |
| 36 | Heme oxygenase 1 | HO-1 | 1 1 1 1 |
| 37 | Histone 3 methyltransferase SET/DB1 | HMT | 1 |
| 38 | Histone deacetylase 1 | HDAC | 1 1 1 |
| 39 | Hyperosmotic glycerol response 1 (p38) | HOG | 1 1 1 |
| 40 | Hypoxia-induced factor alpha 1 | HIF | 1 1 1 1 1 1 |
| 41 | Integrin B1 | INT | 1 1 1 1 1 |
| 42 | Interleukin-1 beta | IL-1 | 1 1 1 1 |
| 43 | IL-6 | IL-6 | 1 1 1 1 |
| 44 | IL-8 | IL-8 | 1 1 1 1 1 |
| 45 | IL-10 | IL-10 | 1 1 1 1 1 |
| 46 | IL-12 beta | IL-12 | 1 |
| 47 | Intracellular adhesion molecule 1 (CD54) | ICAM | 1 1 |
| 48 | Jun | Jun | 1 1 1 1 1 |
| 49 | Leptin | Leptin | 1 1 1 1 1 |
| 50 | Leptin (obesity) receptor | ObR | 1 1 1 1 1 |

| Heart disease | Diagnostic accuracy of saliva biomarkers | | | | | | | | | |
|---|---|---|---|---|---|---|---|---|---|---|
| | ANNEX | Cox-2 | EGFR | LEP | MEK1 | mTOR | NFAT5 | OSP94 | SAPK | SOD3 |
| AHF, all cases | 87% | 90% | 94% | 92% | 93% | 87% | 86% | | 84% | 86% |
| HF-pEF | 94% | 92% | 100% | 95% | 100% | 93% | 95% | 96% | 93% | 86% |
| HF-rEF | 83% | 89% | 91% | 90% | 90% | 84% | 83% | | | 85% |
| AHF AFIB, all cases | 83% | 86% | | | | 81% | 80% | | 88% | 79% |
| AHF AFIB, new onset | 80% | 94% | 78% | | 78% | | | 86% | | |
| AHF AFIB, history only | 79% | 82% | | 85% | | 80% | 81% | | 88% | 83% |

B

| Kidney disease | Diagnostic accuracy of saliva biomarkers | | | | | |
|---|---|---|---|---|---|---|
| | ANNEX | EGFR | LEP | MEK1 | NFAT5 | OSP94 |
| AKI | 79% | 79% | 85% | | 85% | |
| CKD | 85% | 85% | | 81% | | 81% |

| Biomarker | Fold increase | Biomarker | Fold increase |
|---|---|---|---|
| MMP | 195 | Muc | 25 |
| IL1b | 92 | Mek1 | 25 |
| MAPp38 | 90 | LC3B | 25 |
| CD63 | 82 | GR | 24 |
| ALIX | 72 | EGFR | 24 |
| GST | 45 | HSP27 | 22 |
| ObR | 42 | IL8 | 21 |
| INT | 39 | Fer | 20 |
| CYPOR | 38 | Casp3 | 18 |
| DICER | 38 | APO | 17 |
| Grp75 | 37 | HSP90 | 16 |
| ANNEX | 35 | HSP60 | 16 |
| Furin | 33 | Leptin | 16 |
| MLKK | 33 | AQP5 | 15 |
| LAMP | 32 | CYCD | 13 |
| HBD2 | 31 | CYP450 | 13 |
| HDAC | 30 | mTOR | 11 |
| Hsg | 29 | ATHL | 11 |
| ICAM | 28 | COX | 11 |
| Casp8 | 27 | IL10 | 9 |
| Fos | 26 | CD9 | 9 |
| HBD3 | 25 | BST2 | 9 |
| MT | 25 | HIF | 8 |
| HSP40 | 25 | iRn | 7 |
| ALR | 25 | HAT | 7 |

FIG. 20C

HEALTH TEST FOR A BROAD SPECTRUM OF HEALTH PROBLEMS

CROSS-REFERENCE TO RELATED APPLICATIONS

This application is a continuation application of U.S. application Ser. No. 16/913,710 filed Jun. 26.2020, pending; which is a continuation application of U.S. application Ser. No. 16/421,089 filed May 23, 2019, now issued as U.S. Pat. No. 10,705,097; which is a continuation application of U.S. application Ser. No. 15/873,840 filed Jan. 17, 2018, now issued as U.S. Pat. No. 10,317,416; which is a continuation application of U.S. application Ser. No. 15/188,822 filed Jun. 21, 2016, now issued as U.S. Pat. No. 9,874,573; which is a continuation-in-part application of U.S. application Ser. No. 14/870,825 filed Sep. 30, 2015, now abandoned, which is a continuation application of U.S. application Ser. No. 14/325,252 filed Jul. 7, 2014, now issued as U.S. Pat. No. 9,176,149; which is a continuation application of U.S. application Ser. No. 13/122,130 filed Jun. 17, 2011, now issued as U.S. Pat. No. 8,771,962; which is a 35 USC § 371 National Stage application of international Application No. PCT/US2009/059438 filed Oct. 2, 2009, now expired; which claims the benefit under 35 USC § 119(e) to U.S. application Ser. No. 61/102,341 filed Oct. 2, 2008. The disclosure of each of the prior applications is considered part of and is incorporated by reference in the disclosure of this application.

INCORPORATION BY REFERENCE OF SEQUENCE LISTING

The material in the accompanying sequence listing is hereby incorporated by reference into this application. The accompanying sequence listing xml file. named GAIA1120-8 ST26.xml, was created on May 13, 2025 and is 3,617 bytes in size.

BACKGROUND OF THE INVENTION

Field of the Invention

The present invention relates generally to a device for detecting a stress response in a sample, and more specifically to methods of detecting a stress biomarker in a sample.

Background Information

Wellness products and services are increasingly popular, particularly in developed countries. Many are rooted in the traditional medicine, e.g., body care products, natural medicines, massage, acupuncture, sauna, spa treatments. New products and services include handheld devices for vital sign measurements, tests for 'good' or 'bad' metabolites such as antioxidants or cholesterol, and treatments such as cold laser or hyperbaric oxygen. Wellness products and services are sold at retail stores, walk-in clinics, integrative medicine facilities, health spas and gyms and through electronic healthcare companies that also provide integrated wellness services. Wellness products and services are typically selected using generalized recommendations (e.g., age and gender based), subjective tests such as health questionnaires and the pain scale, vital signs (blood pressure), weight and metabolite tests (e.g., cholesterol or glucose). New test are needed for personalized assessment of health, identification of the need for wellness products and selecting the best match for the personal need. Optimally, new tests will provide an early warning of a health problem and indicate the nature of the problem, in addition, new tests showing specific health benefits of wellness products and services are needed, in addition to the available anti-oxidant tests for nutritional supplements.

There is an urgent need for a new health test suitable for point-of-care (POC) settings. The test should be noninvasive and capable of detecting early signs of deteriorating health status. To be POC-expedient, the test should be rapid technically simple and inexpensive.

SUMMARY OF THE INVENTION

In accordance with the present invention, there are provided. POC devices useful for Stress Response Profiling (SRP) in saliva. In one embodiment, the device is a handheld digital device for mobile health monitoring (FIG. 6). The use of the device is intuitive (similar to a digital thermometer) and does not require training for use. The test is noninvasive, rapid and inexpensive, and capable of detecting early warnings of health problems. The SRP device can be used for preventative POC health screening, consumer-centric wellness care, routine clinical care, it can be used in emergency moms and trauma units, it can be used by first responders, by individuals for chronic disease management, it can be used in complementary and alternative medicine, military healthcare.

In accordance with the present invention, there are provided devices for detecting at least one stress response biomarker in a test sample. Such devices include a disposable module for uptake of a test sample and reagent storage, wherein the module contains reagents for assaying for at least one stress response biomarker; and a reusable module for signal detection and result display; wherein the reusable module displays a signal that indicates the presence of the at least one stress response biomarker in the test sample. In some embodiments, the signal provides a digital readout of a percentage above a baseline representing the presence of the at least one stress response biomarker in the test sample. In certain embodiments, the signal provides a visual indication representing the presence of the at least one stress response biomarker in the test sample. In one aspect, the visual indication is a color indication.

The device may be used to test a biological sample. In some embodiments, the test sample is selected from the group containing breath air, saliva, urine, sweat, tears, blood, serum, stool, phlegm, bone marrow, cerebrospinal fluid, seminal fluid, vaginal fluid, amniotic fluid, skin, breast milk, tissue, plant sap, an egg, microbial body, cells suspension or a combination thereof. In certain aspects the test sample is whole saliva.

In certain embodiments, the device further includes a means for accessing a database, wherein the database provides a correlation between the presence of the at least one stress biomarker molecule in the test sample and (i) the presence, absence, or severity, if present, of a particular disease state; or (ii) the likelihood that an organism from which the test sample was obtained will contract or be subject to a particular disease state. In some embodiments, the device assays for at least one stress response biomarker selected from the group consisting of Acidic Trehalase-like protein 1 (ATHL), Adrenocorticotropic hormone (ACTH), Aldose Reductase (ALR), ALG-2 interacting protein X (Alix), Annexin 5 (Annex), Apolipoprotein B mRNA editing enzyme APOBEC 3G (APO), Aquaporin 5 (AQP5), Betaine-GABA transporter 1 (BGT), Bone Marrow Stromal Cell Antigen 2 (BST2, Tetherin), Caspase 3 (Casp3), Caspase 8 (Casp8), CD63 (CD63, Tetraspanin, LAMP-3), CD9, Cyclin D1 (Cyclin), Cyclooxygenase-2 (Cox-2), Cytochrome P450 2E1 (CYP450), Cytochrome P450 Reductase (CYPOR). Human beta defensing 2 (HBD2) Human beta defensin 3 (HBD3), Human beta defensin 4 (HBD4), DICER, Epidermal growth factor receptor (EGFR), Ferritin (Fer), Fos (Fos), Furin convertase (Furin, PACE). Glucocorticoid receptor (GR), Glucose regulated protein 58 (Grp58), Glucose regulated protein 75 (Grp75, Mortalin), Giuthathione S transferase pi (GS fp), Heat shock protein 27 (HSP27), Heat shock protein 40 (HSP40), Heat shock protein 60 (HSP60), Heat shock protein 70 (HSP70), Heat shock protein 90 (HSP90), Heat shock protein transcription factor 1 (FISF1), Heine oxygenase 1 (HO-1), Histone 3 methyltransferase SUV39H (HAT), Histone deacetylase 1 (HDAC), Hyperosmotic glycerol response 1 (p38) (HOG), Hypoxia-induced factor alpha 1 WW1), Integrin B1 (INTb), Interleukin-1 beta (1), IL-6 (IL-6), IL-8 (IL-8), IL-10 (IL-10), IL-12 beta (IL-12), Intracellular adhesion molecule-1 (ICAM CD54), Jun (Jun), Leptin, Leptin (obesity) receptor (ObR), Lysosome-associated membrane glycoprotein-1. (LAMP-2), MAP kinase p38 (p38), MAP kinase Mek-1, mitogen activated (MEK1), MAP kinase Mekk-1, stress activated (MEKK1), MAP kinase Jnk1/2, stress activated protein kinase (SAPK), Mammalian target of rapamycin (mTOR), Matrix metalloproteinase 9 (MMP9), Metallothionein (MT), Microtubule-associated protein light chain 3 β (MAP-LC3β, LC3), Mucin 1 (Muc1), Myeloperoxidase (MPO), Natriuretic peptide B (BNP), Natriuretic peptide receptor A (NPR), Neutrophil gelatinase-associated lipocalin 1 (NGAL). Neuropathy target esterase (NTE), Nitric oxide synthase, neuronal nNOS (NOS1), Nitric oxide synthase inducible iNOS (NOS2), Nuclear factor of activated T cells 5 (NFAT5, TonEBP), Ornithine decarboxylase (ODC), Osmotic stress protein 94 (OSP94), Oxytocin receptor (OTR), Pro-opiomelanocortin/beta-endorphin (POMC), p53 tumor suppressor (p53), Peripheral benzodiazepine receptor (PBR), Salivary Agglutinin gp340 (SAG). Salivary alpha amylase (SAA), Secretory leukocyte protease inhibitor (SLPI), Sodium/myo-inositol cotransporter (SMIT). Superoxide dismutase 1 Cu/Zn (SOD1), Superoxide dismutase 2 Mn (SOD2), Superoxide dismutase 3 Extracellular (SOD3), Substance P (SP), Substance P (Neurokinin 1) receptor (NKR), Serotonin Receptor 1A (SR1), Serotonin Receptor 2A (SR2). Taurin transporter (TauT), Tumor Growth Factor beta 1, 2, 3 (TGF), Toll-like receptor 2 (TLR2), Toll-like receptor 3 (TLR3), Toll-like receptor 4 (TLR4), Toll-like receptor 7 (TLR7), Toll-like receptor 8 (TLR8), Trehalase neutral (TRE), Ubiquitin (UB), Urotensin II (UT), Vascular adhesion molecule-1 (VCAM1), Vascular endothelial growth factor C (VEGF-C), VEGF receptor 1 (VEGFR-1, Flt-1) (VEGFR), Vasointestinal peptide (VIP), Vimentin (Vim) or a combination thereof. In one aspect, the device includes at least one stress biomarker associated with dehydration. In an additional aspect, dehydration is hypertonic dehydration, isotonic dehydration or hypotonic dehydration. In certain aspects, the at least one stress biomarker associated with dehydration comprises Acidic Trehalase-like protein 1 (ATHL), Osmotic stress protein 94 (OSP94), Sodium/myo-inositol cotransporter (SMIT) or a combination thereof. In another aspect, the device includes at least one stress biomarker associated with AIDS progression (unsuppressed HIV) and/or acute HIV. In certain aspects, the at least one stress biomarker associated with AIDS progression (unsuppressed HIV) and/or acute HIV comprises Bone Marrow Stromal. Cell Antigen 2 (BST2), Salivary Agglutinin gp340 (SAG), Vascular endothelial growth factor C (VEGF-C) or a combination thereof. In a further aspect, the device includes at least one stress biomarker associated with heart disease. In an additional aspect, heart disease is acute heart failure (AHF) with preserved ejection fraction (HF-pEF), acute heart failure (AHF) with restricted ejection fraction (HE-rEF) or atrial fibrillation (AFIB). In certain aspects, the at least one stress biomarker associated with heart disease comprises Cyclooxygenase-2, Epidermal growth factor receptor, Leptin, MAP kinase Mek-1 or a combination thereof. In one aspect, the device includes at least one stress biomarker associated with traumatic brain injury (TBI). In an additional aspect, traumatic brain injury is mild TBI (mTBI, concussion), severe TBI (sTBI) or neurocognitive disorder (NCD) due to TBI (NCDT). In certain aspects, the at least one stress biomarker associated with neurocognitive disorder (NCD) due to TBI (NCDT) comprises Cytochrome P450 Reductase (CYPOR), Natriuretic peptide receptor A (NPR), Oxytocin receptor (OTR) or a combination thereof. In another aspect, the device includes at least one stress biomarker associated with post-traumatic stress disorder (PTSD). In an additional aspect, the device includes at least one stress biomarker associated with kidney disease, including chronic kidney disease (CKD) and acute kidney injury (AKI). In certain aspects, the at least one stress biomarker associated with kidney disease comprises Annexin 5, Nuclear factor of activated T cells 5, Osmotic stress protein 94 or a combination thereof.

In another embodiment of the invention, there are provided methods for detecting a condition or disorder associated with a stress response in a subject. The methods include detecting an altered level of at least one biomarkers in an stress response biomarker panel a sample comprising salivary cells from a subject, as compared to a corresponding sample from a normal subject, wherein the panel comprises at least two biomarkers, and wherein further an alteration in the level of biomarker is indicative of a stress response associated with the condition or disorder, thereby detecting the condition or disorder in the subject. In one embodiment, the sample is whole saliva. In particular embodiments, the at least one stress response biomarker is selected from the group consisting of Acidic Trehalase-like protein 1 (ATHL), Adrenocorticotropic hormone (ACTH), Aldose Reductase (ALR), ALG-2 interacting protein X (Mix), Annexin 5 (Annex), Apolipoprotein B mRNA editing enzyme APOBEC 3G (APO). Aquaporin 5 (AQP5), Betaine-GABA transporter 1 (BGT), Bone Marrow Stromal Cell Antigen 2 (BST2, Tetherin), Caspase 3 (Casp3), Caspase 8 (Casp8), CD63 (CD63, Tetraspanin, LAMP-3), CD9, Cyclin D1 (Cyclin), Cyclooxygenase-2 (Cox-2), Cytochrome P450 2E1 (CYP405), Cytochrome P450 Reductase (CYPOR), Human beta defensing 2 (HBD2,) Human beta defensin 3 (HBD3), Human beta defensin 4 (HBD4), DICER, Epidermal growth factor receptor (EGFR), Ferritin (Fer), Fos (Fos), Furin convertase (Furin, PACE), Glucocorticoid receptor (OR), Glucose regulated protein 58 (Grp58), Glucose regulated protein 75 (Grp75, Mortalin), Gluthathione S transferase pi (GSTp), Heat shock protein 27 (HSP27), Heat shock protein 40 (HSP40), Heat shock protein 60 (HSP60), Heat shock protein 70 (HSP70), Heat shock protein 90 (HSP90), Heat shock protein transcription factor 1 (HSP1), Herne oxygenase 1 (HO-1), Histone 3 methyltransferase SUV39H (HAT), Histone deacetylase 1 (HDAC), Hyperosmotic glycerol response 1 (p38) (HOG), Hypoxia-induced factor alpha 1 (HIF1), Integrin 131 (INTb), Interleukin-1 beta (IL-1), IL-6 (IL-6), IL-8 (IL-8). IL-10 (IL-10), IL-12 beta (IL-12), Intracellular adhesion molecule-1 (ICAM1 CD54), Jun (Jun), Leptin, Leptin (obesity) receptor (ObR). Lysosome-associated membrane glycoprotein-1 (LAMP-2), MAP kinase p38 (p38), MAP kinase Mek-1, mitogen activated (MEK1), MAP kinase Mekk-1, stress activated (MEKK1), MAP kinase Jnk1/2, stress activated protein kinase (SAPK), Mammalian target of rapamycin (mTOR), Matrix metalloproteinase 9 (MMP9), Metallothionein (MT), Microtubule-associated protein light chain 3 β (MAP-LCβ, LC3), Mucin 1 (Muc1), Myeloperoxidase (MPO), natriuretic peptide B (BNP), Natriuretic peptide receptor A (NPR), Neutrophil gelatinase-associated lipocalin 1 (NGAL), Neuropathy target esterase (NTE), Nitric oxide synthase, neuronal nNOS (NOS1), Nitric oxide synthase, inducible iNOS (NOS2), Nuclear factor of activated T cells 5 (NFAT5, TonEBP), Ornithine decarboxylase (ODC), Osmotic stress protein 94 (OSP94), Oxytocin receptor (OTR), Pro-opiomelanocortin/beta-endorphin (POMC), p53 tumor suppressor (p53), Peripheral benzodiazepine receptor (PBR), Salivary Agglutinin gp340 (SAG), Salivary alpha amylase (SAA), Secretory leukocyte protease inhibitor (SLPI), Sodium; myo-inositol cotransporter (SMIT), Superoxide dismutase 1 Cu/Zn (SOD1), Superoxide dismutase 2 Mn (SOD2), Superoxide dismutase 3 Extracellular (SODS), Substance P (SP), Substance P (Neurokinin 1) receptor (NKR), Serotonin Receptor 1A (SR1), Serotonin Receptor 2A (SR2), Turin transporter (TauT), Tumor Growth Factor beta 1, 2, 3 (TGF), Toll-like receptor 2 (TLR2), Toll-like receptor 3 (TLR3), Toil-like receptor 4 (TLR4), Toll-like receptor 7 (TLR7), Toll-like receptor 8 (TLR8), Trehalase neutral (TRE), Ubiquitin (UB), Urotensin II (UT), Vascular adhesion molecule-1 (VCAM1), Vascular endothelial growth factor C (VEGF-C), VEGF receptor 1 (VEGFR-1, Flt-1) (VEGFR), Vasointestinal peptide (VIP), Vimentin (Vim) or a combination thereof. In one aspect, the method includes at least one stress biomarker associated with dehydration. In an additional aspect, dehydration is hypertonic dehydration, isotonic dehydration or hypotonic dehydration. In certain aspects, the at least one stress biomarker associated with dehydration comprises Acidic Trehalase-like protein 1 (ATHL), Osmotic stress protein 94 (OSP94), Sodium/myo-inositol cotransporter (SNIFF) or a combination thereof. In another aspect, the method includes at least one stress biomarker associated with AIDS progression (unsuppressed HIV) and/or acute HIV. In certain aspects, the at least one stress biomarker associated with AIDS progression (unsuppressed HIV) and/or acute HIV comprises Bone Marrow Stromal Cell Antigen 2 (BST2), Salivary Agglutinin gp340 (SAG), Vascular endothelial growth factor C (VEGF-C) or a combination thereof. In a further aspect, the method includes at least one stress biomarker associated with heart disease. In an additional aspect, heart disease is acute heart failure (AHF) with preserved ejection fraction (HF-pEF), acute heart failure (AHF) with restricted ejection fraction (HF-rEF) or atrial (AFIB). In certain aspects, the at least one stress biomarker associated with heart disease comprises Cyclooxygenase 2 (Cox-2). Epidermal growth factor receptor (EGFR), Leptin, MAP kinase Mek-1 or a combination thereof. In one aspect, the method includes at least one stress biomarker associated with traumatic brain injury (FBI), in an additional aspect, traumatic brain injury is mild TBI (mTBI, concussion), severe TBI (sTBI) or neurocognitive disorder (NCD) due to TBI (NCDT). In certain aspects, the at least one stress biomarker associated with neurocognitive disorder (NCD) due to TBI (NCDT) comprises Cytochrome P450 Reductase (CYPOR), Natriuretic peptide receptor A (NPR), Oxytocin receptor (OTR) or a combination thereof.

In another aspect, the method includes at least one stress biomarker associated with post-traumatic stress disorder (PTSD). In an additional aspect, the method includes at least one stress biomarker associated with kidney disease, including chronic kidney disease (CKD and acute kidney injury (AKI). In certain aspects, the at least one stress biomarker associated with kidney disease comprises Annexin 5 (Annex), Nuclear factor of activated T cells 5 (NFAT5, TonEBP), Osmotic stress protein 94 (OSP94) or a combination thereof.

In some embodiments, the levels of the at least one biomarker are detected by analysis of biomarker protein or nucleic acid in the sample comprising the salivary cells. In particular embodiments, the analysis of biomarker protein includes detection with an antibody. In one aspect, the salivary cells are lysed prior to analysis with the antibody. The analysis may be conducted by ELISA or other antibody detection methods known in the art, in certain embodiments, the levels of the at least one biomarker are assayed using a device of the invention. In some embodiments, the sample containing the salivary cells is analyzed on microscope slide. In one embodiment, the sample is whole saliva.

In other embodiments, the analysis of biomarker nucleic acid comprises isolation of salivary cell nucleic acid. In one aspect, the biomarker nucleic acid is detected in the isolated salivary cell nucleic acid by nucleic acid hybridization or PCR amplification.

In another embodiment of the invention there are provided methods of processing a salivary cell sample for biomarker analysis. Such methods include applying a sample of saliva or salivary cells to a substrate; fixing the cells; incubating the cells in low pH citrate buffer at 37° C.; contacting the cells with serum; applying a primary antibody for each of biomarker of a biomarker panel; and detecting the binding of the primary antibody using a secondary antibody having a detectable label, wherein the label is detected optically using a computerized image analysis. In certain embodiments, the salivary cells are collected using an oral brush. In some embodiments, the biomarker panel comprises at least one biomarker selected from the group consisting of Acidic Trehalase-like protein 1 (ATHL), Adrenocorticotropic hormone (ACTH), Aldose Reductase (ALR), ALG-2 interacting protein X (Alix), Annexin 5 (Annex), Apolipoprotein B mRNA editing enzyme APOBEC 3G (APO), Aquaporin 5 (AQP5), Betaine-GABA transporter 1 (BGT), Bone Marrow Stromal Cell Antigen 2 (BST2, Tetherin), Caspase 3 (Casp3), Caspase 8 (Casp8), CD63 (CD63, Tetraspanin, LAMP-3), CD9, Cyclin D1 (Cyclin), Cyclooxygenase-2 (Cox-2), Cytochrome P450 2E1 (CY P450), Cytochrome P450 Reductase (CYPOR), Human beta defensing 2 (HBD2,) Human beta defensin 3 (HBD3), Human beta defensin 4 (HBD4), DICER, Epidermal growth factor receptor (EGER), Ferritin (Fer), Fos (Fos), Furin convertase (Furin, PACE), Glucocorticoid receptor (OR), Glucose regulated protein 58 (Grp58), Glucose regulated protein 75 (Grp75, Mortalin), Gluthathione S transferase pi (GSTp), Heat shock protein 27 (HSP27), Heat shock protein 40 (HSP40). Heat shock protein 60 (HSP60), Heat shock protein 70 (HSP70), Heat shock protein 90 (HSP90), Heat shock protein transcription factor 1 (HSF1), Herne oxygenase 1 Histone 3 methyltransferase SUV39H (HAT), Histone deacetylase 1 (HDAC), Hyperosmotic glycerol response 1 (p38) (HOG), Hypoxia-induced factor alpha 1 (HIF1), Integrin B1 (INTb), Interleukin-1 beta (IL-1), IL-6 (IL-6), IL-8 (IL-8), IL-10 (IL-10), IL-12 beta (IL-12), Intracellular adhesion molecule-1 (ICAM1, CD54), Jun (Jun), Leptin, Leptin (obesity) receptor (ObR), Lysosome-associated membrane glycoprotein-1 (LAMP-2), MAP kinase p38 (p38), MAP kinase Mek-1, mitogen activated (MEK1), MAP kinase. Mekk-1, stress activated (MEKK1), MAP kinase Jnk1/2, stress activated protein kinase (SAPK), Mammalian target of rapamycin (mTOR), Matrix metalloproteinase 9 (MMP9), Metallothionein (MT), Microtubule-associated protein light chain 3 β (MAP-LC3β, LC3), Mucin 1 (Muc1), Myeloperoxidase (MPO), Natriuretic peptide B (BNP), Natriuretic peptide receptor A (NPR), Neutrophil gelatinase-associated lipocalin 1 (NGAL), Neuropathy target esterase (NTE), Nitric oxide synthase, neuronal nNOS (NOS1). Nitric oxide synthase, inducible iNOS (NOS2), Nuclear factor of activated T cells 5 (NFAT5, TonEBP), Ornithine decarboxylase (ODC), Osmotic stress protein 94 (OSP94), Oxytocin receptor (OTR), Pro-opiomelanocortin/beta-endorphin (POMC), p53 tumor suppressor (p53), Peripheral benzodiazepine receptor (PBR), Salivary Agglutinin gp340 (SAG), Salivary alpha amylase (SAA), Secretory leukocyte protease inhibitor (SLPI), Sodium/myo-inositol cotransporter (SMIT), Superoxide dismutase 1 Cu/Zn (SOD1), Superoxide dismutase 2 Mn (SOD2), Superoxide dismutase 3 Extracellular (SOD3), Substance P (SP), Substance P (Neurokinin 1) receptor (NKR), Serotonin Receptor 1A (SR1), Serotonin Receptor 2A (SR2), Taurin transporter (TauT), Tumor Growth Factor beta 1, 2, 3 (TGF), Toll-like receptor 2 (TLR2), Toll-like receptor 3 (TLR3), Toll-like receptor 4 (TLR4), Toll-like receptor 7 (TLR7), Toll-like receptor 8 (TLR8), Trehalase neutral (TRE), Ubiquitin (UB), Urotensin II (UT), Vascular adhesion molecule-1 (VCAM1), Vascular endothelial growth factor C (VEGF-C), VEGF receptor 1 (VEGFR-1. Flt-1) (VEGFR), Vasointestinal peptide (VIP), Vimentin (Vim) or a combination thereof.

In another embodiment of the invention, there are provided methods for constructing a biomarker panel for detecting a stress response in a cultured cell. The method includes detecting the level of one or more biomarkers from a panel of biomarkers in cultured cells subjected to a treatment that induces cellular stress; and comparing the level of the biomarkers from the treated cells to the level of the biomarker from a corresponding sample of cultured cells that have not been subjected to the treatment that induces cellular stress, wherein biomarkers having a difference level in the treated cells as compared to the untreated cells are included in an SR biomarker panel for a stress response. In particular embodiments, the treatment that induces cellular stress is a stressor selected from the group consisting of heat shock, freeze/thaw cycling, hypersalinity, dehydration, and oxidative stress. In some embodiments, the cultured cells are salivary cells, peripheral blood mononuclear cells, or cells from organ cultures of tonsil, skin, gut or lung. In particular embodiments, the cells are animal cells. In one aspect, the cells are human cells.

In one embodiment, the present invention provides a method for detecting a condition or disorder associated with a stress response in a subject comprising detecting an altered level of at least one biomarkers in an stress response biomarker panel in a sample comprising salivary cells from a subject, as compared to a corresponding sample from a normal subject, wherein the panel comprises at least two biomarkers, and wherein further an alteration in the level of biomarker is indicative of a stress response associated with the condition or disorder, wherein the altered levels of the at least one or more biomarkers are detected using a device of claim 1, thereby detecting the condition or disorder in the subject.

In one aspect, the at least one biomarker selected from the group consisting of Acidic Trehalase-like protein 1 (ATHL), Adrenocorticotropic hormone (ACTH), Aldose Reductase (ALR), ALG-2 interacting protein X (Mix), Annexin 5 (Annex), Apolipoprotein B mRNA editing enzyme APOBEC 3G (APO), Aquaporin 5 (AQP5), Betaine-GABA transporter 1 (BGT), Bone Marrow Stromal. Cell Antigen 2 (BST2, Tetherin), Caspase 3 (Casp3), Caspase 8 (Casp8), CD63 (CD63, Tetraspanin, LAMP-3), CD9, Cyclin D1 (Cyclin), Cyclooxygenase-2 (Cox-2), Cytochrome P450 2E1 (CYP450), Cytochrome P450 Reductase (CYPOR), Human beta defensing 2 (HBD2,) Human beta defensin 3 (HBD3), Human beta defensin 4 (HBD4), DICER, Epidermal growth factor receptor (EGFR), Ferritin (Fer), Fos (Fos), Furin convertase (Furin, PACE), Glucocorticoid receptor (GR), Glucose regulated protein 58 (Grp58), Glucose regulated protein 75 (Grp75, Mortalin), Gluthathione S transferase pi (GSTp), Heat shock protein 27 (HSP27), Heat shock protein 40 (HSP40), Heat shock protein 60 (HSP60), Heat shock protein 70 (HSP70), Heat shock protein 90 (HSP90), Heat shock protein transcription factor 1 (HSF1), Heme oxygenase 1 (HO-1), Histone 3 methyltransferase SUV3914 (HAT), Histone deacetylase 1 (HDAC), Hyperosmotic glycerol response 1 (p38) (HOG), Hypoxia-induced factor alpha 1 (HW1). Integrin B (INTb). Interleukin-1 beta (IL-1), IL-6 (IL-6), IL-8 (IL-8), IL-10 (IL-10 IL-12 beta (IL-12), Intracellular adhesion molecule-1 (ICAM1, CD54), Jun (Jun), Leptin, Leptin (obesity) receptor (ObR), Lysosome-associated membrane glycoprotein-1 (LAMP-2), MAP kinase p38 (p38), MAP kinase Mek-1, mitogen activated (MEK1), MAP Linage Mekk-1, stress activated (MEKK1), MAP kinase Jnk1/2, stress activated protein kinase (SAPK). Mammalian target of rapamycin (mTOR), Matrix metalloproteinase 9 (MMP9), Metallothionein (MT), Microtubule-associated protein light chain 3 β (MAP-LC3β, LC3), Mucin 1 (Muc1), Myeloperoxidase (MPO), Natriuretic peptide B (BNP), Natriuretic peptide receptor A (NPR), Neutrophil gelatinase-associated lipocalin 1 (NGAL), Neuropathy target esterase (NTE), Nitric oxide synthase, neuronal nNOS (NOS1), Nitric oxide synthase, inducible iNOS (NOS2), Nuclear factor of activated T cells 5 (NFAT5, TonEBP), Ornithine decarboxylase (ODC), Osmotic stress protein 94 (OSP94), Oxytocin receptor (OTR), Pro-opiomelanocortin/beta-endorphin (POMC), p53 tumor suppressor (p53), Peripheral benzodiazepine receptor (PBR), Salivary Agglutinin gp340 (SAG), Salivary alpha amylase (SAA), Secretory leukocyte protease inhibitor (SLPI), Sodium/myo-inositol cotransporter (SMIT), Superoxide dismutase 1 CU/Zn (SOD1), Superoxide dismutase 2 Mn (SOD2), Superoxide dismutase 3 Extracellular (SOD3). Substance P (SP), Substance P (Neurokinin 1) receptor (NKR), Serotonin Receptor 1A (SR1), Serotonin Receptor 2A (SR2), Taurin transporter (TauT), Tumor Growth Factor beta 1, 2, 3 (TGF), Toll-like receptor 2 (TLR2), Toll-like receptor 3 (TLR3). Toll-like receptor 4 (TLR4), Toll-like receptor 7 (TLR7), Toll-like receptor 8 (TLR8), Trehalase neutral (TRE), B), Ubiquitin II (UT), Vascular adhesion molecule-1 (VCAM1), Vascular endothelial growth factor C (VEGF-C), VEGF receptor 1 (VEGFR-1, Flt-1) (VEGFR), Vasointestinal peptide (VIP), Vimentin (Vim) or a combination thereof.

In another aspect, the condition or disorder associated with a stress response is dehydration, AIDS progression (unsuppressed HIV), acute HIV, traumatic brain injury (TBI), post-traumatic stress disorder, heart disease or kidney disease. In an additional aspect, dehydration is hypertonic dehydration, isotonic dehydration or hypotonic dehydration. In certain aspects, the at least one stress biomarker associated with dehydration comprises Acidic Trehalase-like protein 1 (ATHL), Osmotic stress protein 94 (OSP94), Sodium/ myo-inositol cotransporter (SMIT) or a combination thereof. In a further aspect, the at least one stress biomarker associated with AIDS progression (unsuppressed WV) and/or acute HIV comprises Bone Marrow Stromal Cell Antigen 2 (BST2), Salivary Agglutinin gp340 (SAG), Vascular endothelial growth factor C (VEGF-C) or a combination thereof. In one aspect, heart disease is acute heart failure (AHF) with preserved ejection fraction (HF-pEF), acute heart failure (AHF) with restricted ejection fraction (HF-rEF) or atrial fibrillation (AFIB). In another aspect the at least one stress biomarker associated with heart disease comprises Cyclooxygenase-2 (Cox-2), Epidermal growth factor receptor (EGFR), Leptin, MAP kinase Mek-1 or a combination thereof. In an additional aspect, traumatic brain injury is mild TBI (mTBI, concussion), severe TBI (sTBI) or neurocognitive disorder (NCD) due to TBI (NCDT). In a further aspect, the at least one stress biomarker associated with neurocognitive disorder (NCD) due to TBI (NCDT) comprises Cytochrome P450 Reductase (CYPOR), Natriuretic peptide receptor A (NPR). Oxytocin receptor (OTR) or a combination thereof. In another aspect, kidney disease is chronic kidney disease (CKD) or acute kidney injury (AKI). In an additional aspect, the at least one stress biomarker associated with kidney disease comprises Annexin 5 (Annex), Nuclear factor of activated T cells 5 (NFAT5, TonEBP), Osmotic stress protein 94 (OSP94) or a combination thereof.

BRIEF DESCRIPTION OF THE DRAWINGS

FIG. 3A. N pool, normal saliva from 3 donors. S pool, cells combined after treatment by desiccation, hypersalinity, heat shock, oxidative stress and freeze/thaw shock. FIG. 3C. Salivary cells from a healthy donor. FIG. 3D. Saliva from the same donor during post-traumatic physiological stress. FIG. 3E. Saliva after exposure to cellular stress. FIG. 3F. Saliva after exposure to cellular stress. FIG. 3G. EMA, positive control staining of a cytoplasmic protein in salivary epithelial cells. FIG. 3H. NC, a negative staining control.

FIG. 7A shows images of multi-SRP staining of saliva FIG. 7B shows a plot of the SRP score calculated as the ratio between the average staining intensity across 900 saliva cells, and the maximum staining intensity value for saliva cells.

FIG. 8A. Acute 4% hypertonic dehydration. FIG. 8B. Chronic (12 hrs) 4% hypertonic dehydration. FIG. 8C. Dehydration and concussion. The pathways are 1—Redox, 2—Osmotic stress, 3—Cellular detox. 4—Chaperoning, 5—DNA, 6—Adhesion, 7—Cell cycle, 8—Apoptosis, 9—Signaling, 10—Immunity, 11—Microbiome.

FIG. 9A. Images of 1× to 40× concentrated saliva stained for Mucin 1 (magnification ×200). FIG. 9B. Standard calibration curve for the Mucin1 IHC assay.

FIG. 11 is a table showing candidate biomarkers of dehydration. Diagnostic accuracy was calculated as the percent AUC value from ROC curve analysis. Diagnostic accuracy values ≥80% are bolded. DEH, dehydration. REH, rehydration. EUH, euhydration.

FIG. 12A. The dehydration and SRP pathways associated with 80 SRP biomarkers. FIG. 12B. SRP pathways involved in acute dehydration, chronic dehydration and dehydration and concussion.

FIGS. 13A-13C show the diagnostic accuracy, specificity and sensitivity was determined tier different types and levels of dehydration. FIG. 13A. Hypertonic dehydration (2% and 4%) isotonic dehydration, comb dehydration (hypertonic and isotonic), rehydration and control. FIG. 13B. Gender effect and daily and diurnal variability. FIG. 13C. Comparison of diagnostic accuracy between biomarkers and standard indicators.

FIG. 15A. The HIV/AIDS and SRP pathways associated with the 100 SRP biomarkers. FIG. 15B. Suppressed HIV and unsuppressed FIG. 15C. Acute HIV and STD. The pathways are 1) Redox; 2) Detox; 3) Chaperoning; 4) DNA; 5) Adhesion; 6) Cell cycle/energy; 7) Apoptosis; 8) Signaling; 9) Immunity and 10) Microbiome.

FIG. 16 shows the markers for unsuppressed HIV.

FIG. 17A. The TBI/NCDT pathways and SRP pathways and 100 SRP biomarkers, Normalized. Pathway activation index (0-10) was calculated from biomarker data using a patented algorithm. FIG. 17B. Acute TBI. FIG. 17C. Acute dehydration, FIG. 17D. HF-pEF (heart failure with preserved ejection fraction). FIG. 17E. Acute HIV, FIG. 17F. Chronic NCD due to TBI. FIG. 17G. Chronic dehydration. FIG. 17H. HF-rEF (heart failure with reduced ejection fraction). FIG. 17I. Chronic HIV/AIDS. The arrow indicates the top activated pathway in each disease. The SRP pathways: 1—Oxidative stress, 2—Detoxification, 3—Chaperoning, 4—DNA, 5—Adhesion/Cytoskeleton, 6—Cell cycle, 7—Apoptosis, 8—Signaling, 9—Immunity, 10—Microbiome.

Figure 18A:
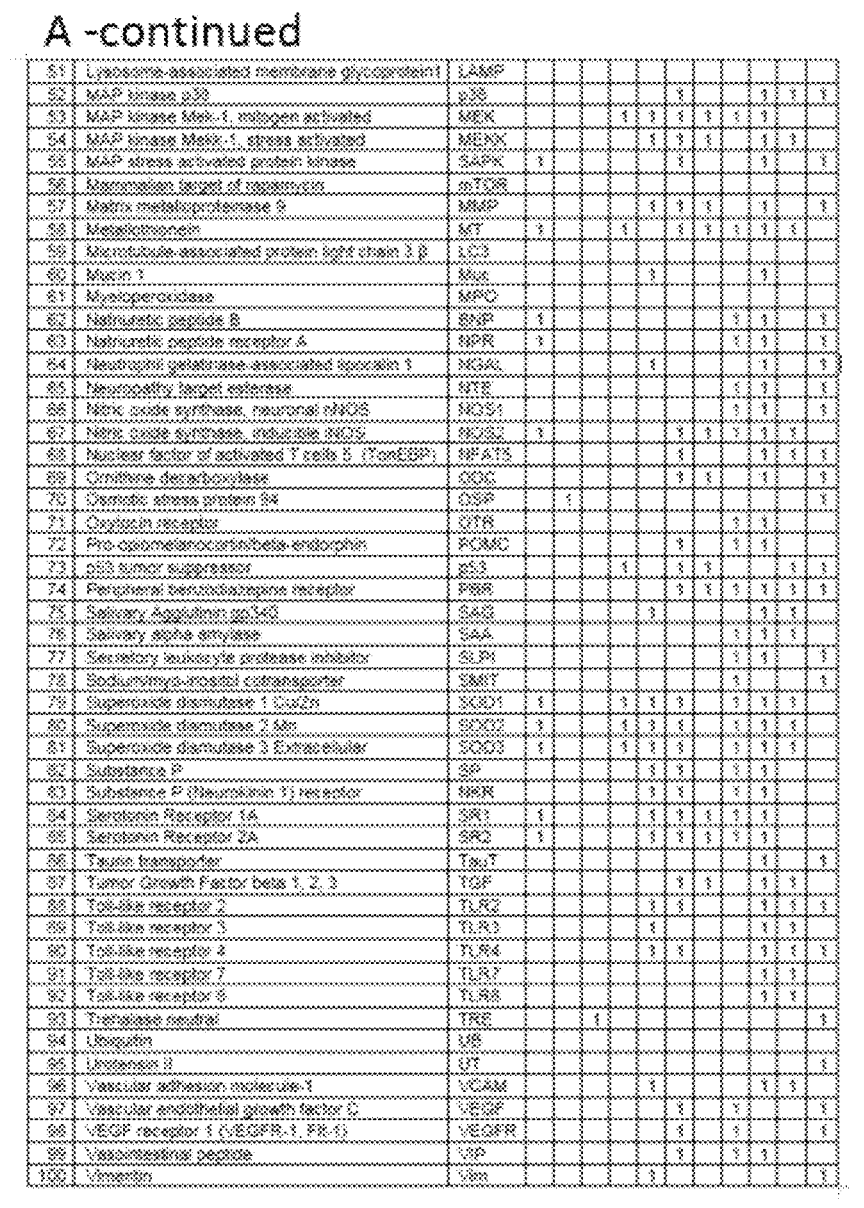

FIGS. 18A-18B are a table of Stress Response Profiling (SRP) biomarkers and the associated SRP pathways. FIG. 18A. Specific biomarkers associated with pathways. The pathways are 1) Redox stress response; 2) Cellular detoxification; 3) Protein chaperoning; 4) DNA repair and modification; 5) Cell adhesion, cytoskeleton, exosomes; 6) Cell cycle & energy metabolism; 7) Apoptosis and autophagy; 8) Neuroendocrine signaling; 9) Innate and specific immunity; 10) Microbiome stress response and 11) Microbiome stress response. FIG. 18B. SRP pathways and a heat map for SRP biomarkers.

FIGS. 19A-19B are tables showing candidate saliva biomarkers for diagnostics of heart disease and kidney disease. FIG. 19A. Saliva biomarkers for diagnostics of AHF, HF-pEF, HF-rEF and AFIB. FIG. 19B. Saliva biomarkers for diagnostics of AKI and CKD. Diagnostic accuracy was calculated as the percent AUC value front ROC curve analysis. Key: AHF, Acute Heart Failure; AFIB, Atrial Fibrillation; AKI, Acute Kidney Injury; CDK, Chronic Kidney Disease. EF, Ejection Fraction; HF-pEF, Heart Failure with preserved EF; HF-rEF, Heart Failure with restricted EF.

FIGS. 20A-20C show candidate saliva biomarkers for diagnostics of acute mTBI (concussion) in 2 independent human studies. FIG. 20A. Figure showing OSP94 and Vimentin biomarkers are strongly upregulated in whole saliva from mTBI patients relative to healthy controls in Study 1. FIG. 20B. Table showing fold increase in 75 SRP biomarkers in mTBI saliva relative to healthy controls in Study 1. FIG. 20C. Table showing fold increase in 50 SRP biomarkers in mTBI saliva relative to healthy controls in Study 2.

DETAILED DESCRIPTION OF THE INVENTION

Figure 1:
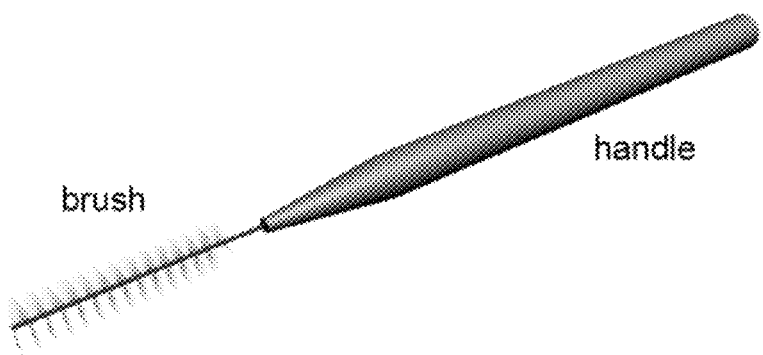
FIG. 1 shows an illustration of device for collecting saliva samples.

The present invention relates to devices and methods for detecting a stress response in a sample. The present invention also relates to determining and detecting levels of biomarkers in a sample.

Biological responses to stressors involve hundreds of highly integrated molecular pathways. However, to practically analyze chronic stress, a small number of "universal pathways" have been identified that reproducibly respond to most stressors in most organisms, and in particular, essentially all vertebrates. Functional activation of these universal pathways by stressors generates reproducible patterns of data that can be monitored to analyze the characteristics and effects of chronic stress.

The methods described herein are referred to as "stress response profiling" or "SR profiling," because they relate to the measurement of the levels of multiple SR biomarkers by performing SR biomarker assays, where the SR biomarkers are associated with multiple stress response pathways that are reproducibly activated by chronic stress (i.e., the universal SR pathways.) The results of such multi-dimensional SR biomarker assays can be used to construct a "profile" (i.e. a pattern of data, which is also referred to in the industry as a "signature" or a "fingerprint") that is characteristic of the type of stress, the organism and/or the sample type.

Stressors can trigger persistent perturbations of homeostasis, i.e., they cause chronic stress. Biological responses to chronic stress (also referred to as "adaptive stress responses") can be categorized in terms of the SR pathways they activate, which are further characterized in terms of the SR biomarkers associated with these pathways. Thus, SR profiling of either or both the SR pathway activation or the SR biomarker levels resulting from such activation can be utilized to provide molecular signatures of biological responses to stressors that threaten health, such as stressors that cause chronic s SR profiling is therefore useful, in part, to predict increased risk of disease.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

With respect to ranges of values, the invention encompasses each intervening value the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed.

1. SRP Technology

Stress Response Profiling (SRP) is a recently developed technology that uses molecular biomarkers for multiparametric measurements of physiological stress responses. The SRP measurement serves as a novel vital sign. SRP is applicable to a broad spectrum of health threats including environmental stressors, metabolic stressors, psychological trauma, injuries and diseases. SRP measurements quantify physiological stress and also discriminate between different types of health disorders, SRP biomarkers monitor ten principal homeostatic processes (Table 1).

As used herein, the term "universal stress response pathway" or simply "SR pathway" is to be understood as a form of stress response to most stressors, in most organisms. Functional activation of these. SR pathways generates reproducible patterns of expressed molecules.

As used herein, the term "SR biomarker" is to be understood as an expressed molecule known to be or suspected of being associated with activation of a SR pathway.

As used herein, the term "SR biomarker profile" is a multi-dimensional pattern of data whose components are at

TABLE 1

SR Biomarkers Monitor Ten Principal Cellular Stress Responses

SR biomarkers

| SR | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| 1 |   |   | + | + |   | + | + | + | + | +  | +  | +  | +  |    |    | +  | +  | +  |    | +  |    |    |    |    | +  |
| 2 |   |   |   | + |   |   |   | + | + |    | +  | +  |    | +  |    |    | +  | +  |    |    |    |    |    |    | +  |
| 3 |   |   |   |   |   |   |   | + | + |    |    | +  | +  | +  | +  | +  | +  |    |    | +  |    |    |    |    |    |
| 4 |   | + | + |   | + |   |   |   | + |    |    |    |    |    |    | +  | +  |    |    |    |    |    |    |    |    |
| 5 |   |   |   |   |   | + |   |   |   |    |    |    |    |    |    | +  | +  |    |    | +  |    | +  | +  | +  | +  |
| 6 | + |   | + | + | + | + | + | + | + | +  | +  | +  | +  | +  | +  | +  | +  | +  | +  | +  | +  | +  | +  | +  | +  |
| 7 |   | + | + | + | + |   | + | + | + |    |    | +  | +  |    |    | +  | +  | +  |    |    |    |    |    |    |    |
| 8 | + |   | + |   |   | + | + | + |   | +  |    | +  | +  | +  |    | +  |    | +  | +  |    |    | +  | +  | +  | +  |
| 9 | + | + |   | + |   | + | + | + | + |    | +  | +  | +  | +  | +  | +  | +  | +  | +  | +  | +  | +  | +  | +  | +  |
| 10|   |   |   |   |   |   |   |   |   |    | +  |    |    |    |    | +  |    |    |    |    |    | +  | +  |    |    |

| SR | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|
| 1 |    | +  |    |    | +  | +  |    |    |    | +  |    | +  | +  |    |    |
| 2 |    |    |    |    | +  |    |    |    |    |    |    |    |    |    |    |
| 3 |    |    |    |    |    |    |    |    |    |    |    |    |    |    |    |
| 4 |    | +  |    |    |    |    |    |    |    |    | +  | +  |    | +  |    |
| 5 |    |    |    | +  |    | +  |    | +  |    | +  | +  | +  |    |    |    |
| 6 | +  | +  | +  | +  | +  | +  | +  | +  | +  | +  | +  | +  | +  | +  | +  |
| 7 | +  | +  |    | +  | +  | +  | +  | +  | +  |    |    |    | +  | +  |    |
| 8 | +  | +  |    |    | +  | +  | +  | +  | +  | +  | +  |    |    |    | +  |
| 9 | +  | +  |    | +  | +  | +  | +  | +  | +  | +  | +  | +  | +  |    | +  |
| 10|    | +  |    |    |    | +  |    |    |    |    | +  | +  | +  | +  |    |

SRP biomarkers 1-40: beta-endorphin, caspase 8, cyclin D, Cox-2, CYP450, cytochrome c, EGFR, ferritin, glucocorticoid receptor, Grp58, Grp75, GSTp, Hsp25/27, Hsp40, Hsp60, Hsp70, Hsp90, HSF1, HO-1, IL-1 beta, IL-6, IL-8, IL-10, laminin, leptin receptor, metallothionein, Mekk-1, Mek-1, NADPH-CYP450 reductase, iNOS, Fos, Jun, serotonin receptor, serotonin, Substance P, SOD Mn, SOD Cu/Zn, TGFbeta, p53, vasoactive intestinal peptide.
SR, stress responses 1-10; redox control, cellular detoxification Phase I and II, chaperoning, DNA repair, cellular adhesion and motility, cell growth and energy metabolism, apoptosis, neuro-endocrine signaling, immunological activation, microbial activation.

As used herein, the term "homeostasis" is a biological process that maintains the health of organisms.

As used herein, the term "persistent homeostatic perturbation" is to be understood as a homeostatic change that has an adverse effect on the health of organisms. It is another way of referring to "chronic stress" or simply "stressed" which should be understood to mean a persistent perturbation of homeostasis and encompassing all forms of chrome cellular stress and chronic physiological stress.

As used herein, the term "stressor" is to be understood as all thrills of agents or conditions that give rise to stress. Stressors according to the present invention include agents and conditions that are in the outer environment of organisms such as the air temperature as well as agents and conditions that are in the inner environment of organisms such as a disease.

As used herein, the term "adaptive stress response" or simply "stress response" is to be understood as a homeostatic process that provides a countermeasure to stress.

As used herein, the term "stress response pathway" is to be understood as the form of the stress response that has a specific function in the organism, such as DNA repair. Stress response pathways are embodied in expressed molecules (i.e., SR biomarkers.)

least two SR biomarker scores for individual SR biomarkers across a SR biomarker panel.

As used herein, the terms "SR pathway profile" and "SRP" are a multi-dimensional pattern of data representing at least two SR pathways. The components are functions of SR biomarker scores related to the individual SR pathways. The functions yield one-dimensional data points that provide simple-to-use indices of activation levels for the individual pathways.

As used herein, the term "stress response profiling" refers to constructing either or both SR pathway profiles or SR biomarker profiles from SR biomarker assays.

As used herein, the term "SR biomarker panel" is to be understood as at least two SR biomarkers that as a group provide enhanced information about stress responses than single SR biomarkers.

As used herein, the term "SR biomarker panel score" or "panel score" is to be understood as a one-dimensional data point calculated as the average of SR biomarker scores across a SR biomarker panel.

As used herein, the term "SR biomarker score" is to be understood as a normalized and optionally log-transformed measurement of a SR biomarker.

As used herein, the term "measurement" of a SR biomarker is to be understood as a quantitative or qualitative determination of the SR biomarker's expression level in a sample from an organism.

As used herein, the term "individual SR biomarker assay" or "SR biomarker assay" is to be understood as an assay of individual SR biomarkers.

As used herein, the term "combined SR biomarker assay" is to be understood as an assay that yields measurements representative of the combined expression levels for a panel of SR biomarkers.

The homeostatic processes monitored by SRP biomarkers regulate general stress responses, basic body functions and physical vital signs (body temperature, heart rate FIR, blood pressure BP, respiratory rate). These homeostatic processes include redox control, cellular detoxification, chaperoning, DNA repair, cellular adhesion and cell growth, apoptosis, neuron-endocrine signaling, immunity, microbial activation and osmotic stress.

Redox Control (1). This pathway regulates levels of reactive oxygen and nitrogen species (superoxide, nitric oxide, carbon monoxide) through free radical scavenging proteins such as superoxide dismutases. Free radicals are essential cellular mediators but when in excess, they cause cellular dysfunction through damaging lipids, proteins, DNA and membrane integrity.

Cellular Detoxification (2). Cellular detoxification provides a defense against chemical threats to cellular integrity. Phase I detoxification is a cytochrome P450 driven process for metabolizing a wide variety of endogenous metabolites (e.g., fatty acids, steroids) and foreign substances (drugs, alcohol, pesticides and hydrocarbons). Phase II is based on the glutathione metabolism and provides cellular resistance to oxidants, hydrocarbons and heavy metals.

Chaperoning (3). Chaperones fold newly synthesized polypeptides and denatured proteins and for prevent uncontrolled protein aggregation. Chaperoning involves hundreds of "client" proteins and therefore has a key role in multiple biological functions including cellular protection, metabolism, growth, the development of multicellular organisms and molecular evolution. Excessive chaperoning facilitates disease by folding "wrong" clients such as the diphtheria toxin or mutant p53 that are cytotoxic or cause cancer.

DNA Repair (4). DNA damage is ubiquitous and therefore the stability of the genome is under a continuous surveillance by multiple DNA repair mechanisms. DNA lesions are produced during transcription and replication, and by metabolic and immunity by-products (e.g., free radicals produced during aerobic respiration and by immune cells killing bacteria). DNA can be also damaged by environmental mutagens such as oxidants, heavy metals, radiation and viruses. The DNA repair pathway regulates multiple stages and mechanisms of DNA repair, and is closely linked with cell cycle control and apoptosis.

Cellular Adhesion and Motility (5). This pathway monitors cellular interactions with the extracellular matrix and also changes in cytoskeletal matrix such as centrioles, kinetosomes and other microtubule organizing centers. These processes are essential for cellular survival, growth, metabolism and motility, and also for the formation of microbial biofilms and microbial-host interactions.

Cell Growth (6). In multicellular organisms, cell cycle progression is strongly regulated during the development and modulated by growth factors (mitogens), disease and environmental stress. In mature tissues, most cells do not divide. Cycling cells in tissues are typically somatic stem cells involved in normal tissue turnover (e.g., the germinal layer of the skin). Cell cycling is typically arrested in starved cells and in cells with DNA or mitochondrial damage. Increased cell growth occurs during immune responses, wound healing and regeneration of tissues damaged by environmental stress, toxins, disease or infection. Uncontrolled, excessive cell growth is found in cancer.

Cell Death (7). The programmed cell death (apoptosis) "recycles" cellular components and prevents the release of toxins from dying cells, as happens during necrotic cell death. In animal tissues, apoptosis is increased in areas of tissue remodeling and wound healing, and during aging. During a disease, apoptosis can be increased within the diseased tissue (e.g., psoriatic skin lesions) and/or in remote tissues and biofluids (e.g., HIV Tat protein is a soluble mediator that triggers apoptosis in uninfected lymphocytes). Apoptosis can be also triggered by environmental stressors that cause mitochondrial damage (e.g., oxidative stress and uv light).

Neuro-Endocrine Signaling (8). This pathway is crucial for regulating physiological homeostasis and behavioral regulation in animals including simple invertebrates. It involves a large number of mediators (hormones, neuropeptides, neurotransmitters) and cellular receptors produced by specialized tissues (glands and neural tissues), and also locally in peripheral tissues (e.g., skin and gut). In vertebrates, two signaling mechanisms provide initial responses to stress: the limbic hypothalamic-pituitary-adrenal (LHPA) axis that involves glucocorticoids (e.g., Cortisol) and the sympathetic nervous system activation via catecholamines. However, chronic stress also activates signaling of pain and anxiety, energy balance, metabolism, respiration, circulation and reproduction. Neuro-endocrine and immune signaling are integrated through common mediators and provide coordinated responses to environmental stress and disease.

Immunity (9). Immunity provides a systemic defense against biological threats to organism's integrity such as injuries, tumors and disease-causing microorganisms. Innate immunity provides a nonspecific defense through soluble mediators (e.g., chemokines, agglutinins) and specialized cells (e.g., macrophages) that circulate through the organism and inactivate parasitic microorganisms, engulf apoptotic cell debris and kill infected and tumor cells. Innate immunity is found in protists, animals and plants, Vertebrates use innate immunity during the initial phases of stress response because it takes several days to activate specific immunity that provides threat specific antibodies and lymphoid cells immune regulation is mediated through numerous signaling proteins called cytokines or interleukins. Increased immunity can be beneficial (e.g., short-term immune activation that removes a bacterial infection) or harmful (chronic inflammation and autoimmunity increase physiological stress through oxidative stress and apoptosis).

Microbial Activation (10). This pathway monitors the activation of stress responses in microorganisms (bacteria, fungi, viruses), and signaling between microorganisms and host cells. Commensal microbial biofilms are an integral part of animal and plant bodies and contribute to physiological homeostasis. In animals, microbial biofilms are primarily associated with the inner and the outer body surfaces (the mucosal epithelium and the skin). Therefore microbial biofilms are sensitive both to environmental stressors (e.g., uv light) as well as to micro-environmental conditions in host tissues and body fluids (e.g., oxidative stress). During physiological stress, increased signaling between microbial biofilms and host cells promotes protection of the organism through modulating host's stress responses. For example, signaling by gastrointestinal microflora modulates levels of proteins with key roles in redox control, cellular detoxification, chaperoning, cell growth, apoptosis and immunity such as metallothionein, Hsp25, ferritin, p53, TGF beta, IL-8 and IL-10. When pathogenic microorganisms invade animals or plants, their stress responses are elevated, which in turn increases stress responses in the host ((bacterial heat shock proteins are animal superantigens). Disease-causing microorganisms also release soluble mediators that trigger cellular stress and activate multiple stress response pathways in infected as well as remote host tissues (e.g., HIV Tat protein).

Osmotic Stress Response (10: This pathway involves the organism's response to sudden change in the solute concentration around a cell, causing a rapid change in the movement of water across its cell membrane. Under conditions of high concentrations of either salts, substrates or any solute in the supernatant, water is drawn out of the cells through osmosis. This also inhibits the transport of substrates and cofactors into the cell thus "shocking" the cell. Alternatively, at low concentrations of solutes, water enters the cell in large amounts, causing it to swell and either burst or undergo apoptosis Stress Response (SR) Biomarkers Activation of SR pathways by stressors results in a pattern of expressed molecules such as genes, proteins, metabolites and lipids, referred to herein as "SR biomarkers. Accordingly, each of these biomarkers is said to be "associated with" one or more SR pathways. Measuring the levels of these SR biomarkers provides useful information about the biological effects of stressors. Preferably, the SR biomarkers are expressed molecules such as proteins or fragments thereof, so long as the fragment is capable of being recognized in an SR biomarker assay with the same sensitivity as the entire protein.

Preferred SR biomarkers and their known associations with SR pathways are listed in Table 2 and FIGS. 16 and 17A-17I. Additional SR Biomarkers and some but not all of their known associations with SR pathways are listed in Table 3 and FIGS. 18A-18B.

TABLE 2

SR Biomarkers
Association with SR Pathways and Expression in Taxonomic Groups of Organisms

| # | SR Biomarker | Abbreviated Name | Expression | | | | | SR. Pathways | | | | | | | | | |
|---|---|---|---|---|---|---|---|---|---|---|---|---|---|---|---|---|---|
| | | | A | B | C | D | E | 1 | 2 | 3 | 4 | 5 | 6 | 7 | 8 | 9 | 10 |
| 1 | Beta-endorphin | Endorphin | + | + | + | | | 0 | 0 | 0 | 0 | 0 | 1 | 0 | 1 | 1 | 0 |
| 2 | Caspase8 | Caspase 8 | + | + | + | | | 0 | 0 | 0 | 1 | 0 | 0 | 1 | 0 | 1 | 0 |
| 3 | Cyclin D1 | Cyclin | + | + | + | | | 0 | 0 | 0 | 1 | 0 | 1 | 1 | 0 | 0 | 0 |
| 4 | Cyclooxygenase 2 | Cox-2 | + | + | | | | 1 | 0 | 0 | 0 | 0 | 1 | 1 | 1 | 1 | 0 |
| 5 | Cytochrome P 450 | CYP450 | + | + | + | + | + | 1 | 1 | 0 | 0 | 0 | 1 | 1 | 0 | 0 | 0 |
| 6 | Cytoplasmic cytochrome c | Cytc | + | + | | | | 0 | 0 | 0 | 1 | 0 | 1 | 1 | 0 | 1 | 0 |
| 7 | Epidermal growth factor receptor | EGFR | + | + | + | | | 1 | 0 | 0 | 0 | 1 | 1 | 1 | 1 | 1 | 0 |
| 8 | Ferritin | Ferritin | + | + | + | + | + | 1 | 0 | 0 | 0 | 0 | 1 | 1 | 1 | 1 | 1 |
| 9 | Glucocorticoid receptor | GR | + | | | | | 1 | 1 | 0 | 0 | 0 | 1 | 1 | 0 | 1 | 0 |
| 10 | Glucose regulated protein Grp58 | Grp58 | + | + | | | | 1 | 1 | 1 | 0 | 0 | 1 | 0 | 0 | 0 | 0 |
| 11 | Glucose regulated protein Grp75 | Grp75 | + | + | + | + | + | 1 | 0 | 1 | 0 | 0 | 1 | 0 | 1 | 1 | 0 |
| 12 | Glutathione-S-transferase p | GST | + | + | + | + | + | 1 | 1 | 0 | 1 | 0 | 1 | 1 | 0 | 1 | 0 |
| 13 | Heat shock protein 25/27 | Hsp25/27 | + | + | + | + | + | 1 | 1 | 1 | 0 | 0 | 1 | 1 | 1 | 1 | 1 |
| 14 | Heat shock protein 40 | Hsp40 | + | + | + | + | + | 0 | 0 | 1 | 0 | 0 | 1 | 0 | 1 | 1 | 0 |
| 15 | Heat shock protein 60 | Hsp60 | + | + | + | + | + | 0 | 1 | 1 | 0 | 0 | 1 | 0 | 1 | 1 | 0 |
| 16 | Heat shock protein 90 | Hsp90 | + | + | + | + | + | 1 | 1 | 1 | 1 | 1 | 1 | 1 | 1 | 1 | 0 |
| 17 | Heat shock transcription factor HSF-1 | HSF-1 | + | + | + | + | + | 1 | 1 | 1 | 0 | 0 | 1 | 1 | 0 | 1 | 0 |
| 18 | Heme oxygenase-1 | HO-1 | + | + | | | | 1 | 0 | 0 | 0 | 0 | 1 | 1 | 1 | 1 | 0 |
| 19 | Interleukin IL-1beta | IL-1 | + | + | | | | 0 | 0 | 0 | 0 | 1 | 1 | 0 | 1 | 1 | 0 |
| 20 | Interleukin IL-6 | IL-6 | + | + | + | | | 1 | 0 | 1 | 0 | 0 | 1 | 0 | 0 | 1 | 0 |
| 21 | Interleukin IL-8 | IL-8 | + | + | | | | 0 | 0 | 0 | 0 | 1 | 1 | 0 | 1 | 1 | 1 |
| 22 | Interleukin IL-10 | IL-10 | + | | | | | 0 | 0 | 0 | 0 | 1 | 1 | 0 | 1 | 1 | 1 |
| 23 | Interleukin IL-12 | IL-12 | + | | | | | 0 | 0 | 0 | 0 | 1 | 1 | 0 | 1 | 1 | 0 |
| 24 | Laminin | Laminin | + | + | | | | 1 | 1 | 0 | 0 | 1 | 1 | 1 | 1 | 1 | 0 |
| 25 | Leptin receptor | ObR | + | | | | | 0 | 0 | 0 | 0 | 0 | 1 | 1 | 1 | 1 | 0 |
| 26 | Metallothionein | MT | + | + | + | + | + | 1 | 0 | 0 | 1 | 0 | 1 | | 1 | 1 | 1 |
| 27 | Stress-activated MAP kinase Mekk-1 | Mekk-1 | + | + | + | + | + | 0 | 0 | 0 | 0 | 1 | 1 | | 0 | 1 | 1 |
| 28 | Mitogen activated MAP kinase Mek-1 | Mek-1 | + | + | + | + | + | 0 | 0 | 0 | 1 | 1 | 1 | | 1 | 1 | 0 |
| 29 | NADPH-cytochrome P 450 reductase | CYP red | + | + | + | | + | 1 | 1 | 0 | 0 | 1 | 1 | | 1 | 1 | 0 |
| 30 | Nitric oxide synthase II, inducible | iNOS | + | + | | | + | 1 | 0 | 0 | 0 | 0 | 1 | 1 | 1 | 1 | 1 |
| 31 | Proto-oncogene c-Fos protein | Fos | + | + | + | | | 0 | 0 | 0 | in | 1 | 1 | 1 | 1 | 1 | 0 |
| 32 | Proto-oncogene c-Jun protein | Jun | + | + | + | | + | 0 | 0 | 0 | in | 0 | 1 | 1 | 1 | 1 | 0 |
| 33 | Serotonin receptor | 5HT R | + | + | + | | + | 1 | 0 | 0 | 0 | 0 | 1 | 1 | 1 | 1 | 0 |
| 34 | Serotonin | 5HT | + | + | + | | + | 0 | 0 | 0 | 0 | 1 | 1 | 0 | 1 | 1 | 0 |
| 35 | Substance P | Substance P | + | + | | | | 0 | 0 | 0 | 0 | 1 | 1 | 0 | 1 | 1 | 0 |
| 36 | Superoxide dismutase Mn | SOD Mn | + | + | + | + | + | 1 | 0 | 0 | 1 | 1 | 1 | 0 | 1 | 1 | 1 |
| 37 | Superoxide dismutase CuZn | SOD Cu/Zn | + | + | + | + | + | 1 | 0 | 0 | 1 | 1 | 1 | 0 | 1 | 1 | 1 |
| 38 | Transforming growth factors beta-1, 2,3 | TGF | + | + | + | | + | 0 | 0 | 0 | 0 | 0 | 1 | 1 | 0 | 1 | 1 |
| 39 | Tumor suppressor p53 | p53 | + | + | + | | | 0 | 0 | 0 | 1 | 0 | 1 | 1 | 0 | 0 | 1 |
| 40 | Vasoactive intestinal peptide | VIP | + | + | | | | 0 | 0 | 0 | 0 | 0 | 1 | 0 | 1 | 1 | 0 |

TABLE 3

SR Biomarkers: Association with SR Pathways

| # | SR Biomarker | Abbreviated Name | 1 | 2 | 3 | 4 | 5 | 6 | 7 | 8 | 9 | 10 |
|---|---|---|---|---|---|---|---|---|---|---|---|---|
| 41 | Heat shock protein 70 | Hsp 70 | | | | + | + | + | + | | + | |
| 42 | Matrix metalloproteinase 9 | MMP | | | | | + | + | | | + | |
| 43 | Aldose reductase | ALR | + | + | + | | | | | | | + |
| 44 | Apoptosis signal-regulating kinase 1 | ASK | | | | | | | + | | | |
| 45 | Aquaporin 5 | AQP | + | + | + | | | | | | | |
| 46 | Betaine GABA transporter 1 | BGT | + | + | + | + | | | | | | + |
| 47 | SAPK | SAPK | | | | | + | + | | | | |
| 48 | Caspase recruitment domain protein 9 | CARD | | | | | | | + | | | |
| 49 | P38 MAPK | p38 | | | | | | + | | + | | |
| 50 | Peripheral benzodiazepine receptor | PBR | | | | | | + | + | + | + | + |
| 51 | Salivary alpha-amylase | SAA | | | | | | | | + | | |
| 52 | GroEL | GroEL | | | | + | | | | | | + |
| 53 | Superoxide dismutase FC | SOD EC | + | | | | + | | | | | + |
| 54 | Cell adhesion molecules | V-CAM, 1-CAM | | | | | + | | | | + | |
| 55 | Monocyte chemotactic protein 1 | MCP | | | | | + | | | | + | |
| 56 | Catalase | Cat | + | | | | | | | | | |
| 57 | Hypoxia induced factor 1 alpha | HIF-1 | + | | | | | | | | | |
| 58 | Glutathione peroxidase | GSHPx | | + | | | | | | | | |
| 59 | Carbonic anhydrase | CAA | + | | | | | | + | | | |
| 60 | Ornithine decarboxylase | ORD | + | | | | | | | | | |
| 61 | Vasoendothelial growth factor | VEGF | + | | | | | + | | | | |
| 62 | Erythropoietin | EPO | + | | | | + | + | | | | |
| 63 | Melatonin | Melatonin | | | | | | + | | + | | |
| 64 | Thyroid-stimulating hormone receptor | TSHR | | | | | | + | | | | |
| 65 | Methenyl-tetrahydro-folate reductase | MTHFR | | | | | | + | | + | | |
| 66 | Oxytocin | Oxytocin | | | | | | | | + | | |
| 67 | Thromboxane synthase 1 | TBXAS1 | | | + | | | + | | + | | |
| 68 | C-reactive protein | CRP | | | | | | | | + | | |
| 69 | TNF-alpha | TNF | | | | | | | | + | | |
| 70 | Apolipoproteins A and B | apo | | | + | | | + | | + | + | |
| 71 | Toll-like receptor | TLR | | | | | | | | + | | + |
| 72 | TspO protein | TspO | | | | | | | | | | + |
| 73 | Bacterial trehalose synthase | Tre-6P | | | | + | | | | | | + |
| 74 | Bacterial Sigma S factor | RpoS | | | | | | | | | | + |
| 75 | Protease DegP | DegP | | | | | | | | | | + |
| 76 | Superoxide dismutase Fe | SOD Fe | + | | | | | | | | + | + |
| 77 | Glutathione reductase A | gorA | | + | | | | | | | | |
| 78 | Ferric uptake regulator | fur | + | | | | | + | | | | |
| 79 | Multidrug efflux pump | aef | | + | | | | | | | | + |
| 80 | Sigma-B factor | Sigma B | | | | | | | | | | + |
| 81 | DNA-binding protein stationary phase | dps | | | | | | | | | | + |
| 82 | DnaJ | DnaJ | | | | + | | | | | | + |
| 83 | GroES | GroES | | | | + | | | | | | + |
| 84 | 8-hydroxy-deoxyguanosine | 8-OH-dG | | | | + | | | | | | |
| 85 | 8-hydroxy-guanine | 8-OH-G | | | | + | | | | | | |
| 86 | DNA damage binding protein-2 | DDB2 | | | | + | | | | | | |
| 87 | Xeroderma pigmentosum (XP) C protein | XPC | | | | + | | | | | | |
| 88 | DNA glycosylase OGG1 | OGG1 | | | | + | | | | | | |
| 89 | pyrimidine-base DNA glycosylases | NEIL | | | | + | | | | | | |
| 90 | uracil DNA glycosylase | UNG | | | | + | | | | | | |
| 91 | thymidine DNA glycosylase | TDG | | | | + | | | | | | |
| 92 | DNA glycosylase | MTH1 | | | | + | | | | | | |
| 93 | Apurinic/Apyrimidinic endonuclease | APE | | | | + | | | | | | |
| 94 | MSH-2 | MSH-2 | | | | + | | | + | + | | |
| 95 | MLH-1 | MLH-1 | | | | + | | | + | + | | |
| 96 | Senescence-associated beta-galactosidase | SA-beta-gal | | | | + | | | + | + | | |
| 97 | P21 | p21 | | | | + | | | + | + | | |

The relationship between each individual stressor and the eleven SR pathways, and thus the SR biomarkers associated therewith, may not always be known, especially since the effects of many stressors on particular SR pathways is not yet well studied. For example, the effects of bird flu virus, engineered nanoparticles, and effects of deep space and deep sea or other extreme environments on each individual SR pathway may not be completely elucidated.

However, most SR biomarkers associated with the 11 SR pathways are useful targets in assays to analyze the effects of both known and unknown stressors, such as environmental stressors and/or diseases-related stressors. Accordingly, SR biomarkers associated with SR pathways are suitable targets for studying the effects of unknown stressors because they provide a response-oriented detection strategy that does not require prior knowledge of the stressor.

SR Biomarkers associated with the SR pathways are also suitable targets in studying the effects of complex stressors, some of which may be known and others of which may be unknown. These complex, or "combined" stressors, are common in real-life scenarios, and may include multiple known and unknown adverse conditions. Global warming, ozone holes, human effects on wildlife, urban pollution, natural and industrial disasters, poverty and war are examples of complex, combined stressors.

2. Dehydration

Dehydration is a water and electrolyte disorder that can severely affect human performance and health[18-21]. Preventable dehydration affects over 90 million people in the US and the costs exceed 10 billion annually for unnecessary hospitalizations and avoidable complications[18-55]. Dehydration includes hypertonic dehydration, isotonic dehydration and hypotonic dehydration. 3% dehydration (i.e., the loss of 3% total body water) is a critical end-point for dehydration diagnostics in field settings because it has measurable negative health consequences but it can be simply treated by oral rehydration[19,21,26,38,56-57]. 3% dehydration can be caused by sweating during strenuous physical work with restricted fluid intake or by extremes of temperature, humidity or altitude[19,21,29-30,58]. This type of dehydration frequently affects soldiers, athletes, construction workers, policemen and firefighters[21,24,26,28,30,44,53,59-63]. Acute dehydration due to gastroenteritis is frequent in children[34,36,39-42,46]. Chronic dehydration associated with oral disease is a common side-effect of cancer therapy or diuretics in diabetic and dialysis patients[31-33,45]. Elderly are at a greater risk for dehydration because the mechanism controlling thirst becomes less sensitive with age, and dehydration occurs more rapidly due to a lower water content in the aging body[25,47,49,51,64]. Many patients in the terminal phase of their illness experience dehydration due to a variety of causes related to their disease or treatment[32-33,48]. Dehydration is a major cause of mental deterioration and death in patients with Alzheimer's disease[35,64]. Life-threatening complications of dehydration include heat stroke, heat illness and hyponatremia due to over-aggressive rehydration[19-21,27-28,30,44,53,61,65]. Dehydration is treated by rehydrating the subject, i.e., by drinking fluids or i.v. saline administration.

Dehydration and hyponatremia are common in patients with cystic fibrosis, kidney, heart and liver disease. Currently used methods for detecting dehydration are based on laboratory analysis of blood, urine, saliva and anthropometric indices such as body mass measurement. The gold standards for dehydration assessment are blood osmolality, body mass loss and TBW measurement using isotope dilution. However, no dehydration test is currently available for wellness and disease management in POC settings and in field conditions. A field-expedient dehydration test is also needed for monitoring the performance and health of military service members during training and deployment. Thus, there is an unmet need for non-invasive, rapid and accurate test for ≥3% dehydration that could be administered frequently to monitor the hydration status of at-risk individuals in field settings[18-19,24,44,59].

The dehydration test provided herein based on salivary SR biomarkers risk is radically different from current dehydration tests because it utilizes a new assay principle based on based on monitoring the physiological status of the patient. Recent studies indicate that the homeostatic processes monitored by SRP are also activated by dehydration. As shown in Table 4, SRP biomarkers are relevant to the sensing of water loss. The assay principle was reduced to practice using an immunoassay of SR biomarkers that monitor the physiological status based on cellular stress responses in saliva. The saliva test is noninvasive, rapid and inexpensive, in contrast, the current dehydration tests monitor physical properties (e.g., osmolality) using blood or urine samples and expensive, time consuming laboratory assays. As described below in the Examples, selected dehydration markers include Acidic Trehalase-like protein 1 (ATM), Osmotic stress protein 94 (OSP94) and Sodium/myo-inositol cotransporter (SMIT).

TABLE 4

SRP Biomarkers and Molecular Sensing of Dehydration

| Cellular and Molecular Effects of Dehydration | Homeostatic Process | SRP |
|---|---|---|
| Efflux of intracellular water | Chaperoning | + |
| Increased intracellular salinity | Redox control | + |
| Cell membrane distortion | Cell adhesion and motility | + |
| Macromolecular crowding and denaturation | Chaperoning | + |
| Increased xenobiotics production | Cellular detoxification | + |
| Oxidative stress | Redox control | + |
| Cell growth arrest | Cell growth | + |
| Pro-apoptotic signaling | Apoptosis | + |
| Hormonal changes | Neuro-endocrine signaling | + |
| Inflammation | Immunity | + |
| Microbial biofilm changes | Microbial activation | + |

3. Occupational Stress

Some occupations involve exposures to complex environmental and psychological stressors, for example astronauts, pilots, divers, soldiers, police and haz-mat personnel. These occupational stressors are typically much more diverse and higher, compared to mainstream professions. Occupational stress can have adverse effects on health and performance and therefore needs to be monitored. Currently, there are no tests for occupational stress.

Occupational stressors can be physical (radiation, health, cold, altitude, gravity, vibrations), chemical (low air oxygen, toxic chemicals, micronutrient deficiency), biological (pathogens, injuries, jet leg, sleep deprivation) or psychological. Often, they involve undefined factors (e.g., outer space radiation, new pathogens).

There are two basic strategies for the detection of occupational stressors. The first one measures levels of potential health threats in the environment (e.g., levels of toxic chemicals). This approach is not suitable for synergistic stressors (e.g., a mixture of individually safe chemicals can be toxic), undefined agents (e.g., new types of pathogens or space radiation) and psychological stressors. The second strategy is based on measuring changes in health status during and after exposures. Currently used health monitors measure vital signs and perform metabolic blood/urine tests. These monitors are not sensitive to many occupational stressors and often they are invasive and not practical (e.g., a nest of wires for vital signs). New health tests under development measure molecular indicators of immunological status (e.g., cytokines and latent viruses in saliva and blood) or assess cognitive performance (e.g., specialized computer games).

The device of the invention offers a better solution for the assessment of complex occupational stressors than any of the current methods. The main advantages of SRP are broad-based sensitivity and new insights into the mechanism of stress. The SRP sensitivity allows an upstream, early detection strategy for a broad spectrum of occupational stressors, in contrast, current methods provide a downstream detection strategy focused on delayed effects. For example, SRP can measure molecular effects directly triggered by a radiation exposure such as increased free radical levels and protein denaturation. These effects precede immunological or cognitive changes by several hours to several days. The insights into the mechanism of occupational stress could be used for the development of countermeasures, 4. Male Fertility Test Current male fertility tests use sperm counts and blood and saliva assays for reproductive hormones. Semen is a complex mucosal fluid with multiple cell types similar to saliva and milk. The device of the invention can be used to measure cellular stress in semen as an indicator of sperm health and a predictor of male fertility.

5. Embryonic Health Test

Current prenatal health tests use amniotic cultures to perform FISH assays genetic abnormalities. SRP-based cellular stress test of the amniotic culture could serve as a new indicator of embryonic health and a predictor of prenatal health.

6. Oral Health Test

Current oral health tests use X rays and dental exams to detect periodontal disease, a serious chronic health problem. New expensive genetics tests are under development. SRP-based cellular stress in saliva could serve as a new indicator of oral health and a predictor of periodontal disease.

7. Saliva as a Diagnostics Sample

Oral diagnostics is a rapidly growing field that provides a convenient alternative to blood sampling for a rapidly expanding list of analytes and diseases, including an early test for a heart attack, it has previously been reported that SRP biomarkers in saliva were sensitive to chronic diseases and post-traumatic psychological stress. Saliva can be sampled simply and noninvasively. A typical saliva sample (10 drops, about 0.3 ml) contains about a half million of epithelial and white blood cells. Salivary cells may play a role in the cellular and molecular mechanism of oral disease transmission. It was also found that salivary cells express SRP biomarkers and that salivary SRP levels are strongly increased by stress.

Saliva diagnostics provides a noninvasive and safe alternative to blood or urine diagnostics[1-3]. The main challenge of using saliva as a diagnostic sample is the inherently low concentration of soluble biomarkers in the cell-free saliva fluid[1-3], which is the currently used method for saliva sampling[1-3]. Whole saliva comprises all normal salivary cells types including epithelial cells, monocytes, B and T lymphocytes and granulocytes, We found that whole saliva contains a large number of cells (about $10^6$/ml) that contain clinically significant biomarkers[4-7]. Therefore, whole saliva samples that contain salivary cells provide a radically improved diagnostic sample for saliva diagnostics compared to samples which do not contain whole saliva cells.

Saliva samples may be collected by the subject or may be collected by a passive method in which a health care worker or person other than the subject collects the sample. For example, unstimulated saliva samples maybe be collected having the subject collect saliva into a sterile container. Alternatively, saliva samples may be collected using a device such as a small oral brush by brushing teeth and gum surfaces on both sides of the mouth for about 20 seconds. To collect a larger volume of saliva, the brushing may be repeated using additional brushes. A comparison of saliva samples collected using self-brushing, and brushing performed by an assistant, showed that both methods yielded the same average sample volume and cellular composition. The passive saliva sampling method (brushing performed by an assistant) enables saliva diagnostics in subjects that cannot actively participate in active saliva sampling such as infants, elderly, unconscious patients or mentally ill patients. Currently, no other passive saliva collection methods were published that enable saliva diagnostics in these subjects.

The device for collecting salivary cells may consist of a disposable brush and a reusable handle. The brush is suitable for oral use. The brush may be used to collect saliva by brushing gums and teeth, and then may be used to process the saliva into smears on slides or lysates.

Methods that collect saliva samples containing salivary cells provide a radical improved diagnostic sample for saliva diagnostics because salivary cells contain clinically significant biomarkers (e.g., proteins and DNA)[4-7]. In contrast, current methods for saliva sampling collect cell-free saliva that has inherently low concentration of soluble biomarkers, which is the main challenge in using saliva as a diagnostic sample[1-3].

In one embodiment of the invention, there are provided reference reagents and materials for saliva diagnostics generated by inducing cellular stress in cultured normal salivary cells by in vitro treatment. Although as described below, the induction of proteomic biomarkers using 5 stressors is exemplified, the treatment principles could easily be adapted to protocols that use different stressors, or other stress markers such as MRNA, DNA, reporters or small molecules associated with the activation of SR pathways (see Table 1). Moreover, the method principles could be also easily adapted for other human cells that have a diagnostic value, white blood cells, and for diagnostic cells from animals, plants and microorganisms. Although the production of cell smears as reference materials is exemplified, the method principles could easily be adapted to the production of other types of reference materials and reagents such as protein lysates, mRNA lysates or cell-free saliva fluid.

Methods that induce cellular stress in cultured normal salivary cells by in vitro treatment provided novel reference reagents materials for saliva diagnostics such as salivary cell smears with normal and increased levels of salivary biomarkers. The in vitro production of reference reagents and materials was rapid, convenient and inexpensive. The new reference materials are radically different from current reference materials produced using cell-free saliva samples[1-3] collected from patients with and without specific medical conditions.

Also provided herein are methods for the development of salivary biomarker assays. In one example, the method uses reference reagents and materials prepared as described in Example 2. Two types of laboratory saliva immunoassays are exemplified, the immunocytochemical (ICC) assay and the ELISA assay. Together, these assays enable the development and validation of saliva biomarker panels because they provide complementary analysis of cell-associated (ICC) and soluble (ELISA) saliva biomarkers as described in Example 5. In addition, laboratory saliva ELISA assays are also useful as reference assays for the development of commercial saliva assays such as the lateral-flow immunoassay (LFIA) test strip. Although as described below, the development of saliva. ICC and ELISA assays exemplified, the principles of the method could easily be adapted to developing other types of immunoassays such as LFIA, and to assays that measure other types of markers such as mRNA, DNA or small molecules. The method for developing new saliva assays using reference reagents and materials produced in vitro was rapid, convenient and inexpensive compared to currently used methods based on clinical saliva samples. Saliva assays produced by the new method use saliva samples that contain salivary cells and therefore the new assays are radically different from current saliva assays based on cell-free saliva samples[1-3].

Also provided are methods for measuring, baseline concentrations of saliva biomarkers using two complementary assays, ICC for cell-associated biomarkers in saliva smears, and ELISA for soluble biomarkers in saliva lysates. In one example, the method uses reference reagents and materials prepared in vitro as described in Example 2. Biomarker baselines in normal saliva provide a useful benchmark the construction of biomarker panels for saliva diagnostics as described. In Example 5. Although as described below, the baseline measurement of a protein biomarker using the ICC and ELISA assays is exemplified, the assay principles could easily be adapted to measure soluble protein markers using other assays such as the lateral-flow immunoassay, and other types of biomarkers such as mRNA, DNA or small molecules.

Also provided are methods for constructing a biomarker panel that is useful for salivary diagnostics of health disorders. Although as described below, panels of proteomic markers are exemplified, the same principle could easily be adapted to measure, for example, mRNA, DNA or small molecules, and to assess the diagnostic value of the saliva biomarker panel using other statistical methods than exemplified here. The new method is rapid, convenient and inexpensive because it uses reference reagents produced in vitro, compared to current methods that use reference reagents based on clinical saliva samples[1-3].

8. LFIA Biosensors

The first FDA-approved commercial oral biosensor broke the ground for a successful commercialization of oral diagnostics. This breakthrough test is ORAQUICK ADVANCE® RAPID HIV-1/2 ANTIBODY TEST produced by OraSure. The test is based on a mature biosensor technology, the lateral-flow immunoassay (LFIA). LFIA is rapidly expanding to provide a wide variety of POC and point-of-need tests for wellness (pregnancy and ovulation tests), public health (HIV and Hepatitis C tests) and forensics (drug and alcohol tests).

Figure 6:
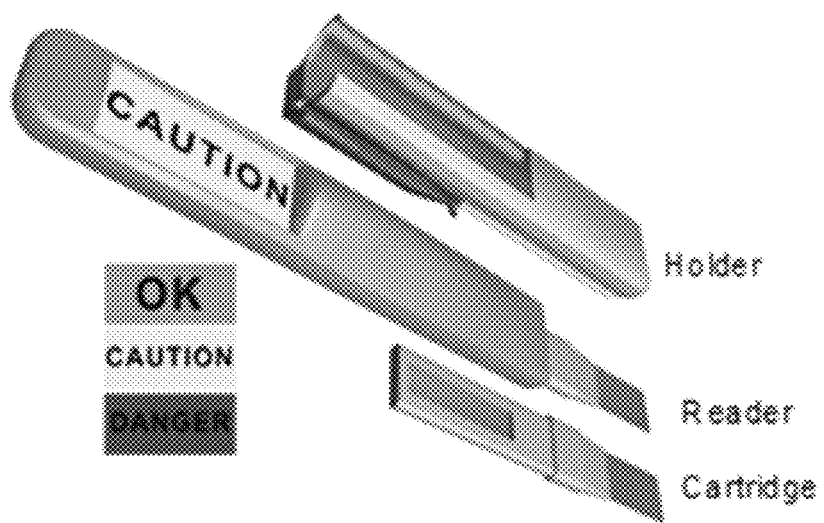
FIG. 6 shows an illustration of a rapid, hand-held test device tier saliva biomarkers. The device consists of a disposable cartridge for uptake of saliva sample and reagent storage, and a reusable reader for signal detection and result display. The result indicates the presence of a saliva biomarker. The digital display window identifies results as normal (display reads "OK"), moderately abnormal (display reads "CAUTION") or highly abnormal (display reads "DANGER").
Figures 7A, 7B:
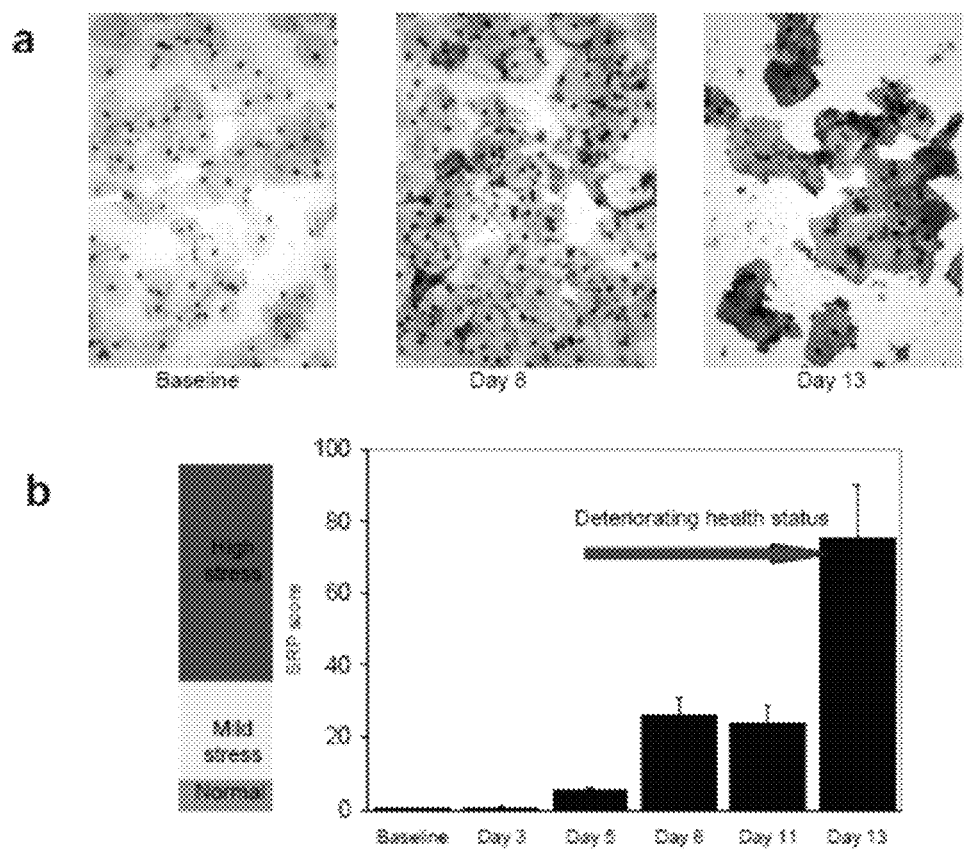
FIGS. 7A-7B.

The present invention provides a simple analyzer that provides a quantitative measurement of physiological stress. Examples of the analyzer is shown in FIGS. 6 and 7A-7B. The analyzer consists of a reusable reader with a digital result display and disposable cartridges (test strips). Alternatively, the whole unit is disposable. The test result is a "stress number," or "SRP score," which is a quantitative indicator of the general stress level. A color-coded results window is used for simplified interpretation of the stress number: e.g., green for normal, yellow for mild/moderate red for high stress levels (similar to a digital thermometer). If the stress number is above the normal range, a digital message prompts the user to obtain advanced analysis of their stress, and to seek medical advice.

In one embodiment of the analyzer device, there is provided a pen-size digital device consisting of a disposable test strip, a reusable electronic reader and a clip-on holster. The user briefly puts the end of the test strip in the mouth to collect saliva and then inserts the test strip into the reader. In less than 3 minutes, the reader shows a digital stress measurement. A color guide shows whether results indicate normal health (green), a mild health problem (yellow) or serious health deterioration (red). Results from multiple tests are stored on board and can be wirelessly communicated to a remote care center. The device operates autonomously using small batteries that last for several weeks.

An advanced analyzer that provides quantitative and qualitative measurements of physiological stress is also provided in the present invention. The analyzer uses a disposable cartridge to perform a highly multiplexed immunoassay (10-40 individual biomarkers). Assay results are measured and processed using an opto-electronic reader, Test results are displayed digitally. The analyzer is equipped for data transfer (USB, Bluetooth) to a web-based service (Stress Net) that supports advanced analysis of test results. The analyzer can be a desktop device or a PDA-class handheld device.

The average SRP score is computed by the device based on measurements of the individual biomarkers and displayed in the results window at the end of the test. The average SRP score will be interpreted as a quantitative indicator of the general stress level, analogous to the "stress number" (combined SR biomarker score), since the average SRP score strongly correlated with combined SR biomarker scores in reference samples. If the general stress level is above the normal range, the user will be prompted to perform advanced analysis of his SRP profile using a web service. The software on the web service interprets the SRP profile and provides user-friendly results in the form of a short message. The message (1) describes the nature of personal stress, e.g., the % risk of specific health problem, (2) shows top three personal stress drivers, (3) recommends wellness products/services that are the best match for the personal stress drivers, and (4) directs the user to additional information, 9. Predictive Medical Diagnostics and Personalized Disease Management Many health problems and diseases do not have a lab test that could provide early warnings before the onset of clinical symptoms. This is particularly true for mental diseases. Often, the earlier a disease is diagnosed, the more likely it is that it can be cured or successfully managed. Managing a disease, especially early in its course, may lower its impact on life or prevent or delay serious complications. Disease management strategy strongly depends on the ability to predict the severity of a disease, for example, differentiating metastatic cancer, Alzheimer's dementia, or kidney failure. Such predictive tests are currently unavailable.

Chronic diseases are associated with early physiological changes that might be detectable using SRP biomarkers in saliva. Early disease tests can be done based on stress-induced changes in microflora and mobile genetic elements (MGE). SRP profiles might reflect the course of a disease. For example, a metastatic cancer might have a different SRP profile than a non-metastatic cancer because metastatic cells produce chemical compounds and biological interactions that are likely to affect stress responses in the normal cells and biofluids analyzed in SRP assays.

Methods: The SRP panel (40 or 41 biomarkers) is analyzed in samples from case/control subjects (cases represent a disease, e.g., breast cancer, BC). If SRP profiles unambiguously discriminate between BC and controls, the panel is minimized toward the smallest panel sufficient for the BC classification. Based on the preliminary data, the minimized panel will consist of 3-6 biomarkers. If SRP profiles from the original. SRP panel do not discriminate BC, new biomarkers are added to the panel until the SRP profile can discriminate BC. The new biomarkers are selected using the SR pathway profile of BC determined by the original SRP panel. For example, if BC-related stress preferentially involves misfolded proteins, oxidative stress and changes in cell cycle and growth, then new biomarkers for these processes will be preferred. When SRP profile can discriminate BC, the biomarker panel will be minimized as described above. The minimized panel is detected using combined SR biomarkers ("multi-SRP assay"), if a combined score is sufficient for BC detection. Alternatively, the biomarkers in the minimized panel are measured individually if a SRP profile is needed for BC detection. A multi-SRP test or an assay for 3-6 individual SRP biomarkers will be implemented using the device of the invention.

10. Human Disease Research

The cellular and molecular mechanism of a disease (i.e., molecular pathogenesis) shows where and how the disease harms the body. Diseases perturb cellular and physiological homeostasis, and the perturbation pattern might be disease-specific and reproducible (i.e., a disease-specific stress signature). Disease countermeasures prevent, reduce or remove the disease-specific stress signature. Disease-specific stress signatures can be analyzed by SRP. This information can be used to guide the development of disease countermeasures: preventive treatments, diagnostics tests and therapeutic interventions. Molecular pathogenesis of most diseases remains elusive including the Spanish flu and AIDS. New molecular and bioinformatics tools are needed, in particular systems biology-based approaches such as SRP measurements using the device of the invention.

11. SRP Tests for Cancer: Oral Tests for Cancer Screening and Lab Tests for Cancer Diagnostics Carcinomas of the skin, breast and prostate are among the most common human malignancies. Current diagnostic methods typically involve a series of tests. For example, a general screening test at POC is ordered by a family doctor during routine health testing (e.g., mammogram for BC). If this test is positive, the patient is referred to a Cancer Center. The Cancer Center surgeon performs a surgical biopsy that is examined by a cancer pathologist using morphological criteria nuclear morphology, mitotic number) and molecular pathology (antibody staining or DNA probing). If the biopsy is considered positive (malignant growth), the patient is referred for additional surgery. The surgical specimen is analyzed by a pathologist to assess the tumor grade based on general grading scales (e.g., Gleason score for PC). New research in personalized medicine aims to delineate the molecular mechanism of individual tumors using gene arrays or antibody staining. Following radio- and chemo-therapy, diagnostic tests based on surgical biopsies and blood assays (not available for most cancers; PSA is used for PC) and are used to identify metastatic cancer. Many cancer survivors suffer chronic pain and mental health problems for which there are no objective tests. A related health problem is care giver stress.

Tests for SRP are applicable across the cancer management continuum—examples are listed below.

(1) Cancer Screening for Noninvasive Early Detection of Cancer.

Rapid oral test for BC and PC: a disposable LFIA. The test is based on a multi-SRP assay optimized for a particular cancer (a yes/no result). Some versions can discriminate metastatic cancer.

Rapid semen test for PC: a disposable LFIA. The test is based on a multi-SRP assay optimized for PC (a yes/no result). Some versions can discriminate metastatic cancer.

Lab test for cervical cancer. The test is based on a multi-SRP staining kit optimized for cervical cancer detection in a standard cervical smear. Some versions can discriminate metastatic cancer. The kit is used to stain a duplicate cervical smear in parallel with the standard PAP test and provide a yes/no result. The SRP test could be used as a decision support for PAP (increased accuracy of cancer prediction) and ultimately replace the PAP test. The accuracy of PAP would be improved in two ways. First, positively staining cells with abnormal morphology (i.e., PAP test reading made easier, faster, more accurate). Second, positively staining pre-cancerous cells with a normal morphology that cannot be detected by PAP. The replacement could happen fast if the SRP test would provide an outstanding benefit over. PAP, e.g., discriminating metastatic cancer.

(2) Cancer Diagnosis for Early Detection of Metastasis.

Lab test for a particular cancer. The test is based on a multi-SRP staining kit optimized for the particular cancer and corresponding tissue type. The kit is used to stain the biopsy tissue and also the surgically removed tissue (tumor and adjacent tissue). The test can discriminate metastatic cancer.

A staining kit for measuring individual SRP biomarkers. Results (SRP profiles) interpreted using the computer software. Results show a match with reference SRP profiles (i.e., discriminate between not cancer, cancer, metastatic cancer). The results indicate the molecular mechanisms of the particular cancer (pathway profile). This information can be useful as a guide for personalized.

(3) Cancer Survivors for improved Quality of Life.

Rapid oral test for cancer-related psycho-biological stress in survivors.

Rapid oral test for cancer care giver stress.

12. Early PTSD Test

A large number of military service members suffer from PTSD and traumatic brain injury (TBI). These diseases are complex psycho-biological disorders that are hard to detect and quantify, particularly in early stages, before they can be assessed using standard psychological neurological tests. These standard tests require highly trained medical personnel, therefore they are not practical for POC or at home monitoring. New tests for PTSD (under commercial development) include assays for saliva cortisol and saliva alpha-amylase (SAA). These analytes are biomarkers for HPA and sympathetic nervous system pathways. SRP covers these pathways and many more pathways that are likely to be activated by psycho-biological stress. Cortisol and SAA are also likely to give false positive signals because they are increased by routine stressors.

13. Early Alzheimer's Test

Alzheimer's disease is the most common cause of dementia. The device of the invention can be used for rapid oral test for early Alzheimer's. The test is based on SRP biomarkers optimized for the disease.

14. Early Autism Test

Autism (ASD) is a rapidly growing health problem for kids in the US. Current goal for autism diagnostics is a test suitable for infant (<3 yrs). Oral SRP test using the device of the invention would be more suitable than tests currently under development.

15. Early Kidney Stones Test

A July 08 report predicted a sharp rise in kidney stones-related health problems in the US due to a higher incidence of dehydration caused by global warming. The device of the invention can be used for a rapid oral test for early detection of kidney stones. The test is based all SRP biomarkers optimized for kidney stones.

16. Early Kidney Disease Test

Chronic kidney diseases (CU)) are on a rise worldwide and early detection is essential for CKD management. The device of the invention can be used for a rapid oral test for early detection of CKD. The test is based on SRP biomarkers optimized for CKD.

17. Animal Wellness and Food Safety

There is a worldwide increase in emerging diseases and environmental stressors related, to factory farming, genetic modifications of crops and life stock, antibiotics overuse, human impact on wildlife and global warming. This increase might be responsible for increased morbidity and mortality of domesticated and wild animals, wild species extinctions, and collapses of the US lobster fishery and the honeybee industry. Early detection of new diseases and environmental stressors is essential for public health, agricultural safety and wildlife protection and management.

Factory farms keep animals in unhealthy conditions. Many animals are diseased and exposed to environmental stressors (crowding, injuries, antibiotics etc.). Organic farms are more likely to have less stressed animals. Besides the ethical objections, products from stressed animals are likely to have a lower nutrient value and might even present a health threat for consumers because stressed animals are likely to be ill and the product might transmit diseases (e.g., mad cow disease), or might contain metabolites that can cause health disorders because they deregulate human cell function. For example, human metabolic disorders triggered by animal hormones or immune disorders triggered by animal stress proteins. Currently, there is no objective test that regulators or consumers can use to assess whether a farm product is from a healthy or from a stressed animal. Such test would help consumers to choose products from minimally stressed animals, and help regulators to search for unhealthy farm conditions.

A related issue is the safety of animal foods (pet food, farm feed). If animal foods contain parts of diseased animals, it might transmit the disease (e.g., BSE) or cause other types of health disorders.

The device of the invention can be used for SRP analysis of animal cells and tissues related to disease, injury, environmental stress, and animal health and product safety, including:

1. Stress Tests for Animals and Animal Products (Milk, Egg).
   The tests use: the device of the invention modified for the use with animal samples.
   Saliva test for companion animals (dog, cat, horse); one smart test device with species-specific cartridges or sample-specific tests.
   Milk test: a health test for dairy animals & milk quality test. Could be made as an attachment for a milking machine or equipment for milk quality test. SRP assay of milk cells and fluids similar to the saliva SRP assay.
   Egg test: a health test for poultry & egg quality test.
   Male fertility test.
   Urine test (a litter test fir cats; farm animals).
   Fish test. Fish biopsy or a surrogate small fish or invertebrate living in the same habitat.
   Shellfish test.
   Beehive wellness test. The honeybee keeping industry has nearly collapsed due to an unknown health threat (environmental factors or disease).

2. Stress Test for Meat.
   Cattle, pork, poultry, fish.

3. Stress Test for Animal Food.
   Multi-SRP test that shows whether pet food and farm feed products contain parts of stressed animals.

4. Stress Test for Sentinel Organisms,
   Multi-SRP test of sentinel animals and wild animals found sick or dead of unknown causes. Increased stress indicates exposure to an emerging/occult disease or environmental stressors. For example, chickens are currently used as sentinels for infectious bird diseases.

18. Agricultural Safety

Plant diseases have increased worldwide possibly due to unsustainable farming practices such as the widespread use of chemical fertilizers, pesticides and genetically modified plants, and global warming. Integrated monitoring of soil/plant/crop health could improve wellness of farm crops, garden plants and house plants, and provide decision support for the protection and management of wild plant ecosystems such as forests and wetlands. Healthy crop plants are likely to produce crops that are more nutritious and case less health problems such as food allergies. Currently, there is no objective test that regulators or consumers can use to assess whether a crop (grains, fruits etc) is from a healthy or from a stressed plant. Such test would help consumers to choose products from minimally stressed plants, and help regulators to search for unhealthy crop conditions.

Soil fertility correlates with the microbial richness of the soil, which is naturally low in some soils (e.g., tropical soil) and becomes depleted by agricultural use. Currently, there is a strong global interest in the restoration of soil fertility due to two factors: a rapidly growing need for increased food production, and soil loss & depletion driven by global warming. However, there is no direct test for monitoring the wellness of soil microflora (the indirect test is the assessment of soil fertility based on crop yield and quality). There are traditional soil probiotics such as compost or charcoal but no new, scientifically-based products that would rationally reduce stress in soil microbial systems.

There is an urgent need for a new technology that could assess and improve soil fertility and crop health. The device of the invention to assess SRP technology meets these specifications.

19. Plant Disease and Food Research

Multi-SRP and SRP assays using the device of the invention can be adapted for soil and plant samples.

20. Stress Tests for Soil, Plants and Crops

Different soil samples can be analyzed using the device of the invention with the SRP biomarker panel optimized for soil microorganisms. Another SRP panel can be optimized for plants, focusing on stress markers for plant organelles (chloroplasts, mitochondria), commensal microorganisms (same as soil) plus stress markers that are in all species (e.g., Hsp60/GroES or SOD). Candidate samples for plants include: roots, leaves, stems, sap. Samples for crops include: grains, fruits.

21. Environmental Safety

Water Safety

Water safety affects public health, aquaculture, agriculture and natural aquatic ecosystems. Standard methods for assessing water safety are based on measuring several chemical and physical parameters (e.g., pH, temperature and turbidity), and levels of specific microbial and chemical contaminants. In England, a traditional method for water safety is still used: the health condition of fish in the water (how many, how fast they swim past the observatory). Frogs are also traditionally used as sentinel organisms tier fresh-water health. Since these methods do not provide early warnings of declining water safety, new methods are currently being developed and tested. Several new methods measure the health condition of native aquatic microorganisms. One method uses an infrared motility monitor. Another one, Aqua Sentinel, developed at the Oak Ridge National Labs, uses a fluorescence reader to measure changes in algal bioluminescence.

The device of the invention can be used to provide SRP-based tests for water safety, and provides several advantages such as: applicability to both fresh water and seawater, broad-based sensitivity to changes in chemical, physical, biological water parameters including parameters that are not measured by current sensors such as new types of air pollutants or agricultural run-off chemicals, early warning of incipient water health deterioration (molecular stress responses precede changes in an algal fluorescent signature or motility), detection of emerging pathogens and bio toxins in aquaculture water that could be directly correlated to fish health, signature can be used to diagnose the nature of the water stress and to recommended countermeasures and used to monitor the effectiveness of countermeasures in restoring water health.

Background—Air Safety

Microbial biosensors for airborne toxins have been introduced recently. Typically, these are genetically engineered bacteria or recombinant flies with a read-out gene (e.g., lux) linked to one of several particular toxin-sensitive genes (hsp70, DNA J). The disadvantage is that recombinant organisms have to be manufactured for the biosensor operation, and the small set of recombinant sensor genes in the biosensor might not be sensitive to the large and diverse spectrum of environmental stressors that affect people. The device of the invention can be used to provide SRP-based tests for air safety, 22. Space Technology Key areas in space biology research that are useful with the device of the invention include: diagnostic and therapeutic technologies for astronaut health. The goal is to identify health risks of space flight and develop countermeasures to reduce those risks. The device of the invention can also be used for fundamental space biology investigations in microbial, plant and cell biology and animal physiology, i.e., how life responds to gravity and space environments. Additionally, the device of the invention can be used to detecting life's signatures for future planetary missions to Mars, Europa and Titan.

23. Detection of Life's Signatures

Stress responses (SR) are universally present in all organisms on Earth. Responses to universal stressors are essential for life in general and could be used in the search for life. The universal stressors are physical-chemical gradients or agents commonly present in planetary geological environments (e.g., electromagnetic radiation, radioactivity, temperature, gravity, heavy metals, water, $CO_2$). Universal stressors are also generated by general biological processes such as self-organization, electron transfer and metabolism (e.g., heat, entropy and free radicals). Different biological systems might use very different biochemical structures for SR but the different biochemical structures are likely to have the same or similar physical-chemical functions. These general functions can be deduced through comparative study of biochemical structures that are commonly used for SR by terrestrial organisms. Components of the general physical-chemical SR functions are used as biomarkers for life.

For example, free oxygen and nitrogen radicals (RONS) are universal stressors produced by solar radiation as well as a by-product of electron transfer and metabolic reactions. RONS cause harm to all living systems through damage to macromolecular structures and Shills in redox balance. All terrestrial organisms have SR against RONS. Most prokaryotes and eukaryotes use control RONS using superoxide dismutases (SOD). The physical-chemical function of SOD is carried out by the metal moiety of SOD, which contains an antioxidant heavy metal (Fe, Mn, Cu, Zn). These and similar (Ni, Co) metals are candidate biomarkers for biological anti-RONS responses.

Another universal stressor is water loss (desiccation). Most prokaryotes and eukaryotes have a SR for adapting to life without water (Anhydrobiosis). If there was or is life on Mars, it had to deal with periodical desiccation as well. The physical-chemical functions underlying the anhydrobiosis SR are candidate markers tier life detection.

Bacterial and eukaryotic, cells use organic osmolytes to cope with anhydrobiosis (glutamate, proline, glycerol, sucrose, trehalose, sorbitol, myo-inositol and glycine betaine). The physical-chemical principle of the osmolytic compounds is structure-making (cosmotropic) function: they organize the water structure (hydrogen bonding) which is essential for structural integrity of biological membranes and biopolymers proteins). The known organic osmolytes listed above, and other cosmotropic compounds, are candidate biomarkers for biological response to osmotic stress and for anhydrobiosis.

24. Monitoring HIV/AIDS Risk and Treatment Outcome

HIV/AIDS is a priority public health condition[67]. There are about 1.1 million HIV infected people the U.S. and 56,300 new HIV infections annually[67]. Currently, two lab tests (CD4 count and viral load) are the gold standards for assessing AIDS risk and guiding cART[68-69]. CD4 counts 350 (recently increased to 500) and 200 cells/mm$^3$ are standard actionable thresholds for guiding cART[68]. The CD4 test is expensive, invasive, time consuming, requires specialized equipment, highly trained personnel and has to be repeated every 3-4 months. Thus, there is an unmet need for an affordable POC test for AIDS risk and guiding cART[69]. HIV/AIDS is typically treated with non-nucleosidase reverse transcriptase inhibitors, nucleosidase reverse transcriptase inhibitors, protease inhibitors, fusion inhibitors, CCR5 antagonists, integrase strand transfer inhibitors or a combination thereof.

In one embodiment of the invention there is provided a rapid saliva test for HIV progression (unsuppressed HIV) and acute HIV that has been developed using following steps: (1) A candidate panel of 52 SR markers (see Tables 2 and 3) was constructed using methods from Example 5. (2) The initial clinical validation of the panel used methods from Example 5 and saliva samples from HIV/AIDS patients (n=100) with CD4 counts >500, 200-500 and <200 cells/mm$^3$. The AIDS risk test based on salivary SR biomarkers is radically different from current tests for the condition because it utilizes a new assay principle based on monitoring the physiological status of the patient. The assay principle was reduced to practice using an immunoassay of SR biomarkers that monitor the physiological status based on cellular stress responses in saliva. The saliva test is noninvasive, rapid and inexpensive. In contrast, current tests for AIDS prognostication monitor the immunologic, virological or genetic status of the patient using blood samples and expensive laboratory assays[68-69,72]. The saliva test for AIDS prognostication has potential to provide significant benefits for public health and substantial healthcare savings in several ways: (1) Accelerating HIV/AIDS care and slowing the spread of HIV: Two rapid oral tests could be administered during routine healthcare screening, an HIV diagnostics test followed by the saliva test in order to inform patients about their HIV status and AIDS risk in a single office visit so that they could receive care immediately. Pain-free, affordable oral testing is likely to increase the number of HIV/AIDS patients connected to care and fewer people be exposed to HIV: 54-70% of new HIV infections in USA are caused by people who are not treated and engage in risky behaviors because they do not know that they are HIV infected[67]. (2) Moving AIDS monitoring from lab to point-of-care will greatly improve the delivery of clinical care and medications in resource-limited settings where the standard tests for AIDS risk are not affordable and costly cART drugs are delivered inefficiently, without lab tests[69,74]. (3) Enabling personalized HIV medicine: frequent affordable testing of cART efficacy will facilitate designing and modifying cART for individual patients, which has potential to improve treatment outcomes and decrease clinical costs[72]. Current treatment for HIV/AIDS include Non-nucleoside reverse transcriptase inhibitors (NNRTIs); Nucleoside reverse transcriptase inhibitors (NRTIS); Protease inhibitors (PIs); Fusion inhibitors; CCR5 antagonists (CCR5s); Integrase strand transfer inhibitors (INSTIs) and combinations thereof. As described in the Examples below, biomarkers for HIV progression (unsuppressed HIV) and Acute HIV include Bone Marrow Stromal Cell Antigen 2 (BST2), Salivary Agglutinin gp340 (SAG) and Vascular endothelial growth factor C (VEGF-C).

25. Traumatic Brain Injury

Traumatic brain injury (TBI), also known as intracranial injury, occurs when an external force traumatically injures the brain. TBI can be classified based on severity, mechanism (closed or penetrating head injury), or other features (e.g., occurring in a specific location or over a widespread area). Traumatic brain injury (TBI) includes mild TBI (mTBI, concussion), severe TBI (sTBI) and neurocognitive disorder (NCI)) due to TBI (NCDT). Brain trauma can occur as a consequence of a focal impact upon the head, by a sudden acceleration/deceleration within the cranium or by a complex combination of both movement and sudden impact. In addition to the damage caused at the moment of injury, brain trauma causes secondary injury, a variety of events that take place in the minutes and days following the injury. These processes, which include alterations in cerebral blood flow and the pressure within the skull, contribute substantially to the damage from the initial injury. TBI can cause a host of physical, cognitive, social, emotional, and behavioral effects, and outcome can range from complete recovery to permanent disability or death. Some of the current imaging techniques used for diagnosis and treatment include computed tomography and MRIs. Depending on the injury, treatment required may be minimal or may include interventions such as medications, emergency surgery or surgery years later. Physical therapy, speech therapy, recreation therapy, occupational therapy and vision therapy may be employed for rehabilitation. Mild traumatic brain injuries usually require no treatment other than rest and over-the-counter pain relievers to treat a headache. Moderate to severe traumatic brain injuries focuses on making sure the person has an adequate oxygen and blood supply, maintaining blood pressure, and preventing any further injury to the head or neck. Medications to limit secondary damage to the brain immediately after an injury may include: Diuretics; Anti-seizure drugs; and Coma-inducing drugs. As described in the Examples below, biomarkers for NCDT include Cytochrome P450 Reductase (CYPOR), Natriuretic peptide receptor A (NPR) and Oxytocin receptor (OTR).

26. Post-Traumatic Stress Disorder

Posttraumatic stress disorder (PTSD) is a mental disorder that can develop after a person is exposed to a traumatic event, such as sexual assault, warfare, traffic collisions, or other threats on a person's life (en.wikipedia.org/wiki/Post-traumatic_stress_disorder-cite_note-DSM5-2). Symptoms may include disturbing thoughts, feelings, or dreams related to the events, mental or physical distress to trauma-related cues, attempts to avoid trauma-related cues, alterations in how a person thinks and feels, and increased arousal. These symptoms last for more than a month after the event. Those with PTSD are at a higher risk of suicide. Diagnosis is based on the presence of specific symptoms following a traumatic event. The Main treatments for people with PTSD are counselling and medication. Antidepressants of the selective serotonin reuptake inhibitor type are the first-line medications for PTSD and result in benefit in about half of people. Other treatments for PTSD include tricyclic antidepressants, atypical antidepressants and mood stabilizers.

27. Heart Disease

Heart disease includes acute heart failure (AHF) with preserved ejection fraction (HF-pEF), AHF with restricted election fraction (HF-rEF) and atrial fibrillation. Heart failure (HF), often referred to as congestive heart failure (CHF), occurs when the heart is unable to pump sufficiently to maintain blood flow to meet the body's needs. Signs and symptoms commonly include shortness of breath, excessive tiredness, and leg swelling. The shortness of breath is usually worse with exercise, while lying down, and may wake the person at flight. Common causes of heart failure include coronary artery disease including a previous myocardial infarction (heart attack), high blood pressure, atrial fibrillation, valvular heart disease, excess alcohol use, infection, and cardiomyopathy of an unknown cause. There are two main types of heart failure: heart failure due to left ventricular dysfunction and heart failure with normal ejection fraction depending on whether the ability of the left ventricle to contract is affected, or the hearts ability to relax. The severity of disease is usually graded by the degree of problems with exercise. Heart disease is treated with Angiotensin-converting enzyme (ACE) inhibitors (examples include enalapril (Vasotec), lisinopril (Zestril) and captopril (Capoten)); Angiotensin II receptor blockers (examples include Cozar); Beta blockers (examples include carvedilol (Coreg), metoprolol (Lopressor) and bisoprolol (Zebeta)); Diuretics furosemide (examples include Lasix); Aldosterone antagonists (examples include spironolactone Aldactone) and eplerenone (Inspra)); inotropes and Digoxin (Lanoxin). As shown in the Examples below, biomarkers for heart disease include Cyclooxygenase-2, Epidermal growth factor receptor, Leptin and MAP kinase Mek-1.

28. Kidney Disease

Kidney disease, also known as nephropathy or renal disease, is damage to or disease of a kidney. Nephritis is inflammatory kidney disease. Nephrosis is noninflammatory nephropathy. Kidney disease usually causes kidney failure to more or less degree, with the amount depending on the type of disease. Acute kidney injury has often been called acute renal failure, although nephrologists now often tend to call it acute kidney injury. As used herein the term kidney disease includes chronic kidney disease (CKD) and acute kidney injury (AKI). Kidney disease may be treated by various methods including angiotensin-converting enzyme (ACE) inhibitors, such as captopril (Capoten), enalapril (Vasotec), fosinopril (Monopril), lisinopril (Prinivil, Zestril), or ramipril (Altace); angiotensin receptor blockers (ARB), such as azilsartan (Edarbi), eprosartan (Teveten), irbesartan (Avapro), losartan (Cozaar), olmesartan (Benicar), and valsartan (Diovan); darbepoetin alfa (Aranesp) or erythropoietin (Procrit, Epogen). As shown in the Examples below, kidney disease biomarkers include Annexin 5, Nuclear actor of activated cells5 and Osmotic stress protein 94.

The following examples are intended to illustrate but not limit the invention.

Example 1

Collection and Processing of Improved Saliva Samples for Saliva Diagnostics

This experiment provides an exemplary method for collecting and processing saliva samples that contain salivary cells. Although as described below, assays based on the collection of human unstimulated saliva by spitting or brushing are exemplified, the assay principles could easily be adapted to protocols that collect and process stimulated saliva samples, or use other devices and methods, or collect animal saliva.

Sample Collection. Unstimulated saliva samples were collected from healthy volunteers (5 women, 5 men, 8-53 yrs old). The subjects were asked to brush teeth and have no food or beverage except water for 30 minutes (min) before the collection. Two collection methods were used: (1) Spit was collected into a sterile container such as the 50 ml Falcon tube. Subjects spit into the tube several times during about 1.5 minutes (min) until 3 to 6 ml of saliva was collected. During the collection, the tube was kept on ice. (2) A small oral brush described in FIG. 1 was used to collect saliva by brushing teeth and gum surfaces on both sides of the mouth for about 20 seconds. When a commercial oral brush (the PROXABRUSH Traveler, Sunstar Americas, Chicago, IL) was used for this collection method, the average collected saliva volume was 0.16±0.02 ml. To collect a larger volume of saliva, the brushing was repeated using additional brushes. A comparison of saliva samples collected using self-brushing and brushing performed by an assistant, showed that both methods yielded the same average sample volume and cellular composition.

Sample Quality Tests: (1) Adequate pH (6-8) was assessed by spotting 5 microliters of the whole saliva on a pH test strip, or by pressing the tip of the gum brush on a pH strip. Samples tested so far (n>100) had pH=7.2±0.6. (2) The adequate cell count (epithelial cells and leukocytes) was assessed using one of the following methods. 1. Viable cell count. Saliva sample collected by spitting was mixed thoroughly using a sterile 1 ml pipette. Using a sterile pipette tip, 10 microliters from the middle of the tube was transferred into a tube with 10 microliters of 0.4% trypan blue in the phosphate saline buffer pH 7.60 (PBS), mixed using the pipette tip, stained for 10 minutes (min). 10 microliters of the mixture was transferred into both chambers of a standard hemocytometer and viable cells (nucleated cells unstained by trypan) were counted using ×100 magnification. Adequate viable cell count was at least $0.2 \times 10^6$ cells/ml. 2. Total cell count. Saliva sample collected by spitting was mixed thoroughly using a sterile 1 pipette. Using a sterile pipette tip, 5 microliters from the middle of the tube was smeared across a small square (about 1 cm²) on a coated microscopy slide (a Silane Prep slide from Sigma, St. Louis, MO). Alternatively, saliva collected by the brush was smeared across about 1 cm length of the slide. Air dried saliva smears were fixed. (1 dip in 2% formaline-1% acetic acid 80% ethanol followed by 10 dips in water) and stained using hematoxylin and eosin (H&E stain, Sigma): 10 dips in hematoxylin followed by 10 min in water, 10 dips in 80% ethanol, 10 dip in eosin, 10 dips in 95% ethanol, air dry, 2 dips in xylene, coverslip. Cells stained with H&E were counted at ×100 magnification. The adequate cell count was at least 2,500 cells per smear (>$5 \times 10^5$ cells/ml). Normal saliva smears typically contained nucleated epithelial cells and leukocytes as well as about 10% of epithelial cells without nuclei. (3) The adequate cellular composition of the sample was determined based on microscopic inspection of the H&E saliva smear. A typical saliva sample collected by spitting had about 60% epithelial cells and 40% leukocytes (monocytes, lymphocytes and granulocytes). Brush-collected samples typically had about 50% epithelial cells and 50% leukocytes. In addition, all normal saliva samples also contained variable amounts of resident bacterial and fungal cells (about $10^5$-$10^7$ microbial cells/ml). The salivary microbial cells were associated with the mammalian cells, or formed microbial clumps or were dispersed as single cells.

Salivary Cell Smears on Microscopy Slides ("Smears"). Smears are useful for salivary diagnostics in multiple ways. They enable H&E analysis and the quantitative measurements of cell-associated molecular biomarkers (proteins, peptides, mRNA, DNA, small molecules such as eicosanoids, or reporters) in salivary epithelial cells, leukocytes and microbial cells. Proteomic markers and small molecules can be measured using the immunocytochemical staining ("the ICC assay") or by other assays such as reporter assays or in situ nucleic acid hybridization. Smears were prepared using following methods. 1. Saliva collected by spitting. The sample was thoroughly mixed in a tube using a 1 ml sterile pipette. Using a sterile pipette tip, 40 microliter from the middle of the tube was transferred on a coated slide and the spot was immediately spread across the Whole slide using the tip. The tip was tilted at a sharp angle to facilitate the spreading. In some experiments, smaller volumes of saliva were spread in separate areas of the slide to compare different saliva samples on the same slide (e.g., four smears, 10 microliter each). 2. Samples collected using oral brush. Immediately after removing from the mouth, the brush was smeared across the length of a coated slide. The same brush was used to prepare additional slides (typically, 4 slides per brush). Additional brushes were used to collect more saliva and prepare a full set of slides for biomarker analysis (e.g., 25 slides were prepared using 7 brushes). Smears prepared sing the spit or brush methods were air dried at room temperature (RT) for at least 30 min, fixed in 10% normal buffered formalin for 10 min, followed by 3×5 min rinses PBS, 5 min in water and 5 min each in 80%, 95% and absolute ethanol. Dry fixed slides were stored in a standard histology slide box at RT. The fixed slides were stable for over 3 years based on the ICC assay using control antibodies.

Salivary ICC Assay. The main advantages of ICC are sensitivity (specific staining of single cells corresponding to 0.1-1 pg/ml antigen concentration) and specificity (each marker stains specific cell type and has a characteristic cellular localization). To demonstrate compatibility with ICC, representative saliva smears were stained with control antibodies. Positive control antibodies were specific for antigens consistently expressed by salivary epithelial cells or leukocytes. As positive controls, EMA (a membrane antigen on about 30% salivary epithelial cells; mouse IgG2a, 0.2 microgram/ml, Biogenex, San Ramon, CA) and CD68 (a cytoplasmic antigen in salivary monocytes, B cells and neutrophils, mouse IgG1, 0.5 microgram/ml, Dako, Carpenteria, CA) were used. Negative control antibodies were mouse monoclonal antibodies (Mab) and rabbit polyclonal antibodies (Pab) specific for irrelevant antigens that are not present in salivary cells. Negative controls matched the concentration, species and type of positive control antibodies and anti-biomarker antibodies. As negative controls, a mouse IgG1 Mab (anti-digoxigenin, 0.5 microgram/ml, Santa Cruz Biotechnology, SCBT, Santa Cruz, CA) and a rabbit Pub (anti-Drosophila armadillo, 0.2 microgram/ml, SCBT) was used. A new protocol was developed to enable ICC assay of saliva smears. Before staining, dry slides were scored with a diamond pen to outline sections for the application of different antibodies (typically 4 control antibodies were applied to one slide; in antibody titration experiments, 8 antibodies were applied to one slide). Assay steps: (1) Based on extensive testing, it was determined that commonly used antigen unmasking methods that use heat treatment (citrate or glycin buffers, 95-100° C. for 10-20 min) were not suitable for saliva smears because >80% cells fell off slides during the heat treatment. Therefore, a new method was developed for antigen unmasking in saliva smears: slides were placed in 20 mM citrate, 0.1 mM EDTA buffer (pH 3.0) at 37° C. for 60 min, followed by 5 min rinses in water and PBS pH 7.60. (2) Slides were blocked using PBS with 7% normal goat serum for 30 min. (3) Based on extensive testing (64 rabbit and goat Pabs, 25 mouse and rat Mabs, Mabs), we determined that (i) Mabs (whole culture supernatants, ascites or purified immunoglobulins) and immunoaffinity-purified Pabs were suitable for salivary immunoassays whereas (ii) Pabs in the form of the whole serum (nonimmune serum or antiserum) or the immunoglobulin fraction of a whole serum, were unsuitable for salivary immunoassays because they contained antibodies that strongly stained 10-30% salivary microbial cells even when highly diluted. (<10:1000). The anti-microbial affinity of whole serum has never been reported previously, probably because typical samples for immunoassays are sterile tissue culture cells, blood cells and fixed tissues that were stripped of resident microbes. Based on the results, only Mabs or affinity-purified Pabs were used for all saliva immunoassays (ICC or other assay formats). (3) Optimal concentrations of primary antibodies (the EMA, CD68, digoxigenin, mouse antibodies) were diluted in PBS, pH 7.60 with 1% bovine serum albumin (BSA) and applied to individual sections on blocked slides after draining off the blocking solution and dividing the cell smear into fields by wiping between the outlined sections using a sharply folded paper tissue. The total antibody volume was 0.3 ml per slide. Afterwards, slides were placed in a humidified chamber at 4° C. for 16-20 hrs. (4) After 3×5 min rinse with PBS, a secondary antibody was applied for 90 minutes at RT (a biotinylated goat antibody against mouse and rabbit IgG, Biogenex, 1:20 in PBS-BSA), followed by 3×5 min rinse with PBS, enzymatic conjugate for 30 min at RT (a streptavidine-alkaline phosphatase conjugate, Biogenex, 1:20 in PBS-BSA), 3×5 min rinse with TBS (50 mM Tris, 150 mM NaCl, pH 7.60), chromogen (Fuchsin, Dako), 5 ruin water rinse, hematoxylin stain for 1 min, 15 min water rinse and two 5 min rinses with 95% ethanol. Air dried slides were rinsed in xylene and cover-slipped before a microscopic examination at ×100 magnification. (5) The staining intensity was quantified using computerized image analysis. 3 representative images were captured in each stained section and areas with at least 100 epithelial cells leukocytes were outlined in each image. The mean optical density (MOD) in the outlined area, and the percent of the stained area (PA), were determined by, applying a color file to the image. The same color file was applied to all images to ensure consistent MOD and PA measurements. The staining intensity (SI) was calculated as SI=MOD×PA. The mean SI was calculated for 3 images per stain. To determine the reproducibility of the assays, the mean SI was measured in 12 duplicate stains produced in the same and consecutive assay runs. The measurements were compared using linear regression analysis to calculate 95% confidence interval for the mean of differences. The coefficient of variation (CV) was 9.8%, demonstrating that the measurement was reproducible. Results of the control staining showed critical parameters for the ICC assay: sensitivity 0.1-1 pg/ml (based on the EMA antigen concentration), specificity (no staining with negative control antibodies), intra- and inter-assay reproducibility (<10% CV for the mean SI measurements).

Saliva Protein Lysates. The lysates enable detecting protein, peptide and small molecule biomarkers present is cell-free saliva and released from solubilized salivary cells. Lysates can be analyzed using ELISA, protein blots, mass spectrophotometry, chromatography or other types of assays. As explained, in the ICC assay protocol above, antibodies suitable for saliva immunoassays are Mabs or immunoaffinity-purified Pabs, Lysates were prepared using two methods. (1) Spit-based samples: 1 ml of a 2× concentrated lysis buffer (LB) was added per 1 ml saliva; the sample was thoroughly mixed using a sterile 1 ml pipette and kept on ice far 30 min. The final concentrations in the lysate were 1 mM EDTA, 1 mM PMSF, 1 mg/ml N-ethylmaleimide, 0.02 mg/ml ovatrypsin inhibitor, 0.1 mg/ml aprotinin, 6 mg/ml 4-aminobenzamidine dichloride and a cocktail of mammalian phosphatase inhibitors from Sigma diluted in PBS. (2) Saliva was collected using the oral brush (FIG. 1) as described above. Immediately after the collection, the brush was removed from the handle and suspended in 2× LB. Four brushes (the PROXABRUSH Traveler, Sunstar Americas) were mixed with 0.3 ml of the LB in one microcentrifuge tube by swirling the brushes in the buffer for 30 seconds. The brush was kept in the buffer on ice for 30 min, and then removed. After lysis, insoluble material was removed by centrifugation at 12,000 rpm and the supernatant was transferred to a new tube and immediately frozen at −80° C.

Saliva ELISA. The ELISA assay complements the ICC assay of biomarkers in salivary cells by measuring soluble biomarkers. The main benefits of ELISA are sensitivity to 1 pg/ml biomarker concentrations, consistent high throughput and reliable metrics (pg/ml concentration) that clearly show the success of clinical diagnostic studies. To demonstrate compatibility with ELISA, we used a multiplexed Multi-Bead ELISA (Inflammatory Panel, Assay Designs, Ann Arbor, MI) to measure 8 control proteins (IL-1beta, IL-6, IL-8, IFN-gamma, TNF-alpha) and small molecules (eicosanoids PGE2 and TXB2) with known concentrations in normal saliva[8-10]. Calibration curves for the analytes were constructed using serial dilutions of purified standards first in buffer (PBS-BSA) and then saliva matrix (the saliva protein lysate described above, a pool from several subjects). The assay was optimized to reach benchmark values of critical assay parameters: limit of detection at 1-10 pg/ml, linear range 10 pg-10 ng/ml, recovery (assay interferents), specificity (no signal with irrelevant purified antigens), intra- and inter-assay reproducibility (<10% CV for the mean measurements of duplicate samples in the same and in consecutive assay runs). The optimized assay was used to measure the 8 control analytes in normal saliva lysates from individual subjects.

Saliva DNA Lysates. These lysates enable measuring DNA released from solubilized salivary cells. DNA prepared from the lysates can be analyzed using PCR, DNA blots or other types of DNA assays. Assays of saliva DNA have potentially wide applications in human and animal diagnostics including pharmacogenomics (individualized testing of drug safety and efficacy), testing for genetic disorders (disease prognostics), paternity and forensics. Although as described below, a protocol for DNA preparation is exemplified, the protocol principles could easily be adapted to protocols that prepare RNA, Saliva DNA lysates were prepared from saliva collected by spitting in a tube or by oral brushing as described above. The objective was to develop a simple method that could be used in field conditions using reagents and lysates that are stable at RT, and can be later processed in a laboratory to prepare DNA suitable for PCR amplification. Six such methods were developed: (1) 0.1 ml of a 5× concentrated lysis buffer (LB) was added to 0.5 ml spit in a sterile tube, the sample was thoroughly mixed using a sterile 1 ml pipette or vigorous shaking, Final concentrations in the lysate were 10 mM Tris-HCl, 10 mM EDTA, 0.1% sodium dodecyl sulphate (SDS). Fresh concentrated Proteinase K (PK, Qiagen, Valencia, CA) was added to 10 microgram/ml final concentration. The lysate was incubated at 50° C. for 1 hr, boiled for 3 min, 25 microliter of 5M NaCl was added to 0.2 M final concentration, the sample was mixed with 1 ml absolute ethanol, incubated at RT for 20 min, centrifuged at 14,000 rpm for 10 min, the pellet was rinsed with 70% ethanol, air dried and dissolved in 50 microliter of 10 mM Tris-1 mM EDTA buffer pH 7.60 (TE). (2) Same as Method 1 but the LB contained diluted PK and was stored at RT for 2 days before use, (3) Same as Methods 1 or 2 but after boiling, 50 microliter of 5 M iced potassium acetate (pH 4.8) was added, the sample was mixed thoroughly, iced for 30 min, centrifuged at 14,000 rpm for 15 min, the supernatant was transferred to a new tube, mixed with 1 ml of absolute ethanol, incubated at RT for 20 min, centrifuged at 14,000 rpm for 10 min, the pellet was rinsed with 70% ethanol, air dried and dissolved in 50 microliter of TE. (4) Same as Methods 1-3 but the lysate was incubated at RT for 18 hrs instead of at 50° C. for 1 hr. (5) 0.5 ml of spit was mixed thoroughly with 0.1 ml of a concentrated lysis buffer by vortexing or vigorous shaking. Final concentrations in the lysate were: 50 mM NaOH, 10 mM EDTA and 0.025% SDS, and the pH was about 12. The lysate was stored at RT for 8 days without additional mixing. On day 9, the lysate was boiled for 10 min, iced to RT, neutralized to pH 7.8 by adding 5 microliter of 2M Tris-HCl pH 7.0 and 25 microliter of 1M HCl. The neutralized lysate contained 50 mM NaCl. Insoluble material was pelleted by centrifugation at 14,000 rpm for 5 min, the supernatant was transferred to a new tube, 15 microliter of 5 M NaCl was added to final concentration of 0.2 M, the lysate was mixed with 1 ml of absolute ethanol, incubated at RT for 20 min, centrifuged at 14,000 rpm for 10 min, the pellet was rinsed with 70% ethanol, air dried and dissolved in 50 microliter of TE. (6) Same as Methods 1-5 but saliva was collected using an oral brush (FIG. 1) as described above. Immediately after the collection, the brush was removed from the handle and suspended in LB. Four brushes (PROXABRUSH Traveler, Sunstar Americas) were mixed with 0.1 ml of 5× LB in one microcentrifuge tube by vortexing or by 10× swirling the brushes in the buffer. To estimate the DNA concentration and the molecular weight (MW), 5 microliter each of a DNA standard (HyperLadder I, Bioline, Taunton, MA) and the saliva DNA were analyzed using a standards 0.7% agarose TBE gel with 0.5 microgram/ml ethidium bromide. The average yield per 1 ml saliva was: 3±1 microgram of high MW DNA (>20 kbp) for Methods using PK (1-4) and 1.5±0.5 microgram of mediate-low MW DNA (1-20 kbp) for Methods using NaOH (5). To show compatibility with PCR, a 500 by fragment of the human IFN-beta gene was amplified in the different saliva DNA preparations using following primers: 5' ATG ACC AAC AAG TGT CTC CTC CAA A (SEQ ID NO. 1) and 5' GTT TCG GAG GTA ACC TGT AAG TCT G (SEQ ID NO. 2), and standard hot-start reaction conditions using 1.5 mM $MgCl_2$, 40 Cycles: 94° C. (45 sec); 60° C. (60 sec); 72° C. (60 sec), then final extension at 72° C. (10 min), The PCR product and a DNA standard were visualized using a standard 2% agarose gel stained with ethidium bromide.

Salivary Cells. Live, fixed or permeabilized salivary cells are useful for salivary diagnostics by enabling the detection of molecular biomarkers using flow cytometry (FCM) or immunofluorescence assays. As explained in the ICC assay protocol above, antibodies suitable for saliva immunoassays are Mabs or immunoaffinity-purified fabs. Salivary cells were prepared using the following procedure: Spit was diluted 1:1 with a staining buffer (SB: phosphate buffered saline, pH 7.6, 2% BSA, 0.1% azide) and centrifuged at 300 g for 5 min. Brush-collected salivary cells were released into SB (10-30 brushes submerged in 1 ml SB, 5 min on ice on a rocker), and centrifuged as above. The cell pellet was suspended in a minimal volume of SB (e.g., 0.1 ml), 5 microliter were removed to perform a cell count, and to determine >90% cell viability using trypan blue exclusion as described above. The average yield was about $6 \times^5$ mammalian cells/ml spit and about 3×10 4 cells/brush. To demonstrate compatibility with FCM analysis, duplicate samples of salivary cells were stained with control antibodies using a standard protocol for staining of live cells: The cell suspension was diluted to get a final cell concentration of about $10^6$ incubated with anti-Fc receptor antibody (CD32, SCBT, 1 mg/ml, 10 min), divided into staining samples in microcentrifuge tubes (at least $1 \times 10^5$ cells/sample), centrifuged at 300 g for 5 min at 4° C., resuspended in 0.1 ml with a FITC-labeled primary antibody diluted in SB (1:5 diluted CD68-FITC and normal mouse $IgG_1$-FITC, SCBT), mixed and incubated on ice in dark for 30 min, rinsed 3× with SB and transferred into a Falcon 2052 tube with 0.4 ml SB before FACS analysis.

Example 2

Production of Reference Reagents and Materials for Salivary Diagnostics

This experiment provides an exemplary method for the production of novel reference reagents and materials tier saliva diagnostics by inducing cellular stress in cultured normal salivary cells by in vitro treatment.

Preparation of Stressed Salivary Cells. Saliva samples (6 ml) were simultaneously collected from 3 healthy volunteers (1 man and 2 women, 19-52 years old) using the spit method from Example 1, The acceptability of the samples was immediately evaluated using a pH test and H&E stain as described in Example 1. The samples were combined into a "Normal (N) pool". A portion the N pool was processed into smears and or lysates using protocols from Example 1 (e.g., 3 ml was processed into 75 smears). The remaining N pool (15 ml) was divided into 5 cultures: (3 ml saliva, ~$1 \times 10^6$ viable cells/culture), culture). The cultures were maintained in sterile Petri dishes (polystyrene, 60 mm×15 mm, Sigma) in a standard cell culture incubator at 37° C. for 18 his without adding culture medium. The cultures contained Whole saliva with all normal salivary cell types: epithelial cells, monocytes, B and T lymphocytes, granulocytes, fungi and bacteria. Each culture was treated by a different environmental stressor: (1) Hypersalinity was induced by adding 150 mM NaCl and incubation for 18 hrs, as previously used for cultured kidney cells[11]. (2) Oxidative stress was induced by adding 0.01% azide and 0.2 Methanol and incubation for 18 hrs. (3) Heat shock was induced by incubation at 44° C. for 2 his followed by incubation at 37° C. for 16 hrs. Similar conditions were previously used to heat shock HeLa cells[12]. (4) Cold shock was induced by freezing saliva at ~80° C. for 2 hrs (3 sterile cryotubes, 1 ml saliva/tube), thawing on ice by adding 1 volume of warm growth medium (RPM with 20% fetal calf serum), transfer into a sterile. Petri dish and incubation at 37° C. for 18 hrs. (5) Desiccation was induced by reducing the culture volume to 1 ml using progressive evaporation during 2 hrs, followed by 16 hr incubation at the same volume. A portion of each treated culture (1 ml from treatments 1-3, 2 ml from treatment 4 and 0.3 ml from treatment 5) was processed individually as "Treated (T1-T5)". Remaining treated cultures were combined into a "Stressed (S) pool" (about 10 ml) before processing into smears on slides. The smears were produced using methods from Example 1.

Figure 2:
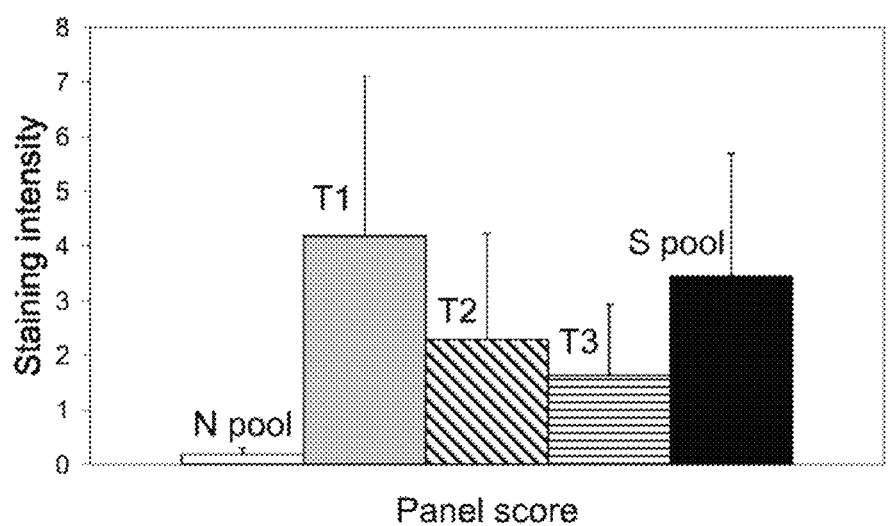
FIG. 2 shows a plot of the levels of stress response (SR) biomarkers in salivary cells treated with different environmental stressors. SR biomarkers were detected using enzymatic immunochemical staining assay with mouse and rabbit antibodies and permanent color label. The staining intensity was measured in relative optical density units using image analysis. The y axis shows the average staining intensity for 40 SR biomarkers. Error bars show standard deviations of the average staining intensity. N pool, untreated salivary cells from three donors. Cultured cells from the N pool were treated by desiccation (T1), hypersalinity (T2) or heat shock (T3). S pool, cells combined after treatment of the N pool by desiccation, hypersalinity, heat shock, oxidative stress and freeze/thaw shock.
Figures 3A, 3B, 3C, 3D, 3E, 3F, 3G, 3H:
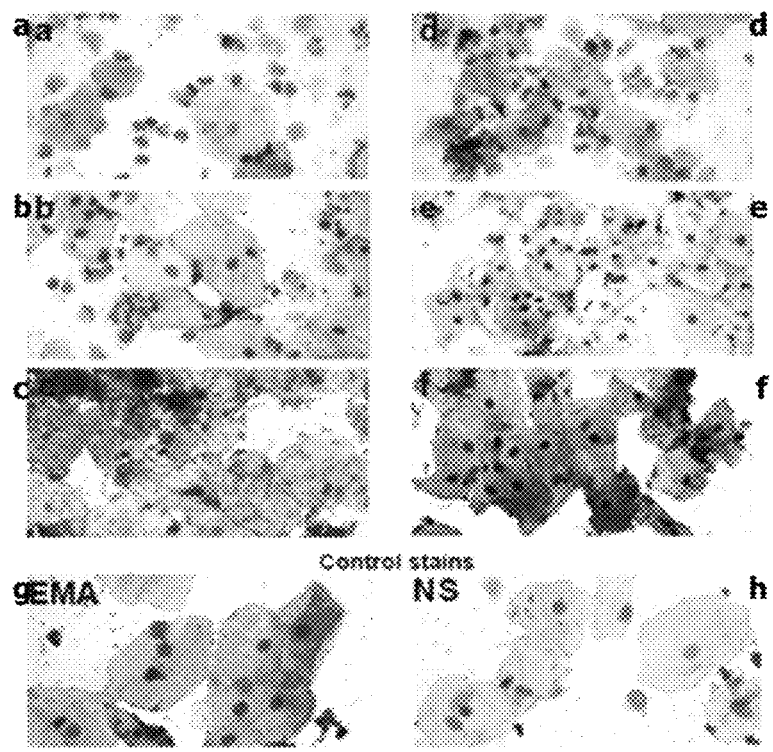
FIGS. 3A-3H show cellular stress in saliva induced by treatment in vitro or by physiological stress in vivo. 40 SR biomarkers were detected in salivary cells using immunochemical staining with a color label. In cell images, the color is shown as stippling.

To determine if the treatments induced cellular stress, 40 SR markers were measured in smears of N pool, S pool and T1-T5 using the ICC assay protocol described in Example 1. The primary antibodies were a pool of antibodies against 40 SRP markers (see Table 2) and control antibodies were as described in Example 1. The treatment was considered successful if the average SR marker level was over 3 fold higher in treated saliva (T1-T5, S pool) than in the N pool, see FIG. 2.

Figure 4:
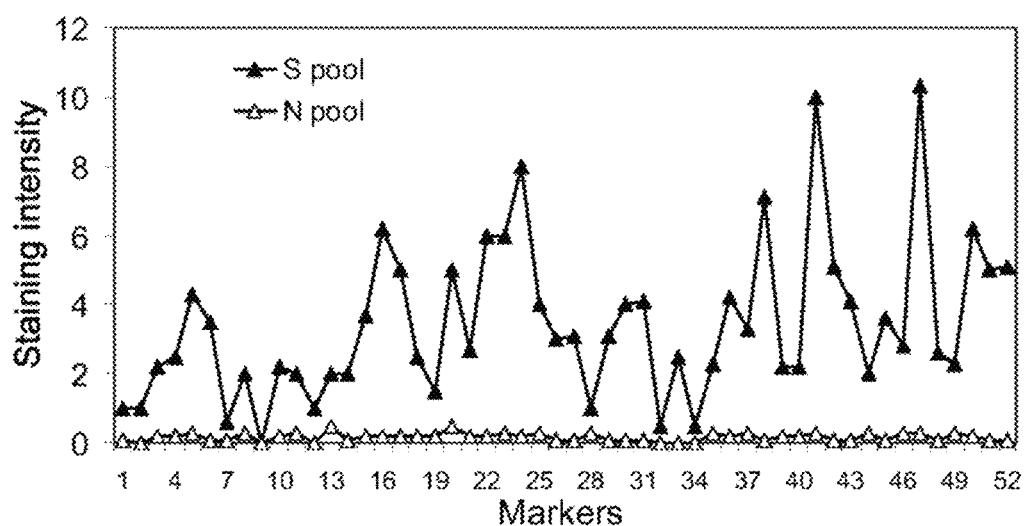
FIG. 4 shows a plot of shows levels of individual SR biomarkers before and after treatment with environmental stressors. 52 SR biomarkers were measured using immunochemical staining and image analysis. The y axis shows the average staining intensity for the 52 biomarkers. N pool, untreated salivary cells from three donors. S pool, cells combined after treatment by desiccation, hypersalinity, heat shock, oxidative stress and freeze/thaw shock.

Although stressed salivary cells can be prepared from using one donor and a single environmental stressor, the preferred method described above is based on the combination of saliva samples from several donors treated using 2 or more different environmental stressors. The preferred method produces a broad-based cellular stress in saliva, as salivary cells from different genetic backgrounds respond to the various stressors by activating multiple stress response pathways. The broad-based cellular stress results in altered levels of numerous biomarkers that are affected by cellular stress. The induced biomarkers are present both within salivary cells and also secreted into the culture medium. FIGS. 3A-3H document that treatment of saliva cells by the preferred method increased levels of SR biomarkers more than 20-fold indicating abroad-based cellular stress. FIG. 4 shows that at least 50 individual SR markers were induced by the preferred method indicating broad-based activation of the 10 principal SR pathways monitored by the 40 markers (see Table 1).

Figure 5:
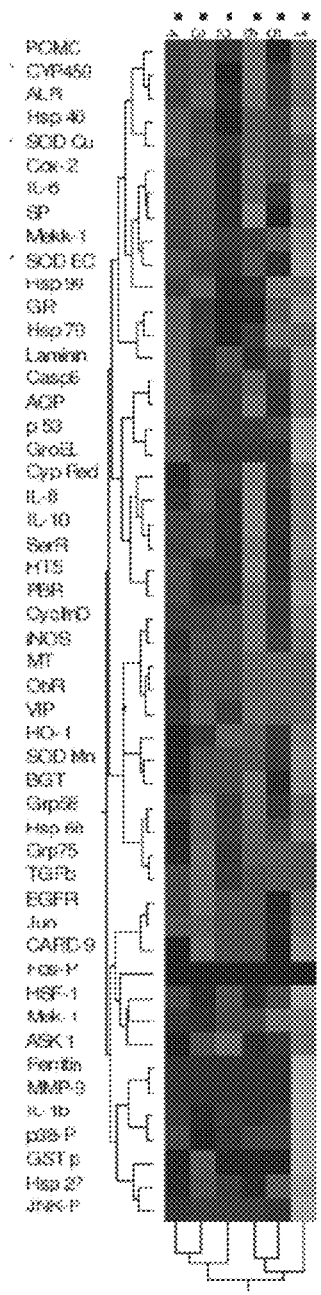
FIG. 5 shows expression profiles of SR biomarkers induced by treatment of salivary cells with different stressors, 52 SR biomarkers were measured using immunochemical staining and image analysis. The measurements were analyzed using hierarchic clustering to depict relatedness between profiles. The color scheme indicates biomarker levels. The lowest level is white, increased levels are gray to black. Similar profiles are in clusters with short dendrogram branches. N, untreated salivary cells from three donors. S, cells combined after treatment by desiccation, hypersalinity, heat shock, oxidative stress and freeze/thaw shock. T1a and T1b, desiccation, two subjects. T2, hypersalinity. T3, heat shock.

FIG. 5 shows that (i) the SR marker profile induce (by desiccation was reproducible in salivary cells from different subjects, (ii) SR profiles discriminated between effects of desiccation, heat shock and hypersalinity and (iii) three SR markers were sufficient to discriminate between effects of desiccation and heat shock.

Broad-based cellular stress in saliva produced by the preferred method is directly relevant to clinical salivary diagnostics because a very similar broad-based cellular stress was found in saliva samples collected from subjects with disease or trauma, see FIGS. 3A-3D.

The 40 SR markers were detected in volunteers with inflammatory conditions that commonly affect the oral cavity (gingivitis and periodontitis). These volunteers typically had about 5-10% higher concentration of salivary leukocytes. The average SR marker concentration was less than 1.1-fold higher in the saliva with inflammatory conditions than in saliva from subjects without the condition (n=10), which is a statistically insignificant. This result indicates that salivary diagnostics of disease or trauma is not affected by common oral inflammatory conditions.

Example 3

Development of Assays for Salivary Biomarkers

This experiment provides an exemplary method for the development of a salivary biomarker assay. The method uses reference reagents and materials prepared as described in Example 2. Two types of laboratory saliva immunoassays are exemplified, the immunocytochemical (ICC) assay and the ELISA assay.

The ICC assay. Methods in Example 2 were used to prepare reference slides for the assay: salivary cell smears of the N and S pools. The reference slides were first used to determine the optimal concentration of the tested anti-marker antibody. The reference slides were prepared using 20 microliter of the N pool horizontally smeared across the top of the slide, and 20 microliter of the S pool smeared across the bottom of the slide. Before staining, the slide was vertically divided into 4 sections by scoring the opposite side of the slide with a glass pen so that cacti section contained the N pool on the top and the S pool on the bottom. The sections were stained with 4 serial dilutions of the anti-marker antibody using the ICC staining protocol from Example 1. Parallel slides were stained with the control antibodies described in Example 1. The optimal concentration of the anti-marker antibody was identified based on the smallest detectable specific staining in the N pool, and the highest signal ratio between N and S pools. The sensitivity of the assay was shown based on the detection of single stained cells. The specificity of the assay was shown as the absence of staining with the negative control antibody. The reproducibility of the assay was shown as <10% CV for repeated measurements of the mean staining intensity in duplicate samples N and S pools in the same assay run and in 3 consecutive runs. Optimal concentrations of 52 SR markers determined using this method are in Table 5.

TABLE 5

Antibodies for the Detection of SR Biomarkers in Salivary Cells

| ANTIGEN | ANTIBODY | M | DF |
|---|---|---|---|
| ASK-1 | AAP-480 | 1 | 1000 |
| Endorphin beta | MAB0905 | 1 | 100 |
| CARD 9 | 905-188 | 1 | 600 |
| Caspase 8 | AAP-118 | 1 | 50 |
| Cyclin D1 | KAM-CC200 | 1 | 100 |
| Cox-2 | sc-7951 | 2 | 600 |
| Cytochrome 450 | MFO-100 | 1 | 600 |
| CYP450 reductase | OSA-300 | 1 | 1000 |
| EGFR | sc-03 | 2 | 150 |
| Ferritin | A0133 | 3 | 3000 |
| Fos | 905-640 | 1 | 10 |
| Glucocorticoid receptor | sc-8992 | 2 | 600 |
| GroEL | SPS-875 | 1 | 600 |
| Grp58 | SPA-580 | 1 | 1000 |
| Grp75 | SPA-825 | 1 | 50 |
| GSTp | A3600 | 3 | 1000 |
| HO-1 | SPA-895 | 1 | 4000 |
| HSF-1 | SPA-901 | 1 | 600 |
| Hsp 25 | SPA-801 | 1 | 400 |
| Hsp 27 | SPA-800 | 1 | 100 |
| Hsp 40 | SPA-400 | 1 | 150 |
| Hsp 60 | SPA-804 | 1 | 750 |
| Hsp 70 | SPA-810 | 1 | 1000 |

TABLE 5-continued

Antibodies for the Detection of SR Biomarkers in Salivary Cells

| ANTIGEN | ANTIBODY | M | DF |
|---|---|---|---|
| Hsp 90 | SPA-830 | 1 | 20 |
| IL-1 beta | sc-7884 | 2 | 800 |
| IL-6 | sc-7920 | 2 | 1000 |
| IL-8 | sc-7922 | 2 | 800 |
| IL-10 | sc-7888 | 2 | 800 |
| iNOS | KAP-NO001 | 1 | 30 |
| Jun | KAP-TF105 | 1 | 150 |
| Laminin | PU078-UP | 1 | 150 |
| Leptin receptor | sc-8391 | 2 | 10 |
| Metallothionein | MO639 | 3 | 15 |
| Mekk-1 | KAP-SA001E | 1 | 100 |
| Mek-1 | KAP-MA010E | 1 | 400 |
| MMP-9 | 905-486 | 1 | 1500 |
| p53 | KAM-CC002 | 1 | 50 |
| PBR | sc-20120 | 2 | 400 |
| Saliva alpha amylase | sc-25562 | 2 | 500 |
| Serotonin | sc-73024 | 2 | 10 |
| Serotonin R1A | 905-741-100 | 1 | 100 |
| Substance P | sc-58591 | 2 | 100 |
| SOD Cu | SOD-100 | 1 | 800 |
| SOD EC | SOD-106 | 1 | 400 |
| SOD Mn | SOD-110 | 1 | 600 |
| TGF beta | sc-7892 | 2 | 400 |
| VIP | sc-20727 | 2 | 100 |
| ALR | sc-33219 | 2 | 250 |
| AQP5 | sc-28628 | 2 | 600 |
| BGT-1 | B1082-10 | 4 | 100 |
| SAPK | KAP-SA011 | 1 | 50 |
| p38-MAPK | KAP-MA022 | 1 | 30 |

M, Manufacturer: 1-Assay Designs, Ann Arbor, MI. 2-Santa Cruz Biotechnology, Santa Cruz, CA. 3-Dako, Carpinteria, CA. 4-US Biological, Swampscott, MA. DF, Dilution Factor.

The ELISA Assay. Methods in Examples 1 and 2 were used to prepare reference samples for the assay: protein lysates of the N and S pools. The tested biomarker was analyzed using a commercial ELISA assay using methods and the control ELISA assay as described in Example 1. The assay was optimized to achieve benchmark values for critical assay parameters as described in Example 1. For large marker panels, the development of a multiplexed ELISA assay (e.g., the 8-plex MultiBead ELISA, Assay Designs) was preferred over the single ELISA assay based on nearly 20-fold lower sample volume per analyte and lower cost per sample for the multiplexed ELISA.

Example 4

Determination of Baseline Concentrations for Salivary Biomarkers

This experiment provides an exemplary method for measuring baseline concentrations of saliva biomarkers using two complementary assays, ICC for cell-associated biomarkers in saliva smears, and ELISA for soluble biomarkers in saliva lysates. The method uses reference reagents and materials prepared in vitro as described in Example 2.

Saliva samples (3 ml) were collected from 10 healthy volunteers at 6 time points (3 days, 8 am and 3 pm) and used to prepare "individual smears" and "individual lysates" using methods from Example 1. On the first collection day, 1 ml aliquots of each sample were combined (20 ml) and used to prepare smears and protein lysates from N and S pools using Methods from Examples 1 and 2. Methods from Example 3 were used to validate saliva ICC and ELISA assays of the tested biomarker.

Using the validated ICC assay, the tested biomarker was measured in triplicate slides of the individual smears. Smears of the N pool and S pool were used as reference slides with normal and increased levels of saliva biomarkers. The mean SI was determined for each smear using image analysis method from Example 1. The baseline was calculated as the average of the mean SI measurements in the individual samples. Individual and daily variability was determined as the standard deviation from the baseline.

Using the validated ELISA assay, the tested biomarker was measured in duplicate samples of individual lysates. Protein lysates of the N pool and S pool were and used as reference samples with normal and increased levels of saliva biomarkers. The baseline was calculated as the average concentration in the individual samples. Individual and daily variability was determined as the standard deviation from the baseline.

Example 5

Construction of a Biomarker Panel for Salivary Diagnostics

This experiment provides an exemplary method for constructing a biomarker panel that is useful for salivary diagnostics of health disorders.

Potential Markers. Potential markers were identified using two methods: (1) Articles describing the molecular mechanism of cellular stress responses (SR) associated with health disorders were collected from peer-reviewed scientific literature. Meta-analysis of the articles was used to select potential biomarkers based on their association with one or more universal SR pathways that are activated in different cell types during more than one health disorder[4-7]. Ten universal SR pathways are described in Table 1. Protein lysates of the N pool and S pool were prepared using methods from Example 2. The lysates were analyzed to identify differentially expressed proteins and peptides using a method with a sufficiently high sensitivity and peptide separation to enable reliable sequencing and identification of peptides in a complex protein mixture such as the saliva lysate, for example the isotopic labeling coupled with liquid chromatography tandem muss spectrometry (IL-LC-MS/MS). Potential biomarkers were identified based on more than 2-fold difference in the concentration between the S and N pools.

Candidate Marker Panel. Reference slides and protein lysates were prepared from the N pool, S pool and treated cultures T1-T5 using methods from Examples 1 and 2. Methods from Example 3 were used to validate ICC and ELISA immunoassays for potential saliva markers. Methods from Example 4 were used to measure the normal baseline and variability of the potential markers. Candidate biomarkers were selected from the potential markers using following criteria: (1) Each marker had a stable baseline in normal saliva based on less than 2-fold individual and daily differences in the marker concentration. In such markers, the ratio between the baseline concentration and the standard deviation of the baseline is less than 0.65. (2) The concentration of each marker was more than 3-fold different between the S and N pools. Preferred markers had more than 3-fold increased concentration in the S pool relative to the N pool. (3) When combined into a panel, the markers discriminated between the T1-T5 saliva samples. A panel of 52 candidate salivary biomarkers identified using this method is shown in Table 5 and FIGS. 2, 3A-3H, 4 and 5.

Initial Clinical Validation. A small-scale clinical study was used to demonstrate that a candidate marker panel had a potential diagnostic value for a specific medical condition.

Clinical saliva samples and gold standard indicators of the medical condition were collected using methods from Example 1. A practical limit for the volume of clinical saliva samples was about 3 ml since in many medical conditions patients cannot produce as much saliva as healthy people. The saliva samples were processed into saliva smears and protein lysates using methods from Example 1. Individual biomarkers were measured in the smears and lysates using the validated. ICC and ELISA assays. The assays used reference slides and lysates with normal and increased levels of saliva biomarkers (the N pool and S pool) prepared from normal saliva using methods from Examples 1 and 2. The discrimination of the medical condition using the saliva biomarker panel was determined using correlation analysis with the gold standard indicator. The diagnostic accuracy of the saliva biomarker for the threshold value of the gold standard indicator was determined using the Receiver Operator Characteristics (ROC) curve analysis, which provided the criterion values (cutoff sensitivity and specificity values that divide true negatives and true positives) and the Area-Under-Curve value (AUC)[13-15]. Optimized biomarker panel was constructed by combining a minimal number of markers that classified the medical condition with the greatest AUC value and the most narrow range of criterion values.

Large-Scale Validation. To efficiently measure biomarkers in large sample sets, a multiplexed ELISA assay for the optimized saliva biomarker panel was produced using a commercial assay platform such in such as MultiBead ELISA (Assay Designs) and methods from Example 3. The assay used reference lysates with normal and increased levels of saliva biomarkers (the N pool and S pool) prepared from normal saliva using methods from Examples 1 and 2. Biomarker measurements obtained by the multiplexed ELISA were used to construct the final biomarker panel that accurately discriminated, the specific medical condition and was not affected by potentially confounding variables such as gender, age and oilier medical conditions.

The final biomarker panel was used for the forward design of a commercial diagnostic test using a mature assay technology with proven acceptability by regulators and customers such as the lateral-flow immunoassay (LFIA)[16-17]. The multiplexed ELISA assay was used as the reference assay in the testing of the commercial test. The prototype test was optimized using reference lysates with normal and increased levels of saliva biomarkers (the N pool and S pool) prepared from normal saliva using methods from Examples 1 and 2.

Example 6

Saliva Test for Monitoring Hydration Status

A rapid saliva test for ≥3% dehydration has been developed using following steps: (1) A candidate panel of 52 SR markers (see Table 5) was constructed using methods from Example 5. (2) The initial clinical validation of the panel used methods from Example 5 and a laboratory study of dehydration induced in healthy volunteers (n–15) by exercise in heat without fluid intake. The study design discriminated between effects of dehydration and exercise-beat. Stable euhydration before the trial was documented based on consistent body mass (±1%), plasma osmolality <290 mOsmol/kg, urine specific gravity <1.02 for 3 days[56]. During the trial, progressive dehydration from 1 to 6% was monitored by 1-4% weight loss. Samples of saliva, blood and urine were collected at 9 time points. The blood and urine samples were used for standard laboratory tests of the hydration status including the gold standard test (plasma osmolality). The clinical saliva samples were collected and processed into smears and protein lysates using methods from Example 1. Individual 52 SR markers were measured in the smears and lysates using optimized ICC and ELISA protocols as described in Example 5. The assays used reference slides and lysates with normal and increased levels of saliva biomarkers (the N pool and S pool) prepared from normal saliva using methods from Examples 1 and 2. The SR marker measurements were correlated with plasma osmolality to determine whether the SR marker measurements were significantly related to plasma osmolality and not affected by potentially confounding effects of exercise-heat, gender and sampling variables. The diagnostic accuracy of the SR markers for the plasma osmolality threshold (296 mOsmol/kg indicating 3% dehydration) was determined using the ROC curve analysis as described in Example 5. A minimal panel of SR markers that had the best diagnostic accuracy for ≥3% dehydration was selected using methods from Example 5.

(3) Methods from Example 5 and a large clinical study of dehydration (n=100) were used to construct the optimized SR marker panel. (4) The optimized SR marker panel was used to produce a prototype LFIA device. The prototype was optimized using reference saliva lysates as described in Example 5. The optimized prototype was tested extensively using clinical saliva samples to demonstrate reliability, accuracy, applicability for field use and regulatory requirements. The multiplexed ELISA assay was used as a reference assay for the LFIA. The LFIA device showed actionable levels of dehydration based on plasma osmolality thresholds: normal (plasma osmolality ≤290 mOsmol/g), moderately dehydrated (2-3% dehydration, osmolality 291-296) and severely dehydrated (dehydration >3%, osmolality >296), see FIG. 6. The benefit of identifying moderate dehydration is that it can be treated in the field by simple oral rehydration that prevents progression to severe dehydration that might require hospitalization and intravenous rehydration.

Example 7

Saliva Test for Monitoring HIV/AIDS Risk and Treatment Outcome

A rapid saliva test for predicting AIDS risk treatment outcome has been developed using following steps: (1) A candidate panel of 52 SR markers (Table 5) was constructed using methods from Example 5. (2) The initial clinical validation of the panel used methods from Example 5 and saliva samples from HIV/AIDS patients (n=100) with CD4 counts >500, 200-500 and <200 cells/mm$^3$. The study subjects had stable CD4 counts during 6 months before enrollment, and also at when tested during the office visit when the saliva sample was collected[68,70-71]. The clinical saliva samples were collected and processed into smears and protein lysates using methods from Example 1. The individual 52 SR markers were measured in the smears and lysates using optimized ICC and ELISA protocols as described in Example 5. The assays used reference slides and lysates with normal and increased levels of saliva biomarkers (the N pool and S pool) prepared from normal saliva using methods from Examples 1 and 2. SR marker measurements in the clinical saliva samples were correlated with matched CD4 counts (the CD4 count measured during the same office visit when the saliva was collected). The diagnostic accuracy of the SR markers for threshold. CD4 counts (≥500 and ≤200 cells/mm³) was determined using the ROC curve analysis as described in Example 5. A minimal panel of SR markers with the best diagnostic accuracy for the threshold CD4 counts was selected using methods from Example 5.

(3) Saliva samples were collected from HIV patients (n–110) at 5 time points during the initial year of the first-line cART. Prior the enrollment, patients had unsuppressed baseline viral load of ≥500 copies/ml and a baseline CD4 count <200 cells/mm³. Benchmarks for successful cART outcome after 9 months (expected in 70-90% of the patients) were: viral load <50 copies/ml, CD4 count increased ≥100 cells/mm3 above the baseline and no AIDS-defining event or death[68-73]. The minimal panel of SR markers produced by the previous study was measured in saliva lysates using multiplexed ELISA as described in Example 5. SR marker measurements were correlated with CD4 count and viral load to determine the prognostic accuracy of SRP markers for cART outcome. The benchmark for prognostic accuracy was the hazard ratio from Cox proportional hazards models at 95% confidence interval. The benchmark for prognostic independence were higher critical chi-square values for Cox models containing SR markers compared to models with CD4 count and viral load alone[69,72]. Results of the study were used to optimize the minimal SR marker panel as outlined in Example 5.

(4) The optimized minimal SR marker panel was used to produce a prototype LFIA device. The prototype was optimized using reference saliva lysates as described in Example 5. The optimized prototype was tested extensively using clinical saliva samples to demonstrate reliability, accuracy, applicability for field use and regulatory requirements. The multiplexed ELISA assay was used as a reference assay for the LFIA. The LFIA device showed actionable levels of AIDS risk based on threshold CD4 counts: low (CD4 count >500 cells/mm³), moderate (CD4 count 500-200 cells/mm³) or high (CD4 count <200 cells). The benefit of identifying a moderate AIDS is that it indicates the need for starting or modifying cART therapy to prevent progression to severe AIDS risk.

Example 8

SRP Analysis of Post-Traumatic Psychological Stress

Figures 8A, 8B, 8C:
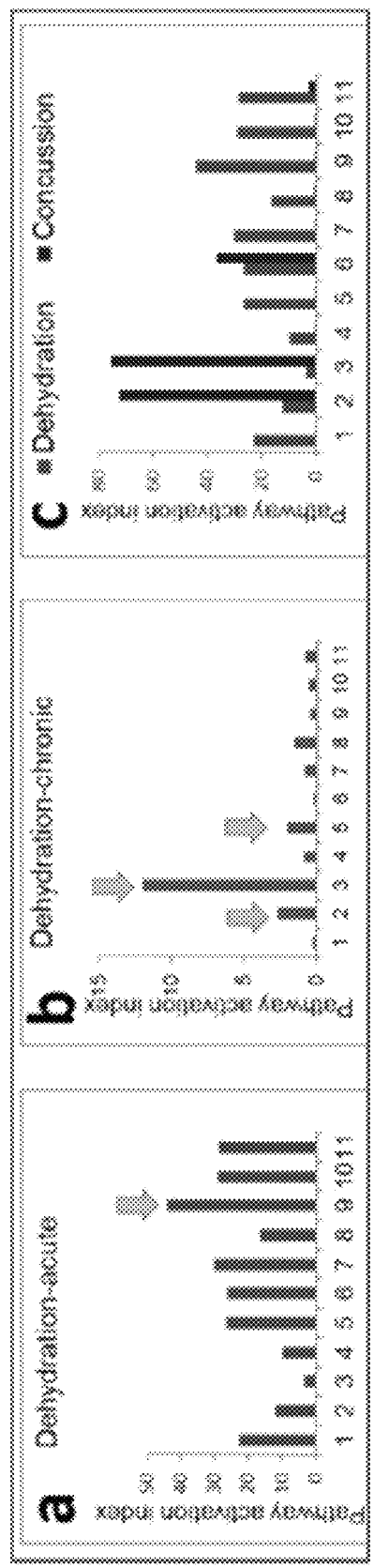
FIGS. 8A-8C show the pathway signature for dehydration.

Multi-SRP assay of saliva was applied to the study of post-traumatic psychological stress. Multi-SRP scores were measured in salivary cells (FIG. 8A). The scores strongly correlated with self-reported health status and provided actionable health care information: normal daily activities were possible at baseline and mildly elevated multi-SRP scores and bed rest was needed at high multi-SRP scores (FIG. 8B).

FIGS. 7A-7B: Multi-SRP scores during post-traumatic psychological distress. Saliva samples were collected from a healthy subject at different time points before and after psychological trauma. FIG. 7A, Multi-SRP staining of saliva cells. Original magnifications: ×200, FIG. 7B, The SRP score was calculated as the ratio between the average staining intensity across 900 saliva cells, and the maximum staining intensity value for saliva cells. The staining intensity was quantified using image analysis. Baseline was calculated as the average across multi-SRP scores for six time points before the psychological stress. The error bars are standard deviations. During the psychological distress, multi-SRP scores correlated with the functional state. Normal daily activities were possible till Day 8 when fatigue was reported. Health status deteriorated on Day 12 and a bed rest was required due to dizziness and nausea. Normal health status was reported on Day 45 post trauma.

Example 9

SRP Biomarkers for Dehydration

The pathway activation index was calculated using a proprietary data mining algorithm and data from the Phase 1 studies. FIG. 8A shows that the neuro-endocrine signaling pathway was preferentially upregulated in acute dehydration consistent with early role of systemic hormonal signaling in the maintenance of water and sodium homeostasis. FIG. 8B shows that the pathway signature is different after 12 hrs of persistent dehydration: the dominant pathways are cellular detoxification, osmotic stress response and DNA repair, consistent with adaptive response to cellular and molecular effects of intracellular water loss and increased salinity. FIG. 8C shows that dehydration and concussion have different pathway signatures even though they share some physical symptoms (e.g. nausea, headache), demonstrating specificity for dehydration. Eighty SRP biomarkers were measured in 195 saliva samples collected from a clinical study of experimentally-induced dehydration. The Pathway activation index was calculated for Acute 4% hypertonic dehydration, Chronic (12 hrs) 4% hypertonic dehydration, Dehydration and concussion using a proprietary algorithm. The results indicate that the signaling pathway is indicated in acute dehydration and osmotic stress, cellular detox and DNA pathways are indicated in chronic dehydration.

Example 10

Saliva Quality Control

It was discovered that human saliva contains a large number of live epithelial cells and leukocytes (2×10⁶/ml), and showed that the cells in saliva actively express disease biomarkers. Classical methods for saliva collection (Salivette device, filtered saliva) do not retain whole cells. To take advantage of the diagnostic, potential of the cells, new methods that reproducibly collect whole saliva including the cells and preserve molecular integrity of saliva proteins were developed. Saliva samples are aliquoted and stored at −80° C. and monitored using a Saliva Quality Control procedure. Optimized algorithm (Tripartite Classification Algorithm, TCA) was developed for accurate and reliable quantification of biomarker signals in INC assays of whole saliva.

Figures 9A, 9B:
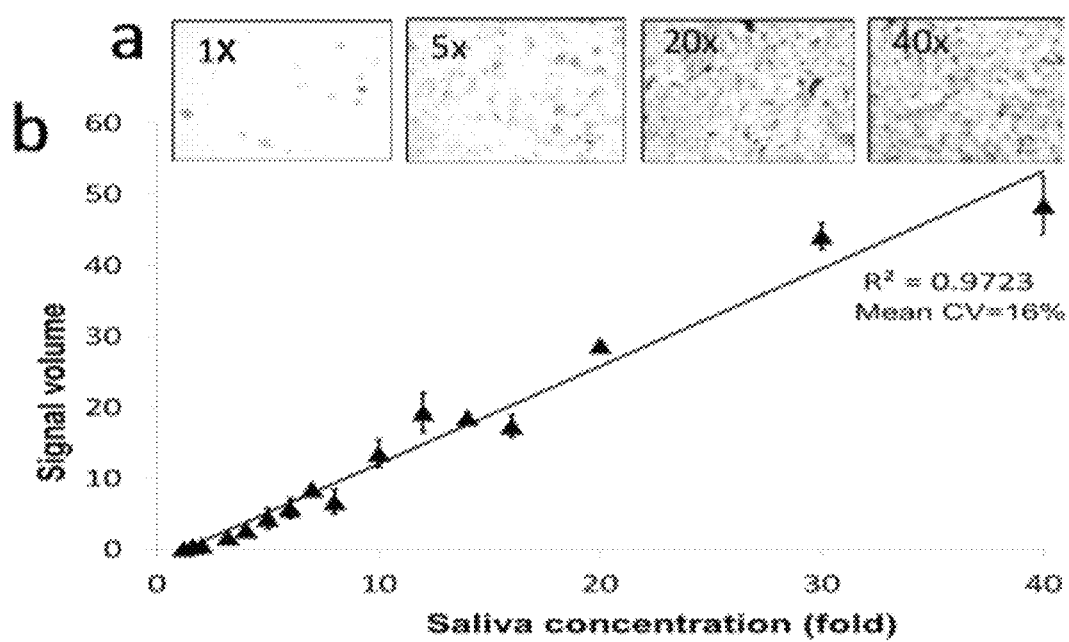
FIGS. 9A-9B show the validation of Mucin 1 IHC assay for whole saliva.
Figure 10:
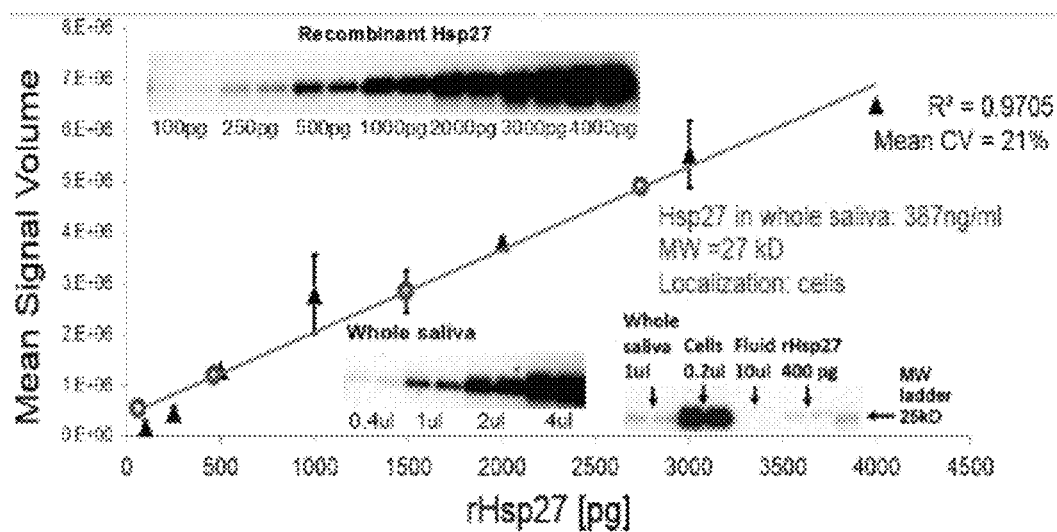
FIG. 10 shows Western blot analysis of whole saliva. Calibration curve was constructed using 7 serial dilutions of recombinant Hsp27 (triangles): 100 pg-4 ng/lane (100 ng-4 ug/ml). 4 dilutions of whole saliva (wen circles) used to determine the Hsp27 protein concentration in the whole saliva.

The TCA algorithm was applied to validate quantitative. IHC assays using standard calibration curves of 5 different biomarkers as illustrated in FIGS. 9A-9B. The IHC assay procedure validated based on high sensitivity (single cells <0.1 pg/ml), reproducibility (mean CV≤20% for duplicate samples) and accuracy across 40-fold change in biomarker concentration (linear dynamic range, R2≥0.95). The image analysis also allows calculating the distribution of the biomarker signal between cells and fluid. The biomarker distribution between saliva cells and fluid is confirmed using Western blot. Knowing where is the biomarker located in saliva is critical for designing the commercial HSM test: cell-associated biomarkers require a lysis step before entering the test strip, Specifically, reference whole saliva was concentrated 40 fold. Duplicate samples of 16 serial dilutions (1× to 40× concentrated saliva) were spread on slides, and Mucin 1 was detected using sandwich immunoassay with red Fuschsin label. The red signal volume was quantified using the TCA algorithm. FIG. 9A. Images of 1× to 40× concentrated saliva stained for Mucin 1 (magnification ×200), FIG. 10B Standard calibration curve for the Mucin1 IHC assay has a linear dynamic range across 40-fold signal increase.

A immunoblotting method was developed for quantification of protein biomarkers in whole saliva: Standardized volume of saliva sample (whole saliva, 30× concentrated saliva cells or cell-free saliva) and a protein standard (recombinant protein) are analyzed using Criterion SDS-PAGE gels. Criterion gels make possible QC monitoring across the workflow: total protein is UV imaged in the gel and on the blot to monitor molecular integrity and transfer efficiency. A specific biomarker is detected using ECL sandwich immunoassay with a chemiluminescent substrate. The chemiluminescent signal is recorded as a series of exposures (typically 1 s-10 min) using the Chemidoc system (Bio-Rad). Digital image analysis is used to determine the molecular weight, protein concentration and localization of the biomarker in cells and/or fluid, see FIG. 16. FIG. 16 shows that the saliva WB assay has a high sensitivity (100 ng/ml), reliability (mean CV≤20%) and accuracy across 40-fold change in biomarker concentration (R2≥0.95 linear dynamic range). Specifically, recombinant Hsp27 protein, whole saliva, saliva cells and saliva fluid were analyzed using digital Western blot to determine the MW, protein concentration and localization of the Hsp27 in whole saliva. Calibration curve was constructed using 7 serial dilutions of recombinant Hsp27 (triangles): 100 pg-4 ng/lane (100 ng-4 ug/ml) (FIG. 10). 4 dilutions of whole saliva (open circles) were used to determine the Hsp27 protein concentration in the whole saliva.

Example 11

Identification of 20 Candidate Biomarkers for Dehydration

Existing saliva samples were obtained from clinical and field studies. Two hundred three samples were collected during field studies of dehydration in US Marines and 195 samples were collected during a clinical study of dehydration. Fifteen healthy men and women age 18-40 were enrolled. Each subject was tested for 8 days to establish euhydrated baseline and daily variability, followed by hypertonic dehydration induced by exercise in heat, euhydrated exercise in heat (control) and isotonic dehydration induced by a diuretic pill (Lasix). The exercise was conducted in an Environmental Chamber with controlled temperature (86-95° F.) and humidity (20-35%). After each dehydration, a standard protocol was used to produce a full rehydration in 2 hrs, based on return to baseline body weight and urine specific gravity (USG). Nude body weight and samples of saliva, blood and urine were collected at 13 time points, and used to determine standard hydration indicators: body mass loss percent (BML %), plasma osmolality (Posm) and USG. In addition, blood and urine were used for clinical laboratory tests: Comprehensive Metabolic Panel (CMP), Complete Blood Count (CBC) and Urine Analysis (UA) that were reviewed by licensed MD to ensure subject health and safety. Eighty SRP biomarkers were measured in the 398 existing saliva samples from the clinical and field studies using the quantitative digital IHC assay described above.

Thirty five biomarkers specific for dehydration were identified based on two critical parameters: 23-fold increase in dehydration (clinical and field), and <2-fold increase in euhydrated controls (clinical and field). The field saliva samples provided a critical refinement by showing which specific biomarkers were not confounded by severe dehydration >4% (USG>1.03, N=36 field samples), extreme environments (110° F., 10% humidity), sleep deprivation, operational stress or tobacco use. These potentially confounding conditions could not be tested in a clinical trial. Diagnostic accuracy often specific biomarkers was determined using ROC curve analysis. Best biomarkers were selected based on diagnostic accuracy 280% for dehydration. Twenty candidate biomarkers are listed in FIG. 11.

Example 12

Feasibility Trial

Figures 12A, 12B:
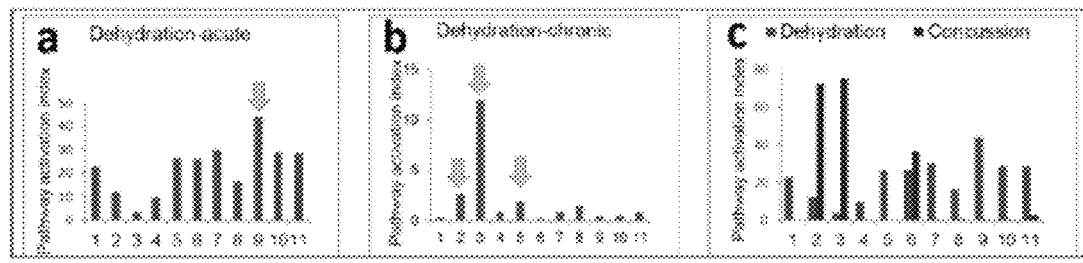
FIGS. 12A-12B show the fold increase in normalized biomarker levels during dehydration relative to euhydrated baseline.
Figures 14A, 14B, 14C, 14D:
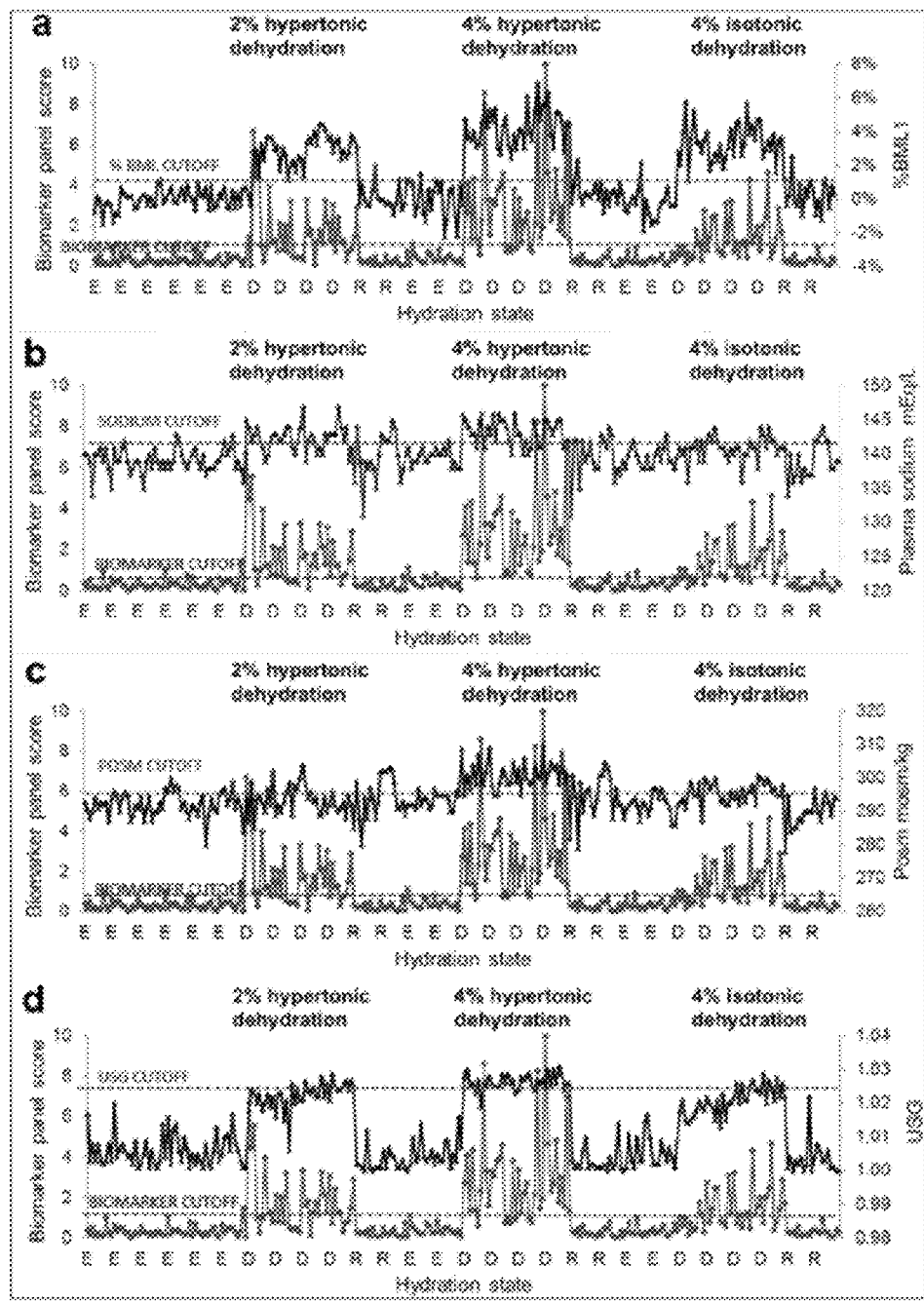
FIGS. 14A-14D show the correlation between final HSM biomarkers and standard hydration indicators. Panel score was correlated with measurements of FIG. 14A. Body Mass Loss (BML %), FIG. 14B, Plasma Sodium (Sodium), FIG. 14C. Plasma Osmolality (Posen) and FIG. 14D. Urine Specific Gravity (USG). Key: E, euhydration. D, dehydration. R, rehydration.

Candidate biomarkers of dehydration were measured in 560 saliva samples. These saliva samples were collected from different subjects than the previous examples and therefore provide an independent validation. The biomarkers were measured using the quantitative digital THC and Western blot assays described previously. FIGS. 12A-12B show the fold increase in normalized biomarker levels during dehydration relative to euhydrated baseline. EUH, euhydrated baseline. HYP, hypertonic dehydration. ISO, isotonic dehydration. Error bars represent standard error. Diagnostic accuracy of the individual biomarkers was determined using ROC curve analysis of the individual IHC data (not shown). The EEC data correlated with the Western blot data based on Spearman's correlation coefficient Rho. Ten biomarkers were validated based on diagnostic accuracy 280% for dehydration. The 10 validated biomarkers are listed are acid trehalase-like protein, aldose reductase, aquaporin 5, induced nitric oxide synthase 2, mucin 1, neuropathy target esterase, nuclear factor of activated T cells 5, osmotic stress protein 94, sodium/myo-inositol cotransporter and trehalase. Each validated biomarker has a diagnostic accuracy 280% for at least 2 dehydration states and rehydration, and diagnostic accuracy <65% for euhydrated exercise demonstrating that the markers are not confounded by the control. The diagnostic accuracy of the 10 biomarkers is not significantly of by gender, daily variability or diurnal variability (data not shown).

Example 13

Analysis of Biomarkers for Dehydration

Stepwise Logistic Regression and Multivariate ROC curves (SAS DAP Pro 11) were used to select a minimal panel of biomarkers with best independent predictive value and highest diagnostic accuracy. Top 3 biomarkers are Acidic Trehalase-like protein 1 (ATHL), Osmotic stress protein 94 (OSP94) and Sodium: myo-inositol cotransporter (SMIT), The statistical analysis was based on results of two orthogonal biomarker assays, MC and Western blot, robustly correlated based on Spearman's correlation coefficient Rho=84-90% (data not shown). To determine the diagnostic accuracy, specificity, sensitivity and cutoff value, a Panel score has been defined as a single numerical value representing all 3 dehydration biomarkers. Algorithm for calculating the panel score P from the normalized biomarker data is provided below:

Panel score $P = \kappa_1 \chi_1 + \kappa_2 \chi_2 + \kappa_3 \chi_3$

Whereas the values of χ are biomarker scores, for example χ1 is ATHL score, χ2 is OSP94 score, χ3 is SMIT score and the values of κ are constants, for example κ1=1.0, κ2=20 and κ3=10.

The Panel scores were used for ROC analysis. The final diagnostic accuracy, specificity and sensitivity of the final biomarker panel are shown in FIGS. 13A-13C, and demonstrates that the diagnostic accuracy is not confounded by the type of level of dehydration, effects of gender, daily and diurnal variability or euhydrated exercise (control). Table 15 also shows that the biomarker panel accurately detects rehydration immediately after subjects completed fluid replacement. Specificity of the biomarkers was demonstrated based on correlation with standard hydration indicators, and correlation between biomarkers and the hydration level (euhydration/dehydration) (FIGS. 14A-14D). Specifically, Panel score was correlated with measurements of Body Mass Loss (BML %), Plasma Sodium (Sodium), Plasma Osmolality (Posm) and Urine Specific Gravity (USG). E, euhydration, D, dehydration, R, rehydration.

The minimal set of biomarkers of dehydration have the following characteristics:
1) best predictors independently associated with dehydration
2) 94% diagnostic accuracy, 88% specificity and 88% sensitivity
3) biomarker scores correlate with standard indicators Body Mass Loss, Plasma Osmolality, Plasma sodium and Urine Specific Gravity
4) diagnostic accuracy is not confounded by type of dehydration (hypertonic/isotonic); level of dehydration (2% and 4%): timing of dehydration (acute or 12 hrs); rehydration; euhydrated exercise; heat; gender; daily and diurnal variability and field condition, sleep deprivation and tobacco use
5) confirmed by IHC, Western blot and Mass spectroscopy.

Example 14

Pathway Signature for HIV

Figures 15A, 15B, 15C:
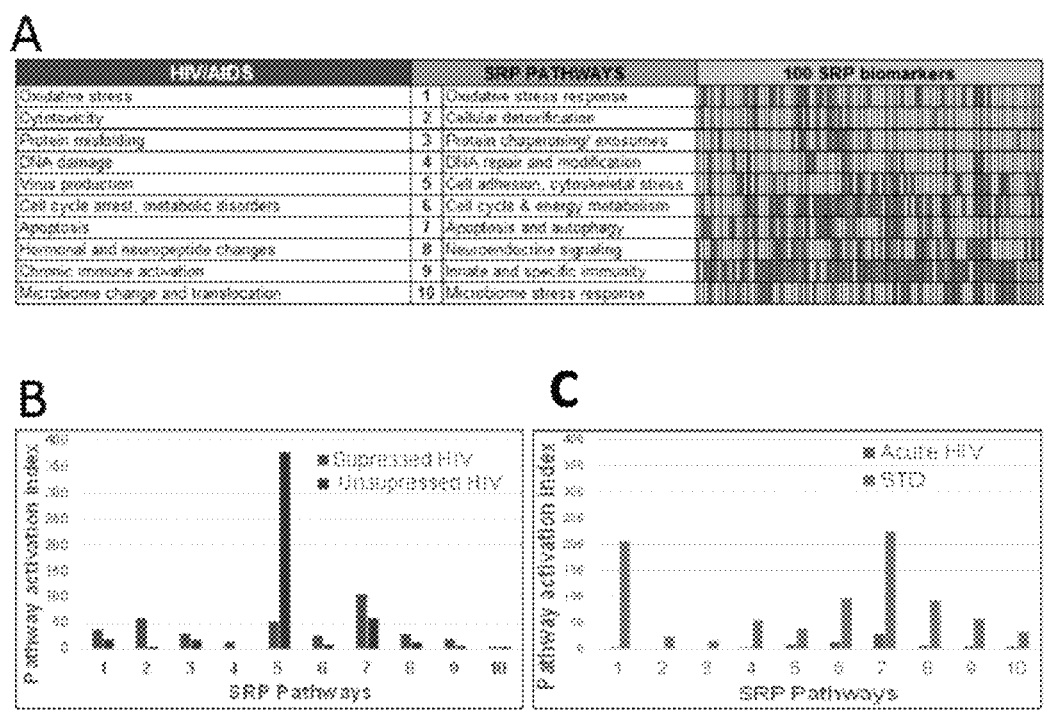
FIGS. 15A-15C show the pathway signature of IV infection.

SRP biomarkers were measured in 58 saliva samples from patients with ART-suppressed or unsuppressed HEY, acute HIV and HIV negative STD (syphilis, gonorrhea or chlamydia) (FIGS. 15A-15C). Pathway activation index was calculated from biomarker data using a proprietary algorithm described previously. The adhesion, cytoskeleton and exosome pathway was preferentially upregulated in unsuppressed HIV, consistent with cytoskeletal stress due to high HIV virus production. Multiple pathways were moderately upregulated in suppressed HIV, in particular apoptosis and autophagy, consistent with restored immunity and active cellular stress responses due to successful ART therapy. Low stress response activation was found in acute HIV consistent with low cytokine levels reported in post viremic HIV. STD had a different pathway signature than HIV, demonstrating the specificity of the HIV pathway signature.

Example 15

Identification of HIV Biomarkers

Whole saliva was used to take advantage of cell-associated. HIV which was identified as the main source of oral HIV. Current methods use filtered saliva Which might have resulted in low HIV concentration. Whole saliva samples (98) (3 ml) were collected using a standardized procedure. Saliva samples were aliquoted and stored at −80° C., and tested before biomarker assays using a standard QC matrix including the total saliva volume, appearance, color, cellular/molecular preservation in epithelial cells and leukocytes. Ninety live SRP biomarkers were quantitatively measured in 89 saliva samples from using high throughput digital IHC assay. The IHC results were confirmed using the digital Western blot. Results identified biomarkers with a significant (P<0.05), over 2-fold change in HIV patients compared to healthy controls. Unsuppressed HIV/AIDS had more altered biomarkers (N=27) then suppressed HIV (N=17) and acute HIV (N=13). HIV specificity was analyzed using Wilcoxon rank sum test (2-tailed test, alpha 0.05). Biomarker profiles in HIV infection (Cohorts 1-3) were significantly different from profiles in HIV-negative STD-positive individuals (Cohort 4), P<0.01, This result agrees with HIV/STD differences demonstrated using the pathway signatures, see FIGS. 15A-15C. To identify candidate biomarkers for diagnostics of unsuppressed and acute HIV, 39 biomarkers with differential expression between Cohorts1/2 and Cohorts 3/4 were examined. Diagnostic accuracy of SRP biomarkers was determined using Receiver Operating Characteristic (ROC) curves. ROC curves were constructed fix 39 biomarkers with differential expression (≥2-fold change, P<0.05) in suppressed/unsuppressed HIV and acute HIV/STD. The area-under the-curve (AUC) value was used to determine the diagnostic accuracy for individual biomarkers. Biomarkers with AUC≥0.8 are in FIG. 16. These markers were further analyzed by multivariate ROC analysis (JMP11Pro SAS) to select minimal biomarker panels with best predictive value. The down-selected 4 markers are BST2, salivary agglutinin gp340 (SAG), cytoplasmic cytochrome c, and vascular endothelial growth factor C (VEGF-C). All the markers have known roles in host response to HIV. BST2 is a cellular HIV restriction factor, cytoplasmic cytochrome c is a mitochondrial protein that triggers apoptosis when released into cytoplasm in HIV-infected cells and is toxic to uninfected bystander cells, SAG binds to the HIV envelope protein gp120 and specifically inhibits HIV-1 infectivity, VEGF-C is a growth factor upregulated by the HIV Tat-1 protein.

Example 16

Pathway Signature and Biomarkers Specific for NCDT

Figures 17A, 17B, 17C, 17D, 17E, 17F, 17G, 17H, 17I:
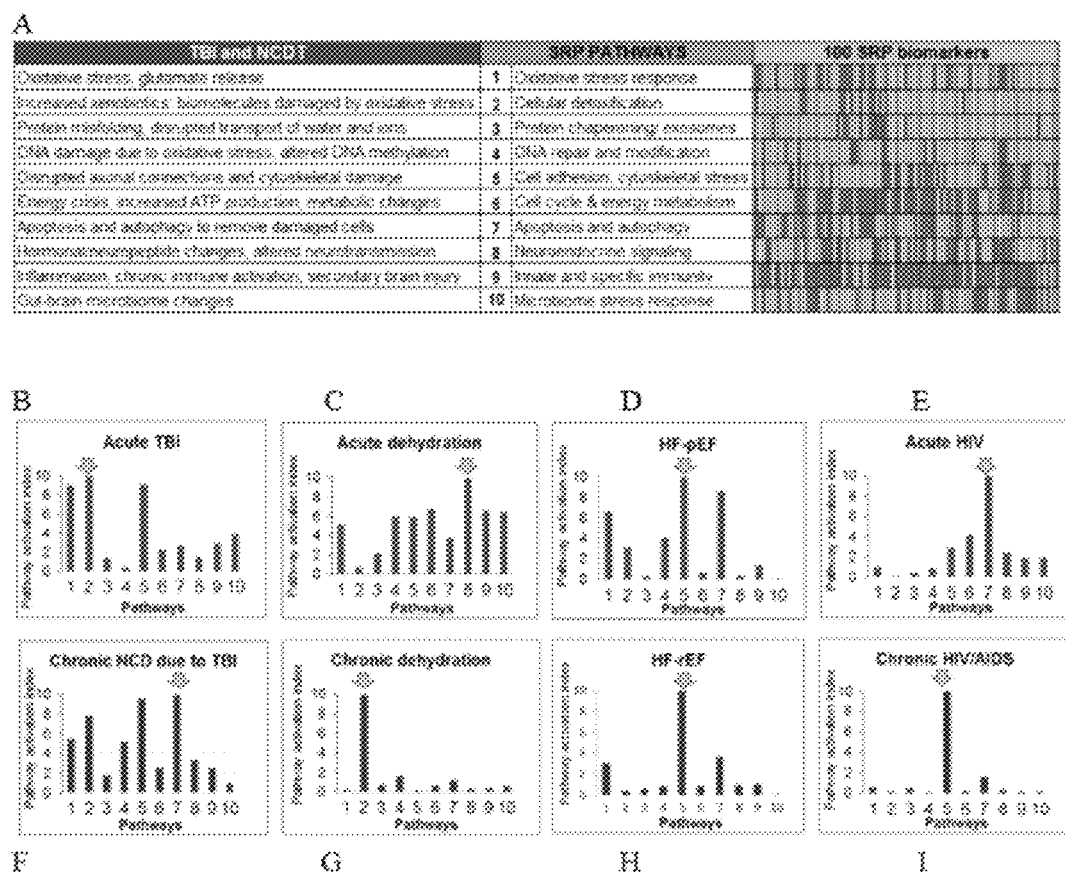
FIGS. 17A-17I show the pathway signature of Neuro-Cognitive Disorder due to TBI. (NCDT) and other diseases.
Figure 18B:
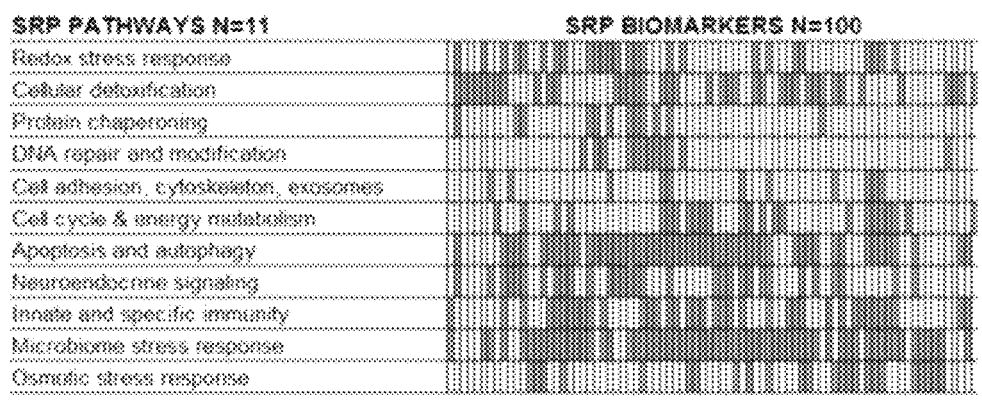

A full panel of 100 SRP biomarkers was profiled in pooled saliva samples from Neuro-Cognitive Disorder due to TB1 (NCDT) and other diseases. Normalized Pathway activation index (0-10) was calculated from biomarker data using a patented algorithm. The arrow indicates the top activated pathway in each disease. SRP pathways: 1—Oxidative stress, 2—Detoxification, 3—Chaperoning, 4—DNA, 5—Adhesion/Cytoskeleton, 6—Cell cycle, 7—Apoptosis, 8—Signaling, 9—Immunity, 10—Microbiome (FIG. 17A). Oxidative stress, cellular detoxification and cytoskeletal damage (Pathways 1, 2 and 5) were preferentially activated in acute TBI (FIG. 17B). Pathways 2 and 5 remain highly activated in NCDT but the dominant pathway 7 is apoptosis (FIG. 17F). The pathway signatures based on saliva SRP biomarkers are consistent with TBI literature. Oxidative stress, cellular detoxification and cytoskeletal damage are known to play key roles in both primary and secondary injury following acute TBI. Apoptosis is rare in acute mTBI (mild traumatic brain injury, concussion); however, it plays important role in long-term evolution of neuro-cognitive deficits and neurodegeneration following mTBI. FIGS. 17A-17I demonstrate that NCDT has a specific pathway signature, distinct front other chronic disease states. FIGS. 17I-17I also show that acute and chronic phases of disease pathogenesis have a distinct molecular mechanism not only in TBI but also other diseases.

Using the above described methods, eight candidate NCDT biomarkers were identified among 91 SRP biomarkers: Adrenocorticotropic hormone (ACTH), Cytochrome P450 Reductase (CYPOR), Epidermal growth factor receptor (EGFR), Glucocorticoid receptor (GR), Home oxygenase 1 (HO), MAP kinase. Mek-1 (MEK) Natriuretic peptide receptor A (NPR) and Oxytocin receptor (OTR). These biomarkers have diagnostic accuracy ≥80% for NCDT (ROC analysis), are ≥3-fold increased in NCDT compared to healthy controls, and <2-fold increased in acute TBI and diseased controls (specificity). Stepwise Logistic Regression and Multivariate ROC curves (SAS JMP Pro 11) were used to select a minimal panel of biomarkers with best independent predictive value and highest diagnostic accuracy. Top 3 biomarkers are Cytochrome P450 Reductase (CYPOR), Natriuretic peptide receptor (NPR) and Oxytocin receptor (OTR).

CYPOR—The NADPH-cytochrome P450 reductase is oxidative enzyme that mediates removal of xenobiotics. Cellular detoxification is critical in TBI because increased levels of xenobiotics are generated by oxidative stress and cytoskeletal damage an acute and delayed phases. Altered expression of detoxification enzymes in the brain was linked to various neurological diseases, and overexpression of detoxification enzymes conferred neuroprotection in animal models. These observations suggest important role for detoxification enzymes such as CYPOR in NCDT pathogenesis.

NPR—The natriuretic peptide receptor A mediates effects of natriuretic peptides ANP and BNP secreted by the heart and the brain. Natriuretic peptides have vasodilating, natriuretic and diuretic activities that modulate blood pressure and cerebral blood flow, and can prevent hypertension and brain edema. Hypertension and brain swelling are common in TBI, and BNP plasma concentrations were found continuously elevated in TBI patients with poor outcomes and cerebral salt wasting. Recently, elevated BNP was linked with deficits in neurocognitive function: memory, processing speed, executive functioning and depressive symptoms, independent of cardiovascular risk factors and cardiac output. These findings suggest that natriuretic peptides and NPR might play a role in NCDT pathogenesis.

OTR—The oxytocin receptor (OTR) regulates effects of the neuropeptide oxytocin (OT). OT is a systemic hormone and neuromodulator that plays a critical role in social and emotional behavior through reduced anxiety, tear and stress reactivity. Intranasal OT is currently tested as a pharmacological agent for the prevention and treatment of PTSD because of its anxiolytic and prosocial properties. Anxiety disorders and antisocial behaviors (irritability, impulsivity and aggression) are core features of NCDT, suggesting that oxytocin and OTR could be involved in the mechanism of NCDT.

Example 17

Pathway Signature and Biomarkers for Heart Failure and Kidney Disease

A full panel of 100 SRP biomarkers was profiled in pooled saliva samples from acute heart failure (AHF) patients stratified into several different disease phenotypes: Preserved Ejection Fraction (HF-pEF). Restricted Ejection Fraction (HF-rEF), Atrial Fibrillation (AFIB), Chronic Kidney Disease (CKD) and Acute Kidney Injury (AKI). Normalized Pathway activation index (0-10) was calculated from biomarker data using a patented algorithm. The arrow indicates the top activated pathway in each disease. SRP pathways: 1—Oxidative stress, 2—Detoxification, 3—Chaperoning, 4—DNA, 5—Adhesion/Cytoskeleton, 6—Cell cycle, 7—Apoptosis, 9—Immunity, 10—Microbiome (FIGS. 17A-17I). Cell adhesion/Cytoskeletal stress pathway, apoptosis and oxidative stress (pathways 5, 7 and 1) were preferentially activated both the HF-pEF and HF-rEF phenotypes (FIGS. 17D and 17H); however, pathway activation was stronger in HF-pEF than HF-rEF. FIGS. 17A-17I demonstrate that AHF has a specific pathway signature, distinct from other chronic diseases. FIG. 17A-17I also show that the HF-pEF and HF-rEF phenotypes have a distinct molecular mechanism.

Selected biomarkers were measured in individual AHF patients and controls. Normalized data was analyzed using ROC curve analysis to determine diagnostic accuracy of the saliva biomarkers. ROC analysis results are provided in FIGS. 19A-19B. Candidate biomarkers were selected based on highest diagnostic accuracy. AHF and AFIB biomarkers include Annexin 5, Cox-2, EGFR, Leptin, MEK1, mTOR, NFAT5, OSP94, SAPK and SOD3. Candidate AKI and CKD biomarkers include Annexin 5, EGFR, Leptin, MEK1, NFAT5 and OSP94.

Example 18

Path AY Signature and Biomarkers for Concussion (Acute mTBI)

Figures 20A, 20B:
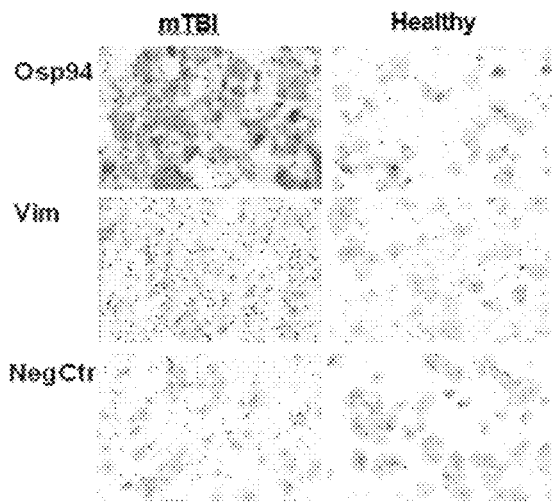

A full panel of 100 SRP biomarkers was profiled in pooled saliva samples from acute mTBI (concussion) and healthy volunteers. Normalized Pathway activation index (0-10) was calculated from biomarker data using a patented algorithm. The arrow indicates the top activated pathway in each disease. SRP pathways: 1—Oxidative stress, 2—Detoxification, 3—Chaperoning, 4—DNA, 5—Adhesion Cytoskeleton, cycle, 7—Apoptosis, 8—Signaling, 9—Immunity, 10—Microbiome (FIGS. 17A-17I). Oxidative stress, cellular detoxification and cytoskeletal damage (Pathways 1, 2 and 5) were preferentially activated in acute mTBI (FIG. 17B). FIGS. 17A-17I demonstrate that acute mTBI has a specific pathway signature, distinct from chronic TBI (NCDT) and other chronic disease states. FIGS. 17A-17I also show that acute and chronic phases of disease pathogenesis have a distinct molecular mechanism not only in TRI but also other diseases. FIGS. 20A-20B show results of two independent studies of mTBI patients. Both studies showed strong increase in over 50 SRP biomarkers in whole saliva. Many of the biomarkers wore consistently increased in both studies demonstrating that the effect is reproducible.

The publications and patents discussed herein are provided solely for their disclosure prior to the tiling date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, literature references, as well as those publications that have been incorporated in those published documents. However, to the extent that any publication incorporated herein by reference refers to information to be published, applicants do not admit that any such information published after the filing date of this application to be prior art.

Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group.

REFERENCES

1. Chiappin, S., Antonelli, G., Gatti, R. & De Palo, E. F. Saliva specimen: a new laboratory tool for diagnostic and basic investigation. Clin Chim Acta 383, 30-40 (2007).
2. Nishanian, P., Aziz. N., Chung, J., Detels. R. & Fahey, J. L. Oral fluids as an alternative to serum for measurement of markers of immune activation. Clin Diagn Lab Immunol 5, 507.12 (1998).
3. Steckfus, C. F. & Bigler, L. R. Saliva as a diagnostic fluid. Oral Dis 8, 69-76 (2002).
4. Southern, S. O. U.S. Provisional Patent Application "Devices and Methods for Early Detection of Chronic Stress and Health Disorders," application Ser. No. 60/910, 158, Filing Date Apr. 4, 2007, (2007).
5. Southern, S. O. International Patent Application entitled. "Systems and Methods for Analyzing Persistent Homeostatic Perturbations." application Ser. No. PCT/US2008/004448. Filing Date Apr. 4, 2008. Claiming priority to U.S. patent application Ser. No. 60/910,158 filed. Apr. 4, 2007. (2008).
6. Southern, S. O. U.S. National Stage Patent Application entitled "Systems and Methods tier Analyzing Persistent Homeostatic Perturbations". Ser. No. PCT/US2008/004448. Filing Date Sep. 12, 2008. Claiming priority to U.S. patent application Ser. No. 60/910,158 filed Apr. 4, 2007. (2008).
7. Southern, S. O. U.S. Provisional Patent Application entitled "Health Test for a Broad Spectrum of Health Problems". Application Ser. No. 61/102,341. Filing Date Oct. 2, 2008. (2008).
8. Rhodus, N. L. et al. A comparison of the pro-inflammatory, NF-kappaB-dependent cytokines: TNF-alpha, IL-1-alpha, IL-6, and IL-8 in different oral fluids from oral lichen planus patients. Clin Immunol 114, 278-83 (2005).
9. Streekfus, C. Mayorga-Wark, O, Daniel Arreola, D, Edwards, C. Bigler, L, Dubinsky, W P. A Comparison of the Oncoproteomic Profiles in Pooled Saliva Specimens from Individuals Diagnosed With Stage IIa and Stage IIb Ductal Carcinoma of the Breast and Healthy Controls. Breast Cancer Res in Review (2009).
10. Tan, W. et al. Optical protein sensor for detecting cancer markers in saliva. Biosens Bioelectron 24, 266-71 (2008).
11, Huang, Z. & Tunnacliffe, A. Response of human cells to desiccation: comparison with hyperosmotic stress response. J Physiol 558, 181-91 (2004).
12. Hang, H., He, L. & Fox, M. H. Cell cycle variation of Hsp70 levels in HeLa cells at 37 degrees C. and after a heat shock. J Cell Physiol 165, 367-75 (1995).
13. Bossuyt, P. M. et al. Towards complete and accurate reporting of studies of diagnostic accuracy: the STARD initiative. Fam Pract 21, 4-10 (2004).
14, de Vries, S. O., Hunink, M. G. & Polak, J. F. Summary receiver operating characteristic curves as a technique for meta-analysis of the diagnostic performance of duplex ultrasonography in peripheral arterial disease. Acad Radiol 3, 361-9 (1996).
15. Singh, G. Determination of Cutoff Score for a Diagnostic Test. The Internet journal of Laboratory Medicine 2 (2007).
16, O'Farrell, B. Developing approaches to the development and manufacture of highly sensitive, reproducible lateral flow assays. Proceedings of the Oak Ridge National Conference. (2006).
17. Park, R. Lateral-flow POC tests to grow. Medical Device Link. May (2007).
18. Institute of Medicine, Hydration status monitoring. In: Monitoring Metabolic Status: Predicting Decrements in Physiological and Cognitive Performance, Washington, D.C.: National Academy Press, 2004, pp. 270-280. (2004).
19. Casa, D. J. Clarkson, P. M. & Roberts, W. O. American College of Sports Medicine roundtable on hydration and physical activity: consensus statements. Curr Sports Med Rep 4, 115-27 (2005).
20. Montain, S. J., Cheuvront, S. N., Carter, R. III, Sawka, M. N. Human water and electrolyte balance. In: Present Knowledge in Nutrition. B. A. Bowman and R. M. Russell Eds., Washington, D.C., ILSI Life Sciences, pp. 422-429, (2006).
21. Sawka, M. N., Cheuvront, N. & Carter, R. 3rd. Human water needs, Nutr Rev 63, S30-9 (2005).
22. World. Health Organization. The treatment of diarrhea: A manual for physicians and other senior health workers, Geneva, Switzerland. (1995).
23. American Dietetic Association. Position of the American Dietetic Association: Oral Health and Nutrition journal of the American Dietetic Association, 107 (8), p. August 2007 107, 1418-1428 (2007).
24. Joint Human Performance Enhancement (JHPE) capability USAMRMC S&T Planning Workshop. Mar. 7, 2008 (2008).
25. Boersma, R, Van Den Brink, W., Deeg, Eefsting, J. A. & Van Tilburg, W. Survival in a population-based cohort of dementia patients: predictors and causes of mortality. Int Geriatr Psychiatry 14, 748-53 (1999).
26. Carter, R., 3rd, Cheuvront, S. N. & Williams, J. O. Epidemiology of hospitalizations and deaths from heat illness in soldiers. Med Sci Sports Exerc 37, 1338-44 (2005).
27. Chassagne, P., Druesne, L., Capet, C., Menard, J. F. & Bercoff, E. Clinical presentation of hypernatremia in elderly patients: a case control study. J Am Geriatr Soc 54, 1225-30 (2006).
28. Cheuvront, S. N., Sawka, M. N. Hydration assessment of athletes. Sports Science Exchange 18, 1-6 (2005).

29. Cheuvront, S. N., Caner, R., 3rd & Sawka, M. N. Fluid balance and endurance exercise performance. Curr Sports Med Rep 2, 202-8 (2003).
30. Cheuvront, S. N., Montain, S. J. & Sawka, M. N. Fluid replacement and performance during the marathon. Sports Med 37, 353-7 (2007).
31. Chuang, S.-F., Sung, J.-M., Kuo, S.-C., Huang, J.-J., Lee, S.-Y. Oral and dental manifestations in diabetic and nondiabetic uremic patients receiving hemodialysis Oral Surgery, Oral Medicine, Oral Pathology, Oral Radiology R. Endodontology 99, 689-695 (2005).
32. Conno, F. D., Ripamonti, C., Sbanotto, A., Ventafridda, V. Oral complications in patients with advanced cancer Journal of Pain and Symptom Management 4, 20-30 (1989).
33. Dalai, S., Bruera, E. Dehydration in cancer patients: to treat or not to treat. The Journal of Supportive Oncology 2, 467-479 (2004).
34. Diggins, K. C. Treatment of mild to moderate dehydration in children with oral rehydration therapy. J Am Acad Nurse Pract 20, 402-6 (2008).
35. Emond, S. Evidence-based emergency medicine/rational clinical examination abstract. Dehydration in infants and young children. Ann Emerg Med 53, 395-7 (2009).
36. Goldman, R. D., Friedman, J. N. & Parkin, P. C. Validation of the clinical dehydration scale for children with acute gastroenteritis. Pediatrics 122, 545-9 (2008).
37, Kooman. J. P., van der Sande, F. M. & Leunissen, K. M. Wet or dry in dialysis—can new technologies help? Semin Dial 22, 9-12 (2009).
38. Lieberman, H. R. et al. Severe decrements in cognition function and mood induced by slip loss, heat, dehydration, and undernutrition during simulated combat. Biol Psychiatry 57, 422-9 (2005).
39. Macy, M. E. A. Trends in High Turnover Stays Among Children Hospitalized in the United States, 1993-2003, Pediatrics 123, 996-1002 (2009).
40. McConnochie, K. M., Conners, G. P., Lu, E. & Wilson, C. How commonly are children hospitalized for dehydration eligible for care in alternative settings? Arch Pediatr Adolesc Med 153, 1233-41 (1999).
41. Merenstein, D., Egleston, B. & Diener-West, M. Lengths of stay and costs associated with children's hospitals. Pediatrics 115, 839-44 (2005),
42. Paul, I. M., Phillips, T. A. Widome, M. D. & Hollenbeak, C. S. Cost-effectiveness of postnatal home nursing visits for prevention of hospital care for jaundice and dehydration. Pediatrics 114, 1015-22 (20(14).
43. Rypkema, G. et al. Cost-effectiveness of an interdisciplinary intervention geriatric inpatients to prevent malnutrition. J Nutr Health Aging 8, 122-7 (2004).
44. Sawka M N, B. Eichner E R, Maughan R J, Montain S J, and Stachenfeld N S. American College of Sports Medicine Position Stand. Exercise and Fluid Replacement, Med Sci Sports Exerc 39 337-90 (2007).
45. Scully, C. F., D. H. Oral Medicine—Update for the dental practitioner: Dry mouth and disorders of salivation British Dental Journal 199, 423-427 (2005).
46. Smith. S. Clinical signs of dehydration in children. Emerg 24, 605 (2007).
47, Thomas, D. R., Tariq, S. H., Makhdomm, S., Haddad, R. & Moinuddin, A. Physician misdiagnosis of dehydration in older adults. J Am Med Dir Assoc 4, 251-4 (2003).
48. Van der Riet, P., Brooks, D., Ashby, M. Nutrition and hydration at the end of life, J Law Med 14, 182-98 (2006).
49. Wakefield, B., Mentes, J., Dimielinann, L. & Culp. K. Monitoring hydration status in elderly veterans. West J Nurs Res 24, 132-42 (2002),
50. Wakefield, B. J., Mentes, J., Holman, J. E. & Culp, K. Risk factors and outcomes associated with hospital admission for dehydration. Rehabil Nurs 33, 233-41 (2008).
51. Warren, J. L. et al. The burden and outcomes associated with dehydration among US elderly, 1991. Am J Public Health 84, 1265-9 (1994),
52. Ciao, H., Barber, J. & Campbell, E. S, Economic burden of dehydration among hospitalized elderly patients. Am J Health Syst Pharm 61, 2534-40 (2004).
53. Almond, C. Hyponatremia among runners in the Boston Marathon The New England journal Of Medicine 352, 1550-6 (2005).
54. Florida initiative aims to slash unnecessary admissions clue to 'catch-all' dehydration diagnosis. Clin Resour Manag 2, 77-9, 65 (2001).
55. Dimant. J. Delivery of nutrition and hydration care in nursing homes: assessment and interventions to prevent and treat dehydration, malnutrition, and weight loss. J Am Med Dir Assoc 2, 175-82 (2001).
56. Popowski, L. A. et al. Blood and urinary measures of hydration status during progressive acute dehydration. Med Sci. Sports Exerc 33, 747-53 (2001).
57. Shirreffs, S. M., Taylor, A. J., Leiper, J. B. & Maughan, R. J. Post-exercise rehydration in man: effects of volume consumed and drink sodium content. Med Sci Sports Exerc 28, 1260-71 (1996).
58. Montain, S. J., Ely, M. R. & Cheuvront, S. N. Marathon performance in thermally stressing conditions. Sports Med 37, 320-3 (2007).
59. US Army Medical Research and Materiel Command Task Area T: Warfighter Protection and Injury Prevention in Extreme Environments, Environmental Health and Protection Program Area (new task effective FY09 replacing Technology Objective (ATO) Biomedical Enablers of Operational Health and Performance (IV.MD.2006-01). (2008).
60. McGown, C. M. et al. Gold medal volleyball: the training program and physiological profile of the 1984 Olympic champions. Res Q Exerc Sport 61, 196-200 (1990).
61. O'Brien. K. K. et al. Hyponatremia associated with overhydration in U.S. Army trainees. Mil Med 166, 405-10 (2001).
62. Godek., S. F., Bartolozzi, A. R., Burkholder, R., Sugarman, E. & Dorshimer, G. Core temperature and percentage of dehydration in professional football linemen and backs during preseason practices. J Athl Train 41, 8-14; discussion 14-7 (2006).
63. Oppliger, R. A. & Bartok, C. Hydration testing of athletes. Sports Med 32, 959-71 (2002).
64. Albert, S. Ci., Nakra. B. R., Grossberg, G. T. & Caminal, E. R. Drinking behavior and vasopressin responses to hyperosmolality in Alzheimer's disease. Int Psychogeriatr 6, 79-86 (1994),
65. Montain, S. J. C., S N; Sawka, M. N. Exercise associated hyponatraemia: quantitative analysis to understand the aetiology. British Journal of Sports Medicine 41, 98-105 (2006).
66. Chumlea, W, C. et al, Total body water reference values and prediction equations for adults. Kidney Int 59, 2250-8 (2001).

67. Campsmitb, M., Rhodes, P, Hall, H I, Green, T. HIV prevalence estimates—United States, 2006 MMWR, Centers for Disease Control and Prevention 57, 1073-1076 (2008).
68. Department of Health and Human Services. Guidelines for the use of antiretroviral agents in HIV-1-infected adults and adolescents. http://aidsinfo.nih.gov/ContentFiles/AdultandAdolescentGL.pdf (2008).
69, Langford, S. E., Ananworanich. & Cooper, D. A. Predictors of disease progression in HIV infection: a review, AIDS Res Ther 4, 11 (2007).
70. Khanlou, H., Guyer, B. & Farthing, C. Efficacy of tenofovir as intensification of zidovudine/lamivudine/abacavir fixed-dose combination in the treatment of HIV-positive patients, J Acquis Immune Defic Syndr 38, 627-8 (2005),
71. Ortiz, R, et al. Efficacy and safety of once-daily darunavir/ritonavir versus lopinavir/ritonavir in treatment-naive HIV-1-infected patients at week 48. Aids 22, 1389-97 (2008).
72. Kulkarni. H. et al. CCL3L1-CCR5 genotype improves the assessment of AIDS Risk in HIV-1-infected individuals, PLoS ONE 3, e3165 (2008).
73. Mitsuyasu, R. T. et al. Phase 2 gene therapy trial of an anti-HIV ribozyme in autologous CD34+ cells. Nat Med 15, 285-92 (2009).
74. Liu, F. R. et al. Correlation analysis on total lymphocyte count and CD4 count of HIV-infected patients, Int J Clin Pract 62, 955-60 (2008).

Although the invention has been described with reference to the above examples, it will be understood that modifications and variations are encompassed within the spirit and scope of the invention. Accordingly, the invention is limited only by the following claims.

What is claimed is:

1. A method for detecting traumatic brain injury (TBI) in a subject comprising:
   (i) processing a salivary cell sample from the subject for biomarker analysis comprising:
      (a) applying a sample of saliva or salivary cells from a subject to a substrate;
      (b) fixing the cells;
      (c) incubating the cells in a citrate buffer at about pH 3.0 at 37° C.;
      (d) contacting the cells with serum;
      (e) applying a primary antibody for each of biomarker of a biomarker panel; and
      (f) detecting the binding of the primary antibody using a secondary antibody having a detectable label, wherein the label is detected optically using a computerized image analysis, and
   (ii) detecting an altered level of at least one biomarker in the sample as compared to a corresponding sample from a subject not having TBI, wherein an alteration in the level of biomarker is indicative of a stress response associated with TBI,
   wherein the at least one biomarker is neuropathy target esterase (NTE), alone or in combination with any one marker selected from the group consisting of ALG-2 interacting protein X (Alix), CD63 (Tetraspanin, LAMP-3), Cytochrome P450 Reductase (CYPOR), Glucose regulated protein 58 (Grp58), Hypoxia-induced factor alpha 1 (HIF1), Leptin, MAP kinase Mek-1, mitogen activated (MEK1), MAP kinase Mekk-1, stress activated (MEKK1), Matrix metalloproteinase 9 (MMP9), Natriuretic peptide receptor A (NPR), Nitric oxide synthase, Oxytocin receptor (OTR), Superoxide dismutase 3 Extracellular (SOD3), Toll-like receptor 3 (TLR3), Toll-like receptor 7 (TLR7), Toll-like receptor 8 (TLR8), and any combination thereof,
   thereby detecting TBI in the subject.

2. The method of claim 1, wherein traumatic brain injury is selected from the group consisting of mild TBI (mTBI, concussion), severe TBI (sTBI) and neurocognitive disorder (NCD) due to TBI (NCDT).

3. The method of claim 1, wherein the at least one biomarker is selected from the group consisting of: Cytochrome P450 Reductase (CYPOR), Heme oxygenase 1 (HO), MAP kinase Mek-1 (MEK), Natriuretic peptide receptor A (NPR) and Oxytocin receptor (OTR) and a combination thereof.

4. The method of claim 1, wherein the at least one biomarker comprises NTE and HIF-1A.

5. A method for detecting mild TBI (concussion) in a subject comprising:
   (i) processing a salivary cell sample from the subject for biomarker analysis comprising:
      (a) applying a sample of saliva or salivary cells from a subject to a substrate;
      (b) fixing the cells;
      (c) incubating the cells in a citrate buffer at about pH 3.0 at 37° C.;
      (d) contacting the cells with serum;
      (e) applying a primary antibody for each of biomarker of a biomarker panel; and
      (f) detecting the binding of the primary antibody using a secondary antibody having a detectable label, wherein the label is detected optically using a computerized image analysis; and
   (ii) detecting an altered level of neuropathy target esterase (NTE) in the sample, as compared to a corresponding sample from a subject not having a concussion, wherein an increase in the level of NTE is indicative of a stress response associated with concussion, thereby detecting mild TBI (concussion) in the subject.

6. A method for detecting concussion in a subject comprising:
   (i) processing a salivary cell sample from the subject for biomarker analysis comprising:
      (a) applying a sample of saliva or salivary cells from a subject to a substrate;
      (b) fixing the cells;
      (c) incubating the cells in a citrate buffer at about pH 3.0 at 37° C.;
      (d) contacting the cells with serum;
      (e) applying a primary antibody for each of biomarker of a biomarker panel; and
      (f) detecting the binding of the primary antibody using a secondary antibody having a detectable label, wherein the label is detected optically using a computerized image analysis, and
   (ii) detecting an altered level of at least one biomarker in the sample comprising salivary cells from the subject, as compared to a corresponding sample from a normal subject, wherein an alteration in the level of biomarker is indicative of a stress response associated with concussion,
   wherein the at least one biomarker is neuropathy target esterase (NTE), alone or in combination with any one marker selected from the group consisting of ALG-2 interacting protein X (Alix), CD63 (Tetraspanin, LAMP-3), Cytochrome P450 Reductase (CYPOR), Glucose regulated protein 58 (Grp58), Hypoxia-induced factor alpha 1 (HIF1), Leptin, MAP kinase Mek-1, mitogen activated (MEK1), MAP kinase Mekk-1, stress activated (MEKK1), Matrix metalloproteinase 9 (MMP9), Natriuretic peptide receptor A (NPR), Nitric oxide synthase, Oxytocin receptor (OTR), Superoxide dismutase 3 Extracellular (SOD3), Toll-like receptor 3 (TLR3), Toll-like receptor 7 (TLR7), Toll-like receptor 8 (TLR8), and any combination thereof,
thereby detecting concussion in the subject.

* * * * *